United States Patent
Beard et al.

(10) Patent No.: US 9,850,264 B2
(45) Date of Patent: Dec. 26, 2017

(54) USE OF AGONISTS OF FORMYL PEPTIDE RECEPTOR 2 FOR TREATING OCULAR INFLAMMATORY DISEASES

(71) Applicant: Allergan, Inc., Irvine, CA (US)

(72) Inventors: Richard L. Beard, Newport Beach, CA (US); John E. Donello, Dana Point, CA (US); Veena Viswanath, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 740 days.

(21) Appl. No.: 14/196,047

(22) Filed: Mar. 4, 2014

(65) Prior Publication Data

US 2014/0256684 A1    Sep. 11, 2014

Related U.S. Application Data

(60) Provisional application No. 61/773,773, filed on Mar. 6, 2013.

(51) Int. Cl.

| | |
|---|---|
| *A61K 31/66* | (2006.01) |
| *A61K 31/554* | (2006.01) |
| *A61K 31/47* | (2006.01) |
| *A61K 31/42* | (2006.01) |
| *A61K 31/41* | (2006.01) |
| *A61K 31/415* | (2006.01) |
| *C07F 9/40* | (2006.01) |
| *C07C 235/82* | (2006.01) |
| *C07C 275/42* | (2006.01) |
| *C07D 217/24* | (2006.01) |
| *C07D 223/10* | (2006.01) |
| *C07D 233/02* | (2006.01) |
| *C07D 235/02* | (2006.01) |
| *C07D 257/04* | (2006.01) |
| *C07D 261/12* | (2006.01) |
| *C07D 401/06* | (2006.01) |
| *C07D 401/14* | (2006.01) |
| *C07D 403/14* | (2006.01) |
| *C07D 405/06* | (2006.01) |
| *C07D 409/06* | (2006.01) |
| *A61K 9/00* | (2006.01) |
| *A61K 31/17* | (2006.01) |
| *A61K 31/196* | (2006.01) |
| *A61K 31/4166* | (2006.01) |
| *A61K 31/662* | (2006.01) |

(52) U.S. Cl.
CPC .............. *C07F 9/40* (2013.01); *A61K 9/0048* (2013.01); *A61K 31/17* (2013.01); *A61K 31/196* (2013.01); *A61K 31/4166* (2013.01); *A61K 31/42* (2013.01); *A61K 31/662* (2013.01); *C07C 235/82* (2013.01); *C07C 275/42* (2013.01); *C07D 217/24* (2013.01); *C07D 223/10* (2013.01); *C07D 233/02* (2013.01); *C07D 235/02* (2013.01); *C07D 257/04* (2013.01); *C07D 261/12* (2013.01); *C07D 401/06* (2013.01); *C07D 401/14* (2013.01); *C07D 403/14* (2013.01); *C07D 405/06* (2013.01); *C07D 409/06* (2013.01); *A61K 9/0019* (2013.01)

(58) Field of Classification Search
None
See application file for complete search history.

(56) References Cited

U.S. PATENT DOCUMENTS

| | | |
|---|---|---|
| 4,521,210 A | 6/1985 | Wong |
| 7,820,673 B2 | 10/2010 | Kubo et al. |
| 8,492,556 B2 | 7/2013 | Beard et al. |
| 8,541,577 B2 | 9/2013 | Beard et al. |
| 8,580,817 B2 | 11/2013 | Beard et al. |
| 8,658,803 B2 | 2/2014 | Beard et al. |
| 8,993,780 B2 | 3/2015 | Beard et al. |
| 9,351,948 B2 | 5/2016 | Beard et al. |
| 9,579,307 B2 | 2/2017 | Beard et al. |
| 9,670,150 B2 | 6/2017 | Beard et al. |
| 2002/0052417 A1 | 5/2002 | Klingler |
| 2005/0137230 A1 | 6/2005 | Dorsch et al. |
| 2006/0160856 A1 | 7/2006 | Dahl et al. |
| 2007/0065819 A1* | 3/2007 | Hinuma .............. C07K 14/723 435/6.14 |
| 2009/0054342 A1* | 2/2009 | Cohen .................... C07K 5/101 514/1.1 |
| 2010/0035932 A1* | 2/2010 | Schepetkin .......... A61K 31/357 514/336 |
| 2011/0144033 A1 | 6/2011 | Bernardini |

(Continued)

FOREIGN PATENT DOCUMENTS

| | | |
|---|---|---|
| JP | 63232846 | 9/1988 |
| WO | 2001-014328 | 3/2001 |

(Continued)

OTHER PUBLICATIONS

Roland Burli, Potent hFPRL1 (ALXR) Agonists as Potential Anti-Inflammatory Agents, Bioorganic & Medicinal Letters, 2006, 3713-3718, 16.

(Continued)

*Primary Examiner* — Jeffrey S Lundgren
*Assistant Examiner* — Michael Schmitt
(74) *Attorney, Agent, or Firm* — Barbara C. Potts

(57) ABSTRACT

The present invention relates to a method for treating ocular inflammatory diseases in a subject in need of such treatment, which comprises administering a pharmaceutical composition comprising a therapeutically effective amount of at least one agonist of Formyl peptide receptor 2.

2 Claims, 3 Drawing Sheets

(56) References Cited

U.S. PATENT DOCUMENTS

| | | |
|---|---|---|
| 2011/0319454 A1 | 12/2011 | Beard |
| 2012/0142726 A1 | 6/2012 | Beard et al. |
| 2012/0208842 A1 | 8/2012 | Beard et al. |
| 2012/0238628 A1 | 9/2012 | Vuligonda et al. |
| 2012/0329873 A1 | 12/2012 | Li et al. |
| 2013/0217720 A1 | 8/2013 | Beard et al. |

FOREIGN PATENT DOCUMENTS

| | | |
|---|---|---|
| WO | 2006065755 A2 | 6/2006 |
| WO | 2007-076055 A2 | 7/2007 |
| WO | 2013-009543 | 1/2013 |
| WO | 2013-062947 A1 | 5/2013 |
| WO | 2013-070600 | 5/2013 |
| WO | 2013-158597 A1 | 10/2013 |

OTHER PUBLICATIONS

International Search Report mailed Jul. 18, 2014, for PCT Application No. PCT/US2014/020245 filed Mar. 4, 2014, 6 pages.

Chiang N, et al., The lipoxin receptor ALX: Potent ligand-specific and stereoselective actions in vivo. Pharmacological Reviews 2006; 58: 463-519.

Dufton N, et al., Therapeutic anti-inflammatory potential of formyl peptide receptor agonists. Pharamcology & Therapeutics 2010; 127: 175-188.

Dufton N, et al., Anti-inflammatory role of the murine formyl-peptide receptor 2: Ligand-specific effects on leukocyte responses and experimental inflammation. Journal of Immunology 2010; 184: 2611-2619.

Maderna P, et al., FPR2/ALX receptor expression an dinternalization are critical for lipoxin A4 and annexin-derived peptide-stimulated phagocytosis. FASEB 2010; 24: 4240-4249.

Reville K, et al., Lipoxin A4 redistributes Mysoin IIA and Cdc42 in macrophages: Implications for phagocytosis of apoptotic leukocytes. Journal of Immunology 2006; 176: 1878-1888.

Serhan C. Resolution phase of inflammation: Novel endogenous anti-inflammatory and proresolving lipid mediators and pathways. Annual reviews of Immunology 2007; 25: 101-137.

Medeiros R, et al., Molecular mechanisms of topical anti-inflammatory effects of lipoxin A(4) in endotoxin-induced uveitis Molecular Pharmacology 2008; 74: 154-161.

Gronert K, et al., A role for the mouse 12/15-lipoxygenase pathways in promoting epithelial wound healing and host defense. Journal of Biological Chemistry 2005; 280: 15267-15278.

Leedom A, et al., Endogenous LXA4 circuits are determinants of pathological angiogenesis in response to chronic injury. American Journal of Pathology 2010; 176: 74-84.

Gronert K. Lipoxins in the eye and their role in wound healing. Prostaglandins, Leukotrienes and Essential fatty Acids. 73: 221-229.

Gavins Fne, Hughes EL, Buss Naps, Holloway PM, Getting SJ, Buckingham JC. Leukocyte recruitment in the brain in sepsis: involvement of the annexin1 FPR2IALX anti-inflammatory system. FASEB 2012; 26: 1-13.

Takano T, Fiore S, Maddox JF, Brady HR, Petasis NA, Serhan CN. Asprin-triggered 15-epi-lipoxin A4 and LXA4 stable analogues are potent inhibitors of acute inflammation: evidence for antiinflammatory receptors. Journal of Experimental Medicine 1997; 185: 1693-1704.

Leoni G, Alam A, Neumann PA, Lambeth JD, Cheng G, McCoy J, Hilgarth RS, Kundu K, Murthy N, Kusters D, Reutelingsperger C, Perretti M, Parkos CA, Neish AS, Nusrat A. Annexin A 1, formyl peptide receptor, and NOX1 orchestrate epithelial repair. Journal of Clinical Investigation. 2013; 123:443-54.

Tsuruki T, Takahata K, Yoshikawa M. Mechanism of the protective effect of intraperitoneally administered agonists for formyl peptide receptors against chemotherapy-induced alopecia. Biosci Biotechnology Biochemistry. 2007;71: 1198-202.

Yamasaki K, Di Nardo A, Bardan A, Murakami M, Ohtake T, Coda A, Dorschner RA, Bonnart C, Descargues P, Hovnanian A, Morhenn VB, Gallo RL. Increased serine protease activity and cathelicidin promotes skin inflammation in rosacea. Nature Medicine. 2007;13:975-80.

Czernilofsky et al., Affinity label for the tRNA binding site on the *Escherichia coli* ribosome, Biochimica Et Biophysica Acta, 272 (1972) 667-671.

Felicity N. E. Gavins et al., Leukocyte recruitment in the brain in sepsis: involvement of the annexin 1-FPR2/ALX anti-inflammatory system, The FASEB Journal, vol. 26 Dec. 2012.

Kazuo Iwaki et al., Optical Resolution of Enantiomeric Amino Acid Derivatives on a Naphthylethylurea Multiple-Bonded Chiral Stationary Phase Prepared Via an Activated Carbamate Intermediate, Journal of Chromatography, 404 (1987) 117-122.

K. Iwaki et al., Preparation of Chiral Stationary Phase via Activated Carbamate Intermediate for Liquid Chromatographic Optical Resolution, Chromatographia vol. 23, No. 10, Oct. 1987.

International Search Report PCT/US2013/036715, Jun. 28, 2013.

Migeotte. Isabelle, et al., Formyl peptide receptors: A promiscuous subfamily of G protein-coupled receptors controlling immune responses, Cytokine & Growth Factor Reviews 17, 2006, pp. 501-519.

Cross, L.C., Rules for the Nomenclature of Organic Chemistry Section E: Stereochemistry, International Union of Pure and Applied Chemistry, vol. 45,1976, pp. 11-13.

Stahl, Heinrich P., et al., Handbook of Pharmaceutical Salts Properties, Selection, and Use, International Union of PurE and Applied Chemistry, 2002, pp. 329-345, Verlag Helvetica Chimica Acta, Zurich.

* cited by examiner

USE OF AGONISTS OF FORMYL PEPTIDE RECEPTOR 2 FOR TREATING OCULAR INFLAMMATORY DISEASES

RELATED APPLICATIONS

This application claims the benefit of U.S. Provisional Patent Application Ser. No. 61/773,773 filed Mar. 6, 2013, the disclosure of which is hereby incorporated in its entirety by reference.

BACKGROUND OF THE INVENTION

1. Field of the Invention

The present invention relates to a method for treating ocular inflammatory diseases in a subject in need of such treatment, which comprises administering a pharmaceutical composition comprising a therapeutically effective amount of at least one agonist of Formyl peptide receptor 2 (FPR2).

2. Summary of the Related Art

The formyl peptide receptor (FPR) family is involved in host defense against pathogens, but also in sensing internal molecules that may provide signals of cellular dysfunction. This family includes 3 members in humans and one member of this family FPR2 (also known as FPRL-1, ALXA4) is a G protein-coupled receptor that is expressed predominantly on inflammatory cells such as monocytes and neutrophils, as well as on T cells and has been shown to play a critical role in leukocyte trafficking during inflammation and human pathology (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. *Pharmacological Reviews* 2006; 58: 463-519). FPR2 is an exceptionally promiscuous receptor that responds to a large array of exogenous and endogenous ligands, including serum amyloid A (SAA), chemokine variant sCKβ8-1, the neuroprotective peptide humanin, anti-inflammatory eicosanoid lipoxin A4 (LXA4) and glucocotricoid-modulated protein annexin A1 (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. *Pharmacological Reviews* 2006; 58: 463-519). FPR2 transduces anti-inflammatory effects of LXA4 in many systems, and has been shown to play a key role in the resolution of inflammation (Dufton N, Perretti M. Therapeutic anti-inflammatory potential of formyl peptide receptor agonists. *Pharmacology & Therapeutics* 2010; 127: 175-188). FPR2 knockout mice show exaggerated inflammation in disease conditions as expected by the biological role of the receptor (Dufton N, Hannon R, Brancaleone V, Dalli J, Patel H B, Gray M, D'Aquisto F, Buckingham J C, Perretti M, Flower R J. Anti-inflammatory role of the murine formyl-peptide receptor 2: Ligand-specific effects on leukocyte responses and experimental inflammation. *Journal of Immunology* 2010; 184: 2611-2619).

Activation of FPR2 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulate monocyte migration enabling clearance of apoptotic cells from the site of inflammation in a nonphlogistic manner (Maderna P, Cottell D C, Toivonen T, Dufton N, Dalli J, Perretti M, Godson C. FPR2/ALX receptor expression and internalization are critical for lipoxin A4 and annexin-derived peptide-stimulated phagocytosis. FASEB 2010; 24: 4240-4249; Reville K, Cream J K, Vivers S, Dransfield I, Godson C. Lipoxin A4 redistributes Myosin IIA and Cdc42 in macrophages: Implications for phagocytosis of apoptotic leukocytes. *Journal of Immunology* 2006; 176: 1878-1888). In addition, FPR2 has been shown to inhibit NK cytotoxicity and promote activation of T cells which further contributes to down regulation of tissue damaging inflammatory signals. FPR2/LXA4 interaction has been shown to be beneficial in experimental models of ischemia reperfusion, angiogenesis, ocular inflammation such as endotoxin-induced uveitis, and corneal wound healing (Serhan C. Resolution phase of inflammation: Novel endogenous anti-inflammatory and proresolving lipid mediators and pathways. *Annual reviews of Immunology* 2007; 25: 101-137; Medeiros R, Rodrigues G B, Figueiredo C P, Rodrigues E B, Grumman A Jr, Menezes-de-Lima 0 Jr, Passos G F, Calixto J B. Molecular mechanisms of topical anti-inflammatory effects of lipoxin A(4) in endotoxin-induced uveitis. *Molecular Pharmacology* 2008; 74: 154-161; Gronert K, Maheshwari N, Khan N, Hassan I R, Dunn M, Schwartzmann M L. A role for the mouse 12/15-lipoxygenase pathways in promoting epithelial wound healing and host defense. Journal of Biological Chemistry 2005; 280: 15267-15278; Leedom A, Sullivan A B, Dong B, Lau D, Gronert K. Endogenous LXA4 circuits are determinants of pathological angiogenesis in response to chronic injury. *American Journal of Pathology* 2010; 176: 74-84; Gronert K. Lipoxins in the eye and their role in wound healing. *Prostaglandins, Leukotrienes and Essential fatty Acids.* 2005; 73: 221-229). Pharmaceutical utility of lipoxin A4 and its analogs are hampered by inherent physicochemical properties of the natural poly-olefinic natural product. Therefore, small molecule anti-inflammatory agonists of FPR2 would have a wide variety of therapeutic benefit in inflammatory disorders especially in the eye. Targeting FPR2 selectively would also have benefits of reduced side effects as compared to more broad acting anti-inflammatories such as steroids or NSAIDs which have significant side effects of elevated IOP and delays in wound healing in the eye. FPR2 is also expressed in ocular tissues in the cornea and also the posterior of eye, in addition to the inflammatory cells that migrate into the ocular tissues. FPR2 thus represents an important novel pro-resolutionary molecular target for the development of new therapeutic agents in ocular diseases with excessive inflammatory responses.

BRIEF DESCRIPTION OF THE INVENTION

The invention pertains to the ability of FPR2 agonists to exhibit ocular anti-inflammatory activity with chemical stability and suitable for ocular delivery. These FPR2 compounds show good potency at the receptor, a subset of compounds is exemplified in the tables below, and importantly, the FPR2 compounds are active topically, and therefore could be administered in many forms, including but not limited to eye drops. These compounds may also be administered directly or through a local drug delivery device applied to ocular tissue, and via IV, intramuscularly, intrathecally, subcutaneously, orally, intravitreally or intraperitoneally. These compounds will be useful for the treatment of ocular inflammatory diseases including, but not limited to, uveitis, dry eye, keratitis, allergic eye disease, infectious keratitis, herpetic keratitis, corneal angiogenesis, lymphangiogenesis, uveitis, retinitis, and choroiditis such as acute multifocal placoid pigment epitheliopathy, Behcet's disease, post-surgical corneal wound healing, conditions caused by laser, conditions caused by photodynamic therapy, wet and dry age-related macular degeneration (ARMD), conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, post-surgical corneal inflammation, blepharitis, MGD, glaucoma, branch vein occlusion, Best's vitelliform macular degeneration, retinitis pigmentosa, proliferative vitreoretinopathy (PVR), and any other degenerative diseases of either the photoreceptors or the retinal pigment epithelial (RPE).

In another aspect these compounds will be useful for the treatment of ocular inflammatory diseases associated with CNS disorders such as Alzheimer's disease, arthritis, sepsis, inflammatory bowel disease, cachexia, angina pectoris, rheumatoid arthritis and related inflammatory disorders, alopecia, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus.

DETAILED DESCRIPTION OF THE INVENTION

Figure 1:
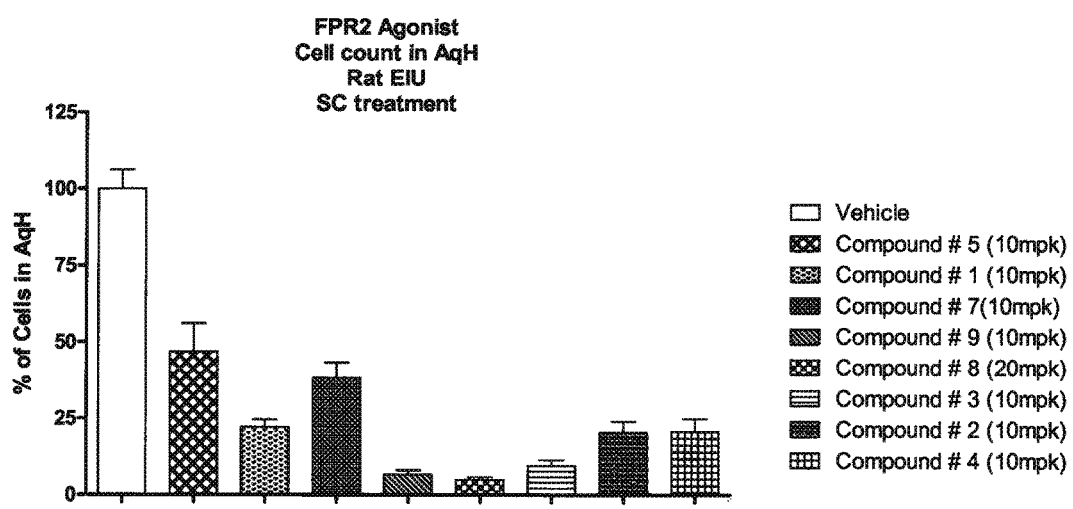
FIG. 1 FPR2 agonists show potent anti-inflammatory activity in endotoxin-induced uveitis model in rats.

The present invention relates to a method for treating ocular inflammatory diseases in a subject in need of such treatment, which comprises administering a pharmaceutical composition comprising a therapeutically effective amount of at least one agonist of FPR2.

In another aspect, the invention provides the use of at least one agonist of FPR2 for the manufacture of a medicament for the treatment of an ocular inflammatory disease or condition mediated by FPR2 in a mammal.

In another aspect, the invention provides a method for treating ocular inflammatory diseases, which comprises administering a pharmaceutical composition comprising a therapeutically effective amount of at least one agonist of FPR2 as disclosed in U.S. patent application Ser. No. 13/668,835, provided that the compounds have binding activity at the FPR2 receptor.

In another aspect, the invention provides the use of at least one compound as disclosed in U.S. patent application Ser. No. 13/668,835 for the manufacture of a medicament for the treatment of an ocular disease or condition mediated by FPR2 in a mammal, provided that the compounds have binding activity at the FPR2 receptor.

In another aspect, the invention provides the use of at least one compound as disclosed in U.S. patent application Ser. No. 13/668,835 for treating an ocular disease or condition mediated by FPR2 in a mammal, provided that the compounds have binding activity at the FPR2 receptor.

The compounds disclosed in U.S. patent application Ser. No. 13/668,835 are represented by Formula I:

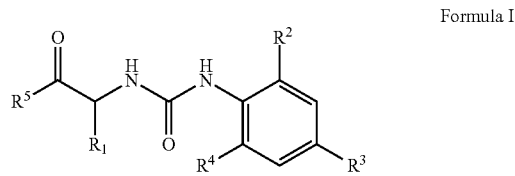

Formula I wherein:
$R^1$ is sec-butyl, $C_{6-10}$ aryl, —$CH_2$— $(C_{6-10})$aryl, —$CH_2$-heterocycle, $C_{4-8}$ cycloalkyl or $C_{3-8}$ cycloalkenyl or heterocycle;

$R^2$ is halogen or methyl;

$R^3$ is halogen;

$R^4$ is H, methyl or halogen;

$R^5$ is $OR^6$ or $NH_2$;

$R^6$ is H or $C_{2-4}$ alkyl.

In another aspect, the invention provides a method for treating ocular inflammatory diseases, which comprises administering a pharmaceutical composition, comprising a therapeutically effective amount of at least one agonist of FPR2 as disclosed in U.S. patent application Ser. No. 13/523,579, provided that the compounds have binding activity at the FPR2 receptor.

In another aspect, the invention provides the use of at least one compound as disclosed in U.S. patent application Ser. No. 13/523,579 for the manufacture of a medicament for the treatment of an ocular disease or condition mediated by FPR2 in a mammal, provided that the compounds have binding activity at the FPR2 receptor.

In another aspect, the invention provides the use of at least one compound as disclosed in U.S. patent application Ser. No. 13/523,579 for treating an ocular disease or condition mediated by FPR2 in a mammal, provided that the compounds have binding activity at the FPR2 receptor.

The compounds disclosed in U.S. patent application Ser. No. 13/523,579 are represented by Formula II:

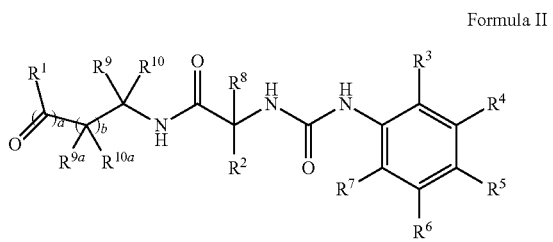

Formula II wherein:

a is 1 and b is 0;

a is 0 and b is 1;

a is 1 and b is 1;

$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, $-NR^{11}R^{12}$ or $-OR^{13}$;

$R^2$ is optionally substituted $C_{1-8}$ alkyl or optionally substituted $C_{6-10}$ aryl;

$R^3$ is hydrogen, optionally substituted $C_{1-8}$ alkyl, halogen, $-COOR^{15}$, $-OR^{13}$, $-NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^4$ is hydrogen, optionally substituted $C_{1-8}$ alkyl, halogen, $-COOR^{15}$, $-OR^{13}$, $-NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^5$ is halogen, $-CF_3$ or $-S(O)_nR^{14}$;

n is 0, 1 or 2;

$R^6$ is hydrogen, optionally substituted $C_{1-8}$ alkyl, halogen, $-COOR^{15}$, $-OR^{13}$, $-NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^7$ is hydrogen, optionally substituted $C_{1-8}$ alkyl, halogen, $-COOR^{15}$, $-OR^{13}$, $-NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^8$ is hydrogen, optionally substituted $C_{1-8}$ alkyl or optionally substituted $C_{6-10}$ aryl;

$R^9$ is hydrogen, optionally substituted $C_{1-8}$ alkyl or optionally substituted $C_{6-10}$ aryl;

$R^{10}$ is hydrogen, optionally substituted $C_{1-8}$ alkyl or optionally substituted $C_{6-10}$ aryl;

$R^{9a}$ is hydrogen, optionally substituted $C_{1-8}$ alkyl or optionally substituted $C_{6-10}$ aryl;

$R^{10a}$ is hydrogen, optionally substituted $C_{1-8}$ alkyl or optionally substituted $C_{6-10}$ aryl;

$R^{11}$ is hydrogen or optionally substituted $C_{1-8}$ alkyl;

$R^{12}$ is hydrogen or optionally substituted $C_{1-8}$ alkyl;

$R^{13}$ is hydrogen or optionally substituted $C_{1-8}$ alkyl;

$R^{14}$ is hydrogen, $CF_3$ or optionally substituted $C_{1-8}$ alkyl;

$R^{15}$ is hydrogen or optionally substituted alkyl.

In another aspect, the invention provides a method for treating ocular inflammatory diseases, which comprises administering a pharmaceutical composition, comprising a therapeutically effective amount of at least one agonist of FPR2 as disclosed in U.S. patent application Ser. No. 13/673,800, provided that the compounds have binding activity at the FPR2 receptor.

In another aspect, the invention provides the use of at least a compound as disclosed in U.S. patent application Ser. No. 13/673,800 for the manufacture of a medicament for the treatment of an ocular disease or condition mediated by FPR2 in a mammal, provided that the compounds have binding activity at the FPR2 receptor.

In another aspect, the invention provides the use of at least a compound as disclosed in U.S. patent application Ser. No. 13/673,800 for treating an ocular disease or condition mediated by FPR2 in a mammal, provided that the compounds have binding activity at the FPR2 receptor.

The compounds disclosed in U.S. patent application Ser. No. 13/673,800 are represented by Formula III:

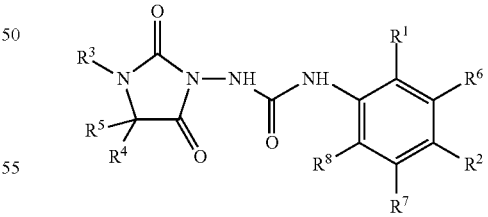

Formula III wherein:

$R^1$ is halogen, hydrogen, optionally substituted $C_{1-8}$ alkyl, $OR^9$, $C(O)R^{10}$, $NO_2$, $NR^{13}R^{14}$, $CN$, $SR^{15}$ or $SO_2R^{16}$;

$R^2$ is halogen, optionally substituted $C_{1-8}$ alkyl, $CF_3$, $OR^9$, $C(O)R^{10}$, $NO_2$, $NR^{13}R^{14}$, $CN$, $SR^{15}$ or $SO_2R^{16}$;

$R^3$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a 10- or 11-membered polycyclic ring which is optionally substituted;

$R^4$ is hydrogen, optionally substituted $C_{1-8}$ alkyl,

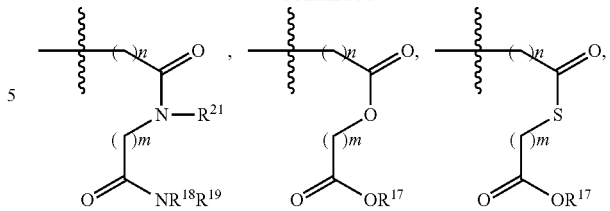
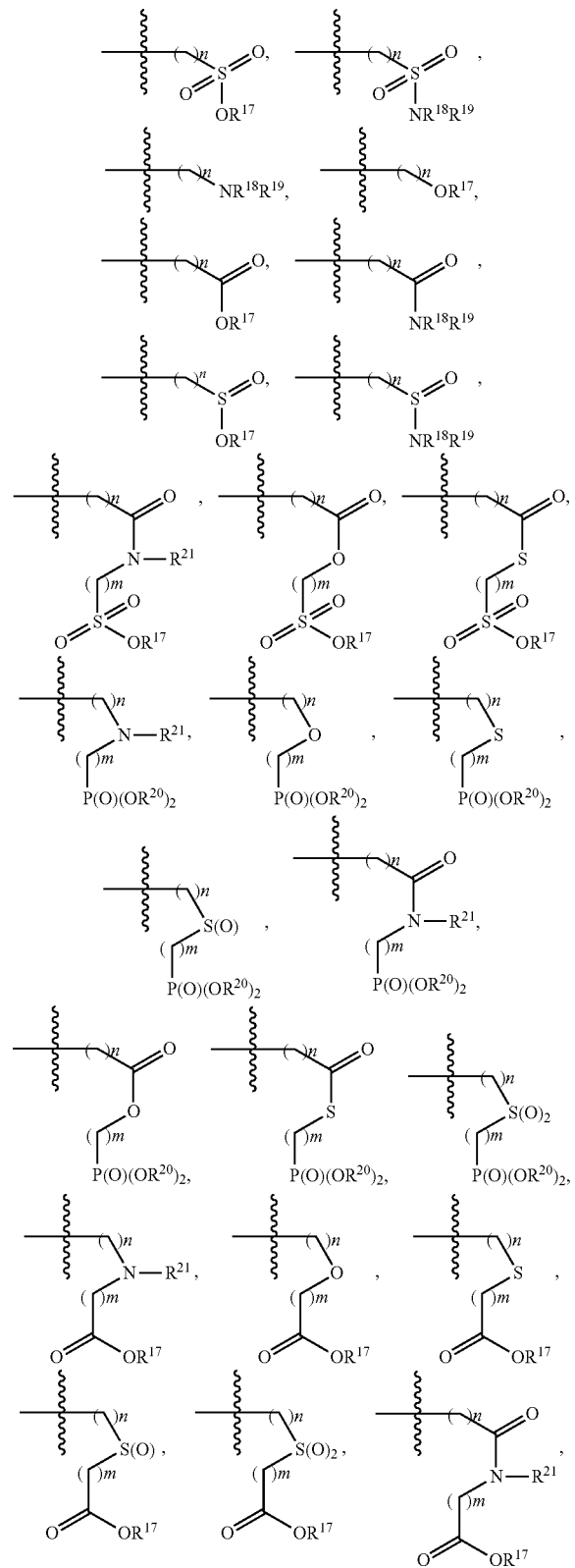

optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a spiro monocyclic or polycyclic, carbocyclic or heterocyclic, saturated or unsaturated 5 to 10 member ring which is optionally substituted;

$R^5$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^4$ forms a spiro monocyclic or polycyclic, carbocyclic or heterocyclic, saturated or unsaturated 5 to 10 member ring which is optionally substituted or together with $R^3$ forms a 5 or 6 member ring which is optionally substituted;

$R^6$ is halogen, hydrogen, optionally substituted $C_{1-8}$ alkyl, $OR^9$, $C(O)R^{10}$, $NO_2$, $NR^{13}R^{14}$, $CN$, $SR^{15}$ or $SO_2R^{16}$;

$R^7$ is halogen, hydrogen, optionally substituted $C_{1-8}$ alkyl, $OR^9$, $C(O)R^{16}$, $NO_2$, $NR^{13}R^{14}$, $CN$, $SR^{15}$ or $SO_2R^{16}$;

$R^8$ is halogen, hydrogen, optionally substituted $C_{1-8}$ alkyl, $OR^9$, $C(O)R^{10}$, $NO_2$, $NR^{13}R^{14}$, $CN$, $SR^{15}$ or $SO_2R^{16}$;

$R^9$ is hydrogen, $C(O)(C_{1-8}$ alkyl) or optionally substituted $C_{1-8}$ alkyl;

$R^{10}$ is hydrogen, optionally substituted $C_{1-8}$ alkyl, $O(C_{1-8}$ alkyl), $NR^{11}R^{12}$ or $OH$;

$R^{11}$ is hydrogen, optionally substituted $C_{6-10}$ aryl or optionally substituted $C_{1-8}$ alkyl;

$R^{12}$ is hydrogen, optionally substituted $C_{6-10}$ aryl or optionally substituted $C_{1-8}$ alkyl;

$R^{13}$ is hydrogen, optionally substituted $C_{6-10}$ aryl or optionally substituted $C_{1-8}$ alkyl;

$R^{14}$ is hydrogen, optionally substituted $C_{6-10}$ aryl, optionally substituted $C_{1-8}$ alkyl, $C(O)(C_{1-8}$ alkyl) or $SO_2(C_{1-8}$ alkyl);

$R^{15}$ is hydrogen, optionally substituted $C_{1-8}$ alkyl or $O(C_{1-8}$ alkyl);

$R^{16}$ is $OH$, $O(C_{1-8}$ alkyl), $(C_{1-8}$ alkyl) or $NR^{11}R^{12}$;

$R^{17}$ is hydrogen, optionally substituted $C_{6-10}$ aryl or optionally substituted $C_{1-8}$ alkyl;

$R^{18}$ is hydrogen, $C(O)(C_{1-8}$ alkyl), optionally substituted $C_{6-10}$ aryl, or optionally substituted $C_{1-8}$ alkyl;

$R^{19}$ is hydrogen, $C(O)(C_{1-8}$ alkyl), optionally substituted $C_{6-10}$ aryl or optionally substituted $C_{1-8}$ alkyl;

$R^{20}$ is hydrogen, optionally substituted $C_{6-10}$ aryl or optionally substituted $C_{1-8}$ alkyl;

$R^{21}$ is hydrogen, optionally substituted $C_{6-10}$ aryl or optionally substituted $C_{1-8}$ alkyl;

n is 1, 2, 3, 4, or 5; and m is 1, 2, 3, 4, or 5.

In another aspect, the invention provides a method for treating ocular inflammatory diseases, which comprises administering a pharmaceutical composition comprising a therapeutically effective amount of at least one agonist of FPR2 as disclosed in U.S. patent application Ser. No. 13/765,527, provided that the compounds have binding activity at the FPR2 receptor.

In another aspect, the invention provides the use of at least one compound as disclosed in U.S. patent application Ser. No. 13/765,527 for the manufacture of a medicament for the treatment of an ocular disease or condition mediated by FPR2 in a mammal, provided that the compounds have binding activity at the FPR2 receptor.

In another aspect, the invention provides the use of at least one compound as disclosed in U.S. patent application Ser. No. 13/765,527 for treating an ocular disease or condition mediated by FPR2 in a mammal, provided that the compounds have binding activity at the FPR2 receptor.

The compounds disclosed in U.S. patent application Ser. No. 13/765,527 are represented by Formula IV:

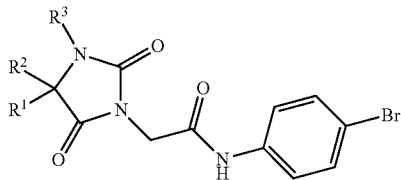

Formula IV wherein:
- $R^1$ is hydrogen, halogen, substituted or unsubstituted $C_{1-8}$ alkyl, substituted or Unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle or substituted or unsubstituted $C_{6-10}$ aryl, or together with $R^2$ can form an optionally substituted cyclobutyl;
- $R^2$ is isopropyl or together with $R^3$ can form a substituted or unsubstituted 3 to 6 member ring heterocycle or together with $R^1$ can form an optionally substituted cyclobutyl, cyclopropyl; and
- $R^3$ is hydrogen, substituted or unsubstituted $C_{1-8}$ alkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted heterocycle, substituted or unsubstituted $C_{6-10}$ aryl or together with $R^2$ can form a substituted or unsubstituted 3 to 6 member ring heterocycle.

In another aspect, the invention provides a method for treating ocular inflammatory diseases, which comprises administering a therapeutically effective amount of a pharmaceutical composition, comprising at least one agonist of FPR2 as disclosed in U.S. patent application Ser. No. 13/409,228, provided that the compounds have binding activity at the FPR2 receptor.

In another aspect, the invention provides the use of at least one compound as disclosed in U.S. patent application Ser. No. 13/409,228 for the manufacture of a medicament for the treatment of an ocular disease or condition mediated by FPR2 in a mammal, provided that the compounds have binding activity at the FPR2 receptor.

In another aspect, the invention provides the use of at least one compound as disclosed in U.S. patent application Ser. No. 13/409,228 for treating an ocular disease or condition mediated by FPR2 in a mammal, provided that the compounds have binding activity at the FPR2 receptor.

The compounds disclosed in U.S. patent application Ser. No. 13/409,228 are represented by Formula V:

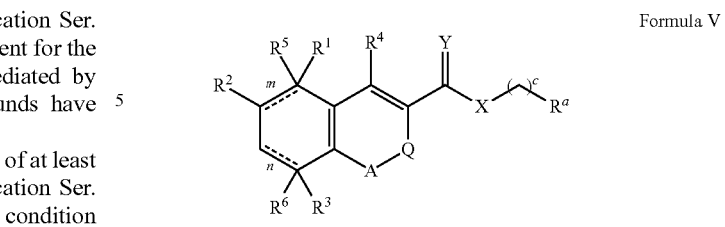

Formula V wherein:
- "$\overset{m}{\text{-----}}$" is a single bond or a double bond;
- "$\overset{n}{\text{-----}}$" is a single bond or a double bond;
- $R^1$ is H, halogen, $—S(O)R^{10}$, $—S(O)_2R^{11}$, nitro, cyano, $—OC_{1-6}$ alkyl, $—SC_{1-6}$ alkyl, $—C_{1-6}$ alkyl, $—C_{2-6}$ alkenyl, $—C_{2-6}$ alkynyl, $C(O)R^{12}$, $NR^{13}R^{14}$, $C_{3-8}$ cycloalkyl, $C_{3-8}$ cycloalkenyl or hydroxyl;
- $R^2$ is H, halogen, $—S(O)R^{10}$, $—S(O)_2R^{11}$, nitro, cyano, $—OC_{1-6}$ alkyl, $—SC_{1-6}$ alkyl, $—C_{1-6}$ alkyl, $—C_{2-6}$ alkenyl, $—C_{2-6}$ alkynyl, $C(O)R^{12}$, $NR^{13}R^{14}$, $C_{3-8}$ cycloalkyl, $C_{3-8}$ cycloalkenyl or hydroxyl;
- $R^3$ is H, halogen, $—S(O)R^{10}$, $—S(O)_2R^{11}$, nitro, cyano, $—OC_{1-6}$ alkyl, $—SC_{1-6}$ alkyl, $—C_{1-6}$ alkyl, $—C_{2-6}$ alkenyl, $—C_{2-6}$ alkynyl, $C(O)R^{12}$, $NR^{13}R^{14}$, $C_{3-8}$ cycloalkyl, $C_{3-8}$ cycloalkenyl, $C_{6-10}$ aryl or hydroxyl;
- $R^4$ is H or $C(O)R^{12}$;
- $R^5$ is H, $—OC_{1-6}$ alkyl, $—SC_{1-6}$ alkyl, $—C_{1-6}$ alkyl, $—C_{2-6}$ alkenyl or $—C_{2-6}$ alkynyl;
- $R^6$ is H, $—OC_{1-6}$ alkyl, $—SC_{1-6}$ alkyl, $—C_{1-6}$ alkyl, $—C_{2-6}$ alkenyl or $—C_{2-6}$ alkynyl;
- Y is O or S;
- X is O, NR, or $CH_2$;
- $R^a$ is $C_{6-10}$ aryl,

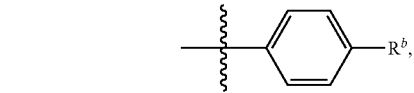

heteroaryl, $C_{3-8}$ cycloalkyl, $C_{3-8}$ cycloalkenyl or H;
- $R^b$ is halogen;
- c is 0, 1 or 2;

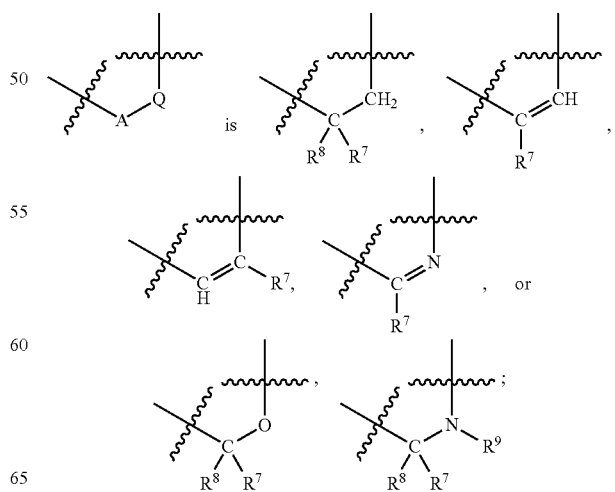

$R^7$ is H, halogen, —S(O)$R^{10}$, —S(O)$_2R^{11}$, nitro, hydroxyl, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkenyl or $C_{3-8}$ cycloalkyl;

$R^8$ is H, halogen, —S(O)$R^{10}$, —S(O)$_2R^{11}$, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkenyl or $C_{3-8}$ cycloalkyl;

$R^9$ is H, —S(O)$_2R^{11}$, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, $C_{3-8}$ cycloalkenyl or $C_{3-8}$ cycloalkyl;

$R^{10}$ is —$C_{1-6}$ alkyl, $C_{3-8}$ cycloalkyl, or $C_{3-8}$ cycloalkenyl;

$R^{11}$ is H, hydroxyl, —$C_{1-6}$ alkyl, $C_{3-8}$ cycloalkyl or $C_{3-8}$ cycloalkenyl;

$R^{12}$ is H, hydroxyl, —$C_{1-6}$ alkyl, $C_{3-8}$ cycloalkyl, $C_{3-8}$ cycloalkenyl, N$R^{13}R^{14}$ or —O$C_{1-6}$ alkyl;

$R^{13}$ is H, —$C_{1-6}$ alkyl, $C_{3-8}$ cycloalkyl, $C_{3-8}$ cycloalkenyl SO$_2R^{11}$ or C(O)$R^{15}$;

$R^{14}$ is H, —$C_{1-6}$ alkyl, $C_{3-8}$ cycloalkenyl, aryl, heterocycle or $C_{3-8}$ cycloalkyl;

$R^{15}$ is H, —$C_{1-6}$ alkyl, $C_{3-8}$ cycloalkenyl or $C_{3-8}$ cycloalkyl; and R is H, —$C_{1-6}$ alkyl, $C_{3-8}$ cycloalkenyl or $C_{3-8}$ cycloalkyl;

with the provisos:

when "---$^m$---" is a double bond then $R^5$ is void; and when "---$^n$---" is a double bond $R^6$ is void.

In another aspect, the invention provides a method for treating ocular inflammatory diseases, which comprises administering a pharmaceutical composition, comprising a therapeutically effective amount of at least one agonist of FPR2 as disclosed in U.S. patent application Ser. No. 13/370,472, provided that the compounds have binding activity at the FPR2 receptor.

In another aspect, the invention provides the use of at least one compound as disclosed in U.S. patent application Ser. No. 13/370,472 for the manufacture of a medicament for the treatment of an ocular disease or condition mediated by FPR2 in a mammal, provided that the compounds have binding activity at the FPR2 receptor.

In another aspect, the invention provides the use of at least one compound as disclosed in U.S. patent application Ser. No. 13/370,472 for treating an ocular disease or condition mediated by FPR2 in a mammal, provided that the compounds have binding activity at the FPR2 receptor.

The compounds as disclosed in U.S. patent application Ser. No. 13/370,472 are represented by Formula VI:

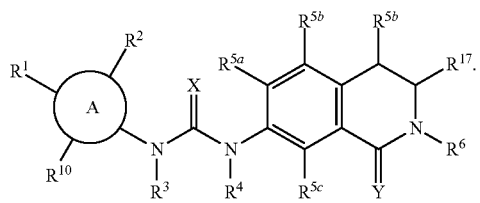

wherein:

A is $C_{6-10}$ aryl, heterocycle, $C_{3-8}$ cycloalkyl or $C_{3-8}$ cycloalkenyl;

$R^{17}$ is $C_{1-6}$ alkyl or

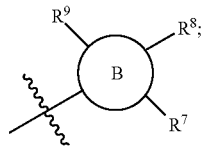

B is $C_{6-10}$ aryl, heterocyle, $C_{3-8}$ cycloalkyl or $C_{3-8}$ cycloalkenyl;

$R^1$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^2$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^3$ is H, $C_{1-6}$ alkyl or $C_{3-8}$ cycloalkyl;

$R^4$ is H, $C_{1-6}$ alkyl or $C_{3-8}$ cycloalkyl;

$R^{5a}$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^{5b}$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^{5c}$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^{5d}$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^6$ is H, —S(O)$_2R^{11}$, —$C_{1-6}$ alkyl, —(CH$_2$)$_n$N$R^{13}R^{14}$, —(CH$_2$), heterocycle, C(O)$R^{12}$, N$R^{13}R^{14}$, $C_{3-8}$ cycloalkyl, $C_{6-10}$ aryl, or heterocycle;

$R^7$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^8$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^9$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

$R^{10}$ is H, halogen, —S(O)$R^{15}$, —S(O)$_2R^{11}$, nitro, cyano, —O$C_{1-6}$ alkyl, —S$C_{1-6}$ alkyl, —$C_{1-6}$ alkyl, —$C_{2-6}$ alkenyl, —$C_{2-6}$ alkynyl, C(O)$R^{12}$, N$R^{13}R^{14}$, $C_{3-8}$ cycloalkyl or hydroxyl;

X is O or S;

Y is O or S;

$R^{11}$ is H, hydroxyl, —$C_{1-6}$ alkyl, $C_{3-8}$ cycloalkyl or N$R^{13}R^{14}$;

$R^{12}$ is H, hydroxyl, —$C_{1-6}$ alkyl, hydroxyl, $C_{3-8}$ cycloalkyl, N$R^{13}R^{14}$ or —O$C_{1-6}$ alkyl;

$R^{13}$ is H, —$C_{1-6}$ alkyl, $C_{3-8}$ cycloalkyl, SO$_2R^{11}$ or C(O)$R^{16}$;

$R^{14}$ is H, —$C_{1-6}$ alkyl or $C_{3-8}$ cycloalkyl;

$R^{15}$ is —$C_{1-6}$ alkyl, or $C_{3-8}$ cycloalkyl;

$R^{16}$ is H, —$C_{1-6}$ alkyl or $C_{3-8}$ cycloalkyl;

n is 1-4; and m is 1-4.

In another aspect, the invention provides a method for treating ocular inflammatory diseases, which comprises administering a pharmaceutical composition, comprising a therapeutically effective amount of at least one agonist of FPR2 as disclosed in U.S. patent application Ser. No. 13/863,934, provided that the compounds have binding activity at the FPR2 receptor.

In another aspect, the invention provides the use of at least one compound as disclosed in U.S. patent application Ser. No. 13/863,934 for the manufacture of a medicament for the treatment of an ocular disease or condition mediated by FPR2 in a mammal, provided that the compounds have binding activity at the FPR2 receptor.

In another aspect, the invention provides the use of at least one compound as disclosed in U.S. patent application Ser. No. 13/863,934 for treating an ocular disease or condition mediated by FPR2 in a mammal, provided that the compounds have binding activity at the FPR2 receptor.

The compounds as disclosed in U.S. patent application Ser. No. 13/863,934 are represented by Formula VII:

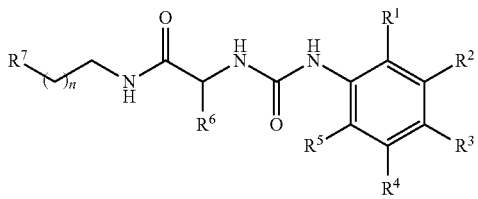

Formula VII wherein:

n is 0 or 1;

$R^1$ is hydrogen, substituted or unsubstituted $C_{1-8}$ alkyl, halogen, —$NR^8R^9$, —$NC(O)R^{20}$, —$OR^{10}$, —$OC(O)R^{21}$, —$SR^{11}$, —$C(O)R^{12}$, CN or $NO_2$;

$R^2$ is hydrogen, substituted or unsubstituted $C_{1-8}$ alkyl, halogen, —$NR^8R^9$, —$NC(O)R^{20}$, —$OR^{10}$, —$OC(O)R^{21}$—$SR^{11}$, —$C(O)R^{12}$, CN or $NO_2$;

$R^3$ is hydrogen, substituted or unsubstituted $C_{1-8}$ alkyl, halogen, —$NR^8R^9$, —$NC(O)R^{20}$, —$OR^{10}$, —$OC(O)R^{21}$, —$SR^{11}$, —$C(O)R^{12}$, CN, $NO_2$, $CF_3$, $S(O)R^{15}$ or $S(O)_2R^{16}$;

$R^4$ is hydrogen, substituted or unsubstituted $C_{1-8}$ alkyl, halogen, —$NR^8R^9$, —$NC(O)R^{20}$, —$OR^{10}$, —$OC(O)R^{21}$, —$SR^{11}$, —$C(O)R^{12}$, CN or $NO_2$;

$R^5$ is hydrogen, substituted or unsubstituted $C_{1-8}$ alkyl, halogen, —$NR^8R^9$, —$NC(O)R^{20}$, —$OR^{10}$, —$OC(O)R^{21}$, $SR^{11}$, —$C(O)R^{12}$, CN or $NO_2$;

$R^6$ is hydrogen, substituted or unsubstituted $C_{1-8}$ alkyl, substituted or unsubstituted heterocycle, substituted or unsubstituted $C_{3-8}$ cycloalkyl, substituted or unsubstituted $C_{6-10}$ aryl, substituted or unsubstituted $C_{3-8}$ cycloalkenyl or —$CH_2R^{19}$;

$R^7$ is substituted or unsubstituted heterocycle, —$SR^{11}$, —$NR^8R^9$, —$N(H)C(O)N(H)S(O)_2R^{19}$, —$BR^{13}R^{14}$, —$S(O)R^{15}$, —$C(O)N(H)(CN)$, —$C(O)N(H)S(O)_2R^{19}$, —$S(O)(N)(PO_3H_2)$—, —$S(O)_2R^{16}$ or —$P(O)R^{17}R^{18}$;

$R^8$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl;

$R^9$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl;

$R^{10}$ is hydrogen or substituted or unsubstituted $C_{1-8}$ alkyl;

$R^{11}$ is hydrogen, substituted or unsubstituted $C_{1-8}$ alkyl or —$CF_3$;

$R^{12}$ is hydrogen, substituted or unsubstituted $C_{1-8}$ alkyl, hydroxyl, —$OR^{24}$ or —$NR^8R^9$;

$R^{13}$ is —$OR^{22}$;

$R^{14}$ is —$OR^{23}$;

$R^{15}$ is substituted or unsubstituted $C_{1-8}$ alkyl;

$R^{16}$ is substituted or unsubstituted $C_{1-8}$ alkyl, —$NR^8R^9$, —$NHS(O)_2R^{19}$ or hydroxyl;

$R^{17}$ is $OR^{10}$ or $NR^8R^9$;

$R^{18}$ is $OR^{10}$ or $NR^8R^9$;

$R^{19}$ is substituted or unsubstituted heterocycle, substituted or unsubstituted $C_{3-8}$ cycloalkyl, substituted or unsubstituted $C_{6-10}$ aryl or substituted or unsubstituted $C_{3-8}$ cycloalkenyl;

$R^{20}$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl;

$R^{21}$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl;

$R^{22}$ is hydrogen, substituted or unsubstituted $C_{1-8}$ alkyl, or together with $R^{23}$ can form a cycle;

$R^{23}$ is hydrogen, substituted or unsubstituted $C_{1-8}$ alkyl, or together with $R^{22}$ can form a cycle;

$R^{24}$ is hydrogen, substituted or unsubstituted $C_{1-8}$ alkyl, substituted or unsubstituted $C_{3-8}$ cycloalkyl, substituted or unsubstituted heterocycle, or substituted or unsubstituted $C_{6-10}$ aryl.

The term "alkyl", as used herein, refers to saturated, monovalent or divalent hydrocarbon moieties having linear or branched moieties or combinations thereof and containing 1 to 8 carbon atoms. One methylene (—$CH_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$OC_{1-8}$ alkyl groups, —$SC_{1-8}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. One methylene (—$CH_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. One methylene (—$CH_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carboxylic acid groups, $C_{1-6}$ alkyl carboxylates (ester) groups, amide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —$(CO)R^x$ wherein $R^x$ can be alkyl, aryl, cycloalkyl, cycloalkenyl, heterocycle as defined above.

The term "amine" as used herein, represents a group of formula "—$NR^xR^y$", wherein $R^x$ and $R^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—$SO_2$-".

The term "sulfate" as used herein, represents a group of formula "—O—$S(O)_2$—O—".

The term "sulfonate" as used herein, represents a group of the formula "—$S(O)_2$—O—".

The term "carboxylic acid" as used herein, represents a group of formula "—C(O)ON".

The term "nitro" as used herein, represents a group of formula "—$NO_2$".

The term "cyano" as used herein, represents a group of formula "—CN".

The term "amide" as used herein, represents a group of formula "—$C(O)NR^xR^y$" wherein $R^x$ and $R^y$ can be the same or independently H, alkyl, aryl, cycloalkyl, cycloalkenyl, heterocycle as defined above.

The term "sulfonamide" as used herein, represents a group of formula "—$S(O)_2NR^xR^y$" wherein $R^x$ and $R^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—$P(O)(OH)_2$".

The term "phosphoric acid" as used herein, represents a group of formula "—$OP(O)(OH)_2$".

The term "sulphonic acid" as used herein, represents a group of formula "—$S(O)_2OH$".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

In another aspect, agonists of FPR2 are compounds selected from Table 1:

TABLE 1

| Structure | IUPAC name | FPR2 Gal 6-CHO $EC_{50}$ (efficacy) |
|---|---|---|
| 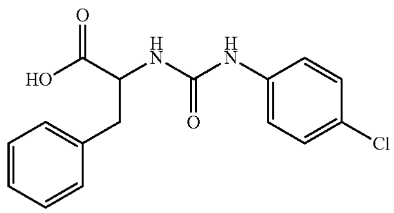 [SMILES: O=C(Nc1ccc(Cl)cc1)NC(Cc1ccccc1)C(=O)O] | 2-({[(4-chlorophenyl)amino]carbonyl}amino)-3-phenylpropanoic acid | 110 nM (1.0) |
| 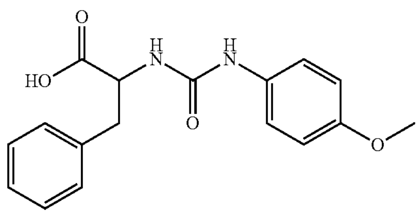 [SMILES: COc1ccc(NC(=O)NC(Cc2ccccc2)C(=O)O)cc1] | (2S)-2-({[(4-methoxyphenyl)amino]carbonyl}amino)-3-phenylpropanoic acid | 1754 nM (0.90) |
| 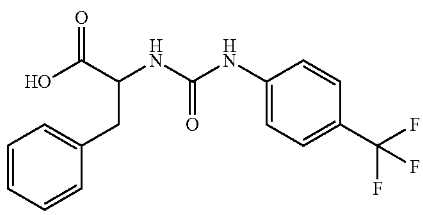 [SMILES: O=C(Nc1ccc(C(F)(F)F)cc1)NC(Cc1ccccc1)C(=O)O] | (2S)-3-phenyl-2-[({[4-(trifluoromethyl)phenyl]amino}carbonyl)amino]propanoic acid | 120 nM (0.97) |
| 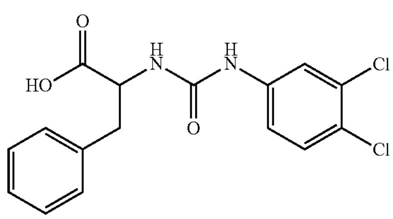 [SMILES: O=C(Nc1ccc(Cl)c(Cl)c1)NC(Cc1ccccc1)C(=O)O] | (2S)-2-({[(3,4-dichlorophenyl)amino]carbonyl}amino)-3-phenylpropanoic acid | 10 μM (0.57) |
| 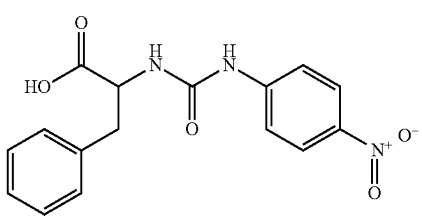 | (2S)-2-({[(4-nitrophenyl)amino]carbonyl}amino)-3-phenylpropanoic acid | 574 nM (0.82) |
| 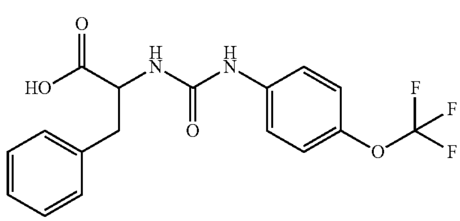 [SMILES: O=C(Nc1ccc(OC(F)(F)F)cc1)NC(Cc1ccccc1)C(=O)O] | 3-phenyl-2-[({[4-(trifluoromethoxy)phenyl]amino}carbonyl)amino]propanoic acid | 1572 nM (0.79) |
| 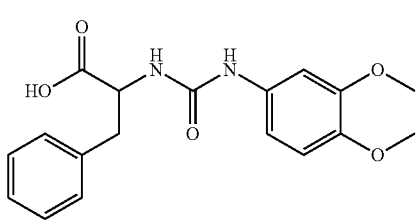 [SMILES: COc1ccc(NC(=O)NC(Cc2ccccc2)C(=O)O)cc1OC] | 2-({[(3,4-dimethoxyphenyl)amino]carbonyl}amino)-3-phenylpropanoic acid | 2793 nM (0.72) |

TABLE 1-continued

| Structure | IUPAC name | FPR2 Gal 6-CHO EC$_{50}$ (efficacy) |
|---|---|---|
| 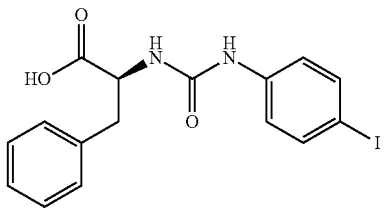 [SMILES: O=C(Nc1ccc(I)cc1)N[C@@H](Cc1ccccc1)C(=O)O] | methyl 2-({[(4-iodophenyl)amino]carbonyl}amino)-3-phenylpropanoate | 14.3 nM (1.0) |
| 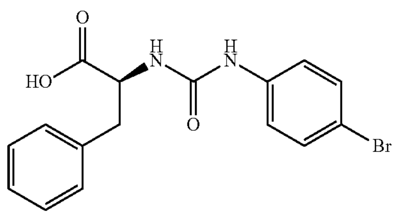 [SMILES: O=C(Nc1ccc(Br)cc1)N[C@@H](Cc1ccccc1)C(=O)O] | (2S)-2-({[(4-bromophenyl)amino]carbonyl}amino)-3-phenylpropanoic acid | 31 nM (1.0) |
| 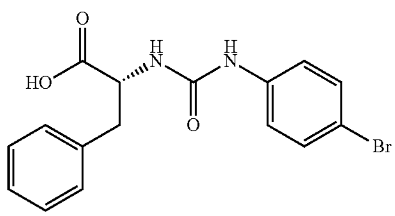 [SMILES: O=C(Nc1ccc(Br)cc1)N[C@H](Cc1ccccc1)C(=O)O] | (2R)-2-({[(4-bromophenyl)amino]carbonyl}amino)-3-phenylpropanoic acid | 1819 nM (0.99) |
|  | 3-phenyl-2-{[(pyridin-3-ylamino)carbonyl]amino}propanoic acid | >10000 nM |
| 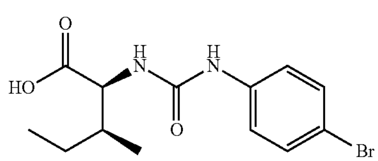 [SMILES: CC[C@H](C)[C@H](NC(=O)Nc1ccc(Br)cc1)C(=O)O] | (2S,3S)-2-({[(4-bromophenyl)amino]carbonyl}amino)-3-methylpentanoic acid | 4.1 nM (0.89) |
| 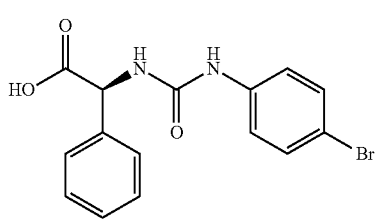 [SMILES: O=C(Nc1ccc(Br)cc1)N[C@H](C(=O)O)c1ccccc1] | (2S)-({[(4-bromophenyl)amino]carbonyl}amino)(phenyl)acetic acid | 25.8 nM (0.94) |

TABLE 1-continued

| Structure | IUPAC name | FPR2 Gal 6-CHO EC$_{50}$ (efficacy) |
|---|---|---|
| 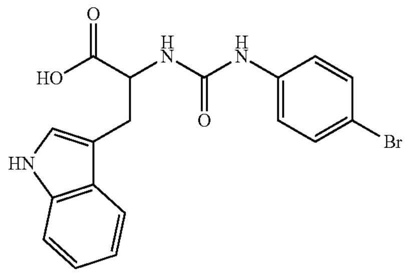 [SMILES: O=C(Nc1ccc(Br)cc1)NC(Cc1c[nH]c2ccccc12)C(=O)O] | 2-({[(4-bromophenyl)amino]carbonyl}amino)-3-(1H-indol-3-yl)propanoic acid | 67.0 nM (0.89) |
| 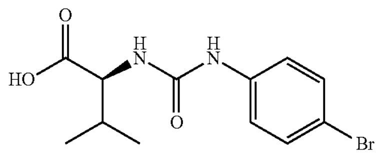 [SMILES: CC(C)[C@H](NC(=O)Nc1ccc(Br)cc1)C(=O)O] | (2S)-2-({[(4-bromophenyl)amino]carbonyl}amino)-3-methylbutanoic acid | 72 nM (0.91) |
| 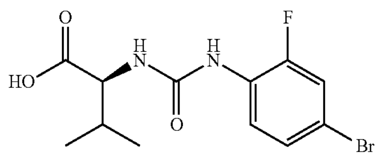 [SMILES: CC(C)[C@H](NC(=O)Nc1ccc(Br)cc1F)C(=O)O] | (2S)-2-({[(4-bromo-2-fluorophenyl)amino]carbonyl}amino)-3-methylbutanoic acid | 152 nM (0.91) |

US 2005/0137230 A1 and U.S. Pat. No. 7,820,673 disclose inhibitors of coagulation Factor Xa and can be employed for the prophylaxis and/or therapy of thromboembolic diseases and/or the treatment of tumors. 2-({[(4-chlorophenyl)amino]carbonyl}amino)-3-phenylpropanoic acid, (2S)-2-({[(4-methoxyphenyl)amino]carbonyl}amino)-3-phenylpropanoic acid, (2S)-3-phenyl-2[({[4-(trifluoromethyl)phenyl]amino}carbonyl)amino]propanoic acid, methyl 2-({[(4-iodophenyl)amino]carbonyl}amino)-3-phenylpropanoate, (2S)-2-({[(4-bromophenyl)amino]carbonyl}amino)-3-phenylpropanoic acid, (2R)-2-({[(4-bromophenyl)amino]carbonyl}amino)-3-phenylpropanoic acid, are intermediates in the synthesis of urea derivatives as activated blood coagulation factor X (FXa) inhibitors.

JP 63232846 discloses the resolution of N-(p-bromophenylcarbamyl) derivatives ((2S)-2-({[(4-bromophenyl)amino]carbonyl}amino)-3-phenylpropanoic acid, (2S,3S)-2-({[(4-bromophenyl)amino]carbonyl}amino)-3-methylpentanoic acid, 2-({[(4-bromophenyl)amino]carbonyl}amino)-3-(1H-indol-3-yl)propanoic acid, (2S)-2-({[(4-bromophenyl)amino]carbonyl}amino)-3-methylbutanoic acid) on HPLC column with novel chromatographic chiral stationary phases.

Journal of Chromatography (1987), 404(1), 117-22 and Chromatographia (1987), 23(10), 727-30 describe the resolution of p-Bromophenylcarbamyl derivatives of enantiomeric protein amino acids ((2R)-2-({[(4-bromophenyl)amino]carbonyl}amino)-3-phenylpropanoic acid, (2S)-2-({[(4-bromophenyl)amino]carbonyl}amino)-3-phenylpropanoic acid), on novel chiral stationary phase by elution with an aqueous mobile phase.

Biochimica et Biophysica Acta, Nucleic Acids and Protein Synthesis (1972), 272(4), 667-71 describes compound (2S)-2-({[(4-nitrophenyl)amino]carbonyl}amino)-3-phenylpropanoic acid) in poly(uridylic acid)-dependent binding of para nitrophenyl-carbamyl-phenylalanyl tRNA.

In another aspect, agonists of FPR2 are compounds selected from Table 2:

TABLE 2

| Structure | IUPAC name | FPR2 Gal16-CHO EC$_{50}$ (efficacy) |
|---|---|---|
| 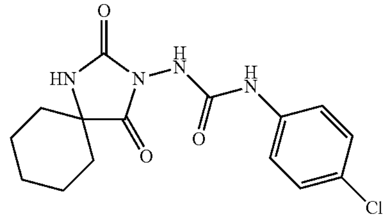 [SMILES: O=C(Nc1ccc(Cl)cc1)NN1C(=O)NC2(CCCCC2)C1=O] | 1-(4-chlorophenyl)-3-(2,4-dioxo-1,3-diazaspiro[4,5]decan-3-yl) urea | 49 nM (0.98) |

TABLE 2-continued

| Structure | IUPAC name | FPR2 Ga16-CHO EC$_{50}$ (efficacy) |
|---|---|---|
| 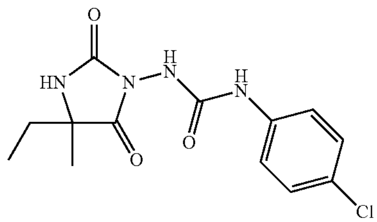 [SMILES: CCC1(C)NC(=O)N(NC(=O)Nc2ccc(Cl)cc2)C1=O] | 1-(4-chlorophenyl)-3-(4-ethyl-4-methyl-2,5-dioxoimidazolidin-1-yl)urea | 157 nm (0.96) |
| 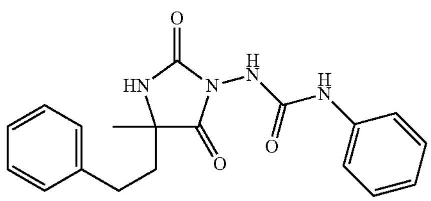 [SMILES: CC1(CCc2ccccc2)NC(=O)N(NC(=O)Nc2ccccc2)C1=O] | 1-[4-methyl-2,5-dioxo-4-(2-phenylethyl)imidazolidin-1-yl]-3-phenylurea | 223 nM (1.0) |
| 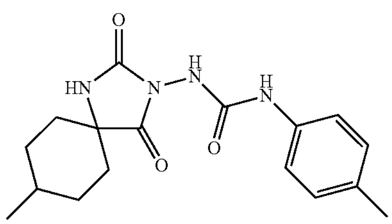 | 1-(8-methyl-2,4-dioxo-1,3-diazaspiro[4,5]decan-3-yl)-3-(p-tolyl)urea | 363 nM (0.91) |
| 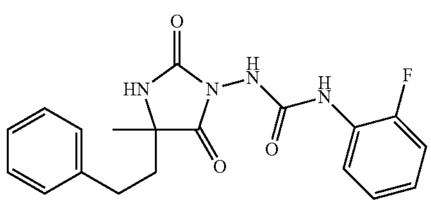 [SMILES: CC1(CCc2ccccc2)NC(=O)N(NC(=O)Nc2ccccc2F)C1=O] | 1-(2-fluorophenyl)-3-[4-methyl-2,5-dioxo-4-(2-phenylethyl)imidazolidin-1-yl]urea | 258 nM (0.94) |

Compounds of Table 2 are available from Chemical Libraries such as Aurora Fine Chemicals.

In another aspect, agonists of FPR2 are compounds selected from Table 3:

TABLE 3

| Structure | IUPAC name | FPR2 Ga16-CHO EC$_{50}$ (efficacy) |
|---|---|---|
| 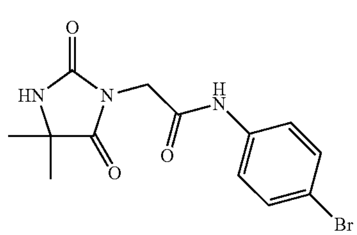 [SMILES: CC1(C)NC(=O)N(CC(=O)Nc2ccc(Br)cc2)C1=O] | N-(4-bromophenyl)-2-(4,4-dimethyl-2,5-dioxoimidazolidin-1-yl)acetamide | 719 nM (0.94) |

TABLE 3-continued

| Structure | IUPAC name | FPR2 Ga16-CHO EC$_{50}$ (efficacy) |
|---|---|---|
| 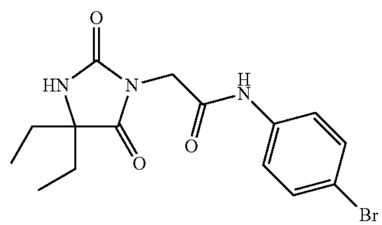 [SMILES: CCC1(CC)NC(=O)N(CC(=O)Nc2ccc(Br)cc2)C1=O] | N-(4-bromophenyl)-2-(4,4-diethyl-2,5-dioxoimidazolidin-1-yl)acetamide | 96 nM (0.98) |
| 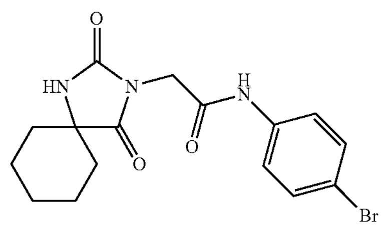 [SMILES: O=C(CN1C(=O)NC2(CCCCC2)C1=O)Nc1ccc(Br)cc1] | N-(4-bromophenyl)-2-(2,4-dioxo-1,3-diazaspiro[4.5]dec-3-yl)acetamide | 738 nM (0.89) |
| 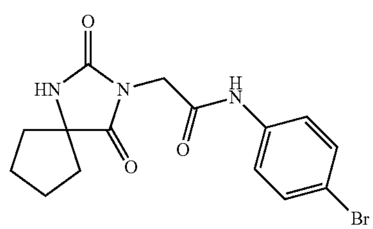 [SMILES: O=C(CN1C(=O)NC2(CCCC2)C1=O)Nc1ccc(Br)cc1] | N-(4-bromophenyl)-2-(2,4-dioxo-1,3-diazaspiro[4.4]non-3-yl)acetamide | 322 nM (0.96) |
| 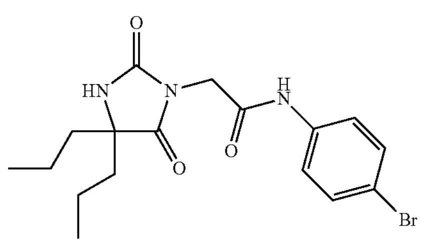 [SMILES: CCCC1(CCC)NC(=O)N(CC(=O)Nc2ccc(Br)cc2)C1=O] | N-(4-bromophenyl)-2-(2,5-dioxo-4,4-dipropylimidazolidin-1-yl)acetamide | 645 nM (0.98) |
| 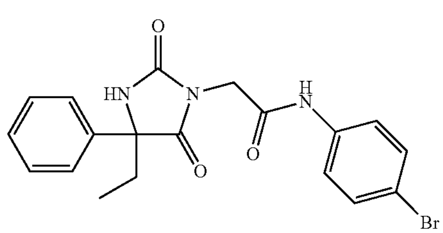 [SMILES: CCC1(c2ccccc2)NC(=O)N(CC(=O)Nc2ccc(Br)cc2)C1=O] | N-(4-bromophenyl)-2-(4-ethyl-2,5-dioxo-4-phenylimidazolidin-1-yl)acetamide | 523 nM (0.83) |
| 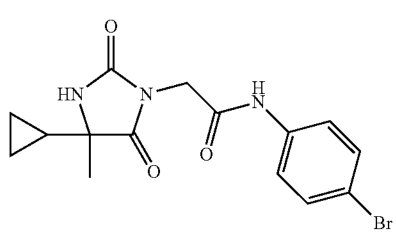 [SMILES: CC1(C2CC2)NC(=O)N(CC(=O)Nc2ccc(Br)cc2)C1=O] | N-(4-bromophenyl)-2-(4-cyclopropyl-4-methyl-2,5-dioxoimidazolidin-1-yl)acetamide | 166 nM (0.84) |

TABLE 3-continued

| Structure | IUPAC name | FPR2 Ga16-CHO EC$_{50}$ (efficacy) |
|---|---|---|
| 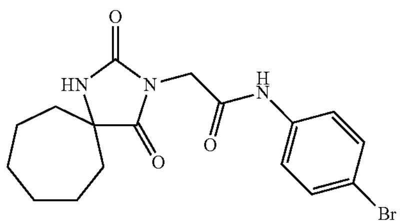 [SMILES: O=C(CN1C(=O)NC2(CCCCCC2)C1=O)Nc1ccc(Br)cc1] | N-(4-bromophenyl)-2-(2,4-dioxo-1,3-diazaspiro[4.6]undec-3-yl)acetamide | 679 nM (0.96) |
| 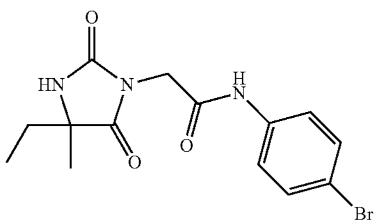 [SMILES: CCC1(C)NC(=O)N(CC(=O)Nc2ccc(Br)cc2)C1=O] | N-(4-bromophenyl)-2-(4-ethyl-4-methyl-2,5-dioxoimidazolidin-1-yl)acetamide | 485 nM (1.0) |
| 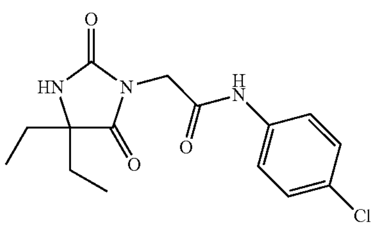 [SMILES: CCC1(CC)NC(=O)N(CC(=O)Nc2ccc(Cl)cc2)C1=O] | N-(4-chlorophenyl)-2-(4,4-diethyl-2,5-dioxoimidazolidin-1-yl)acetamide | 314 nM (0.79) |
| 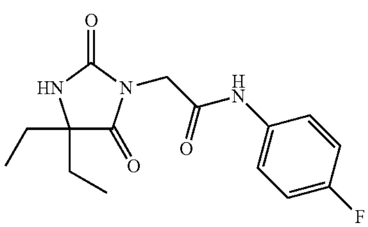 [SMILES: CCC1(CC)NC(=O)N(CC(=O)Nc2ccc(F)cc2)C1=O] | 2-(4,4-diethyl-2,5-dioxoimidazolidin-1-yl)-N-(4-fluorophenyl)acetamide | 2771 nM (0.67) |
| 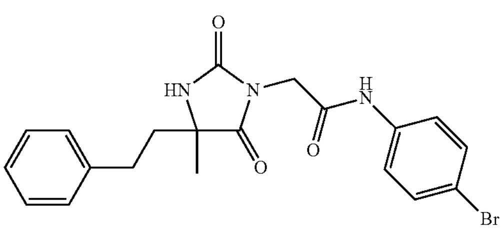 [SMILES: CC1(CCc2ccccc2)NC(=O)N(CC(=O)Nc2ccc(Br)cc2)C1=O] | N-(4-bromophenyl)-2-[4-methyl-2,5-dioxo-4-(2-phenylethyl)imidazolidin-1-yl]acetamide | 860 nM (0.88) |
| 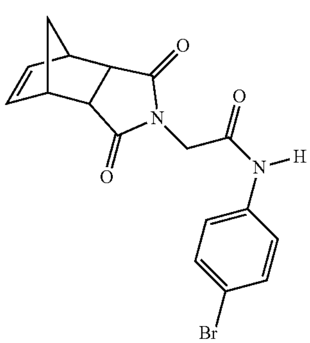 [SMILES: O=C(CN1C(=O)C2C3C=CC(C3)C2C1=O)Nc1ccc(Br)cc1] | N-(4-bromophenyl)-1,3,3a,4,7,7a-hexahydro-1,3-dioxo-4,7-methano-2H-isoindole-2-acetamide | 575 (0.90) |

TABLE 3-continued

| Structure | IUPAC name | FPR2 Gα16-CHO EC$_{50}$ (efficacy) |
|---|---|---|
| 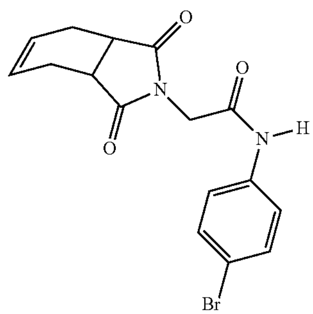 [SMILES: O=C(CN1C(=O)C2CC=CCC2C1=O)Nc1ccc(Br)cc1] | N-(4-bromophenyl)-1,3,3a,4,7,7a-hexahydro-1,3-dioxo-2H-isoindole-2-acetamide | 395 (0.98) |

The compounds of Table 3 are available from Chemical Libraries such as Chemical Block Ltd.

In a further embodiment of the invention, there are provided methods for treating disorders associated with modulation of the FPR2.

Such methods can be performed, for example, by administering to a subject in need thereof a pharmaceutical composition containing a therapeutically effective amount of at least one compound of the invention.

Therapeutic utilities of the FPR2 are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post-surgical corneal wound healing, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

These compounds are useful for the treatment of mammals, including humans, with a range of conditions and diseases that are alleviated by the modulation of FPR2: including, but not limited to the treatment of wet and dry age-related macular degeneration (ARMD), diabetic retinopathy (proliferative), retinopathy of prematurity (ROP), diabetic macular edema, uveitis, dry eye, retinal vein occlusion, cystoids macular edema, glaucoma, branch vein occlusion, Best's vitelliform macular degeneration, retinitis pigmentosa, proliferative vitreoretinopathy (PVR), and any other degenerative disease of either the photoreceptors or the RPE. In still another embodiment of the invention, there are provided methods for treating disorders associated with modulation of the FPRL-1 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereoisomers thereof.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions.

Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor. Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed. In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of FPR2. Thus, in further embodiments of the invention, there are provided methods for treating a disorder associated with modulation of FPR2. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

Materials and Methods

Figure 2:
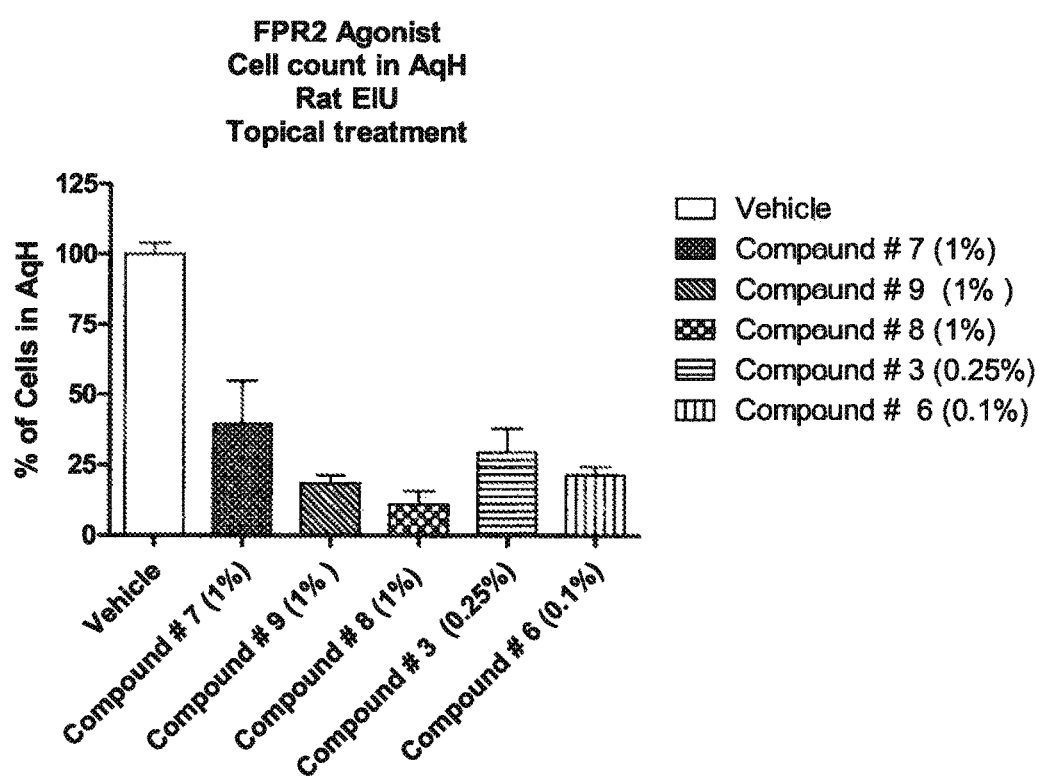
FIG. 2 FPR2 agonists show potent anti-inflammatory activity in endotoxin-induced uveitis model in rats.

FPR2 agonists would be expected to have significant effects in many different types of ocular inflammation, but have been exemplified by demonstrating anti-inflammatory activity in endotoxin-induced uveitis in rats (FIGS. 1 and 2). Anti-inflammatory activity in this model has been exemplified with the FPR2 agonists described in Table 4.

FLIPR: HEK-Gα16 cells stably expressing the human FPR2 receptor was utilized. Cells were plated into 384-well poly-D-lysine coated plates at a density of 18,000 cells per well one day prior to use. The growth media was DMEM medium supplemented with 10% fetal bovine serum (FBS), 1% antibiotic-antimycotic, 50 µg/ml hygromycin, and 400 µg/ml geneticin. On the day of the experiment, the cells were washed twice with Hank's Balanced Salt Solution supplemented with 20 mM HEPES (HBSS/hepes buffer). The cells were then dye loaded with 2 µM Fluo-4 diluted in the HBSS/Hepes buffer and incubated at 37° C. for 40 minutes. Extracellular dye was removed by washing the cell plates four times prior to placing the plates in the FLIPR (Fluorometric Imaging Plate Reader, Molecular Devices). Ligands were diluted in HBSS/Hepes buffer and prepared in 384-well microplates. Data for $Ca^{+2}$ responses were obtained in relative fluorescence units.

TABLE 4

| Compound number | Structure | IUPAC name | FPR2 EC$_{50}$ (efficacy) |
|---|---|---|---|
| 1 | 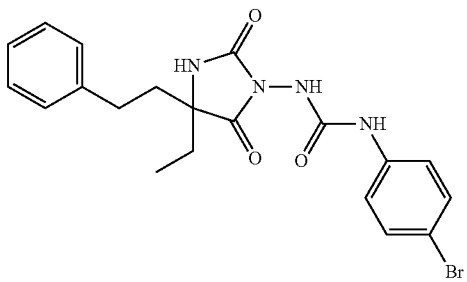 [SMILES: CCC1(CCc2ccccc2)NC(=O)N(NC(=O)Nc2ccc(Br)cc2)C1=O] | 1-(4-bromophenyl)-3-[4-ethyl-2,5-dioxo-4-(2-phenylethyl)imidazolidin-1-yl]urea | 3.0 (0.96) |
| 2 | 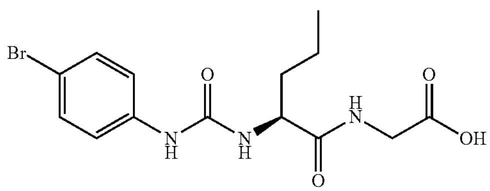 [SMILES: CCC[C@H](NC(=O)Nc1ccc(Br)cc1)C(=O)NCC(=O)O] | {[(2S)-2-{[(4-bromophenyl)carbamoyl]amino}pentanoyl]amino} acetic acid | 2 (0.91) |
| 3 | 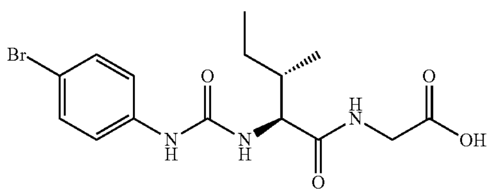 [SMILES: CC[C@H](C)[C@H](NC(=O)Nc1ccc(Br)cc1)C(=O)NCC(=O)O] | {[(2S,3S)-2-{[(4-bromophenyl)carbamoyl]amino}-3-methylpentanoyl]amino} acetic acid | 1.98 (1.0) |
| 4 | 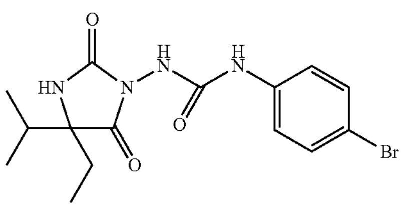 [SMILES: CCC1(C(C)C)NC(=O)N(NC(=O)Nc2ccc(Br)cc2)C1=O] | 1-(4-bromophenyl)-3-[4-ethyl-2,5-dioxo-4-(propan-2-yl)imidazolidin-1-yl]urea | 6.7 (0.90) |
| 5 | 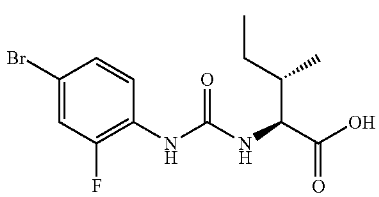 [SMILES: CC[C@H](C)[C@H](NC(=O)Nc1ccc(Br)cc1F)C(=O)O] | (2S,3S)-2-{[(4-bromo-2-fluorophenyl)carbamoyl]amino}-3-methylpentanoic acid | 31 (0.96) |
| 6 | 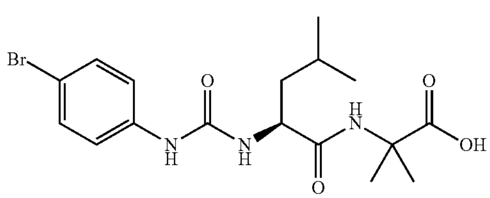 [SMILES: CC(C)C[C@H](NC(=O)Nc1ccc(Br)cc1)C(=O)NC(C)(C)C(=O)O] | 2-{[(2S)-2-{[(4-bromophenyl)carbamoyl]amino}-4-methylpentanoyl]amino}-2-methylpropanoic acid | 1.66 (0.91) |
| 7 | 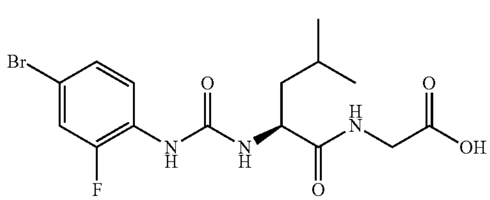 [SMILES: CC(C)C[C@H](NC(=O)Nc1ccc(Br)cc1F)C(=O)NCC(=O)O] | {[(2S)-2-{[(4-bromo-2-fluorophenyl)carbamoyl]amino}-4-methylpentanoyl]amino} acetic acid | 3.57 (1.0) |

TABLE 4-continued

| Compound number | Structure | IUPAC name | FPR2 EC$_{50}$ (efficacy) |
|---|---|---|---|
| 8 | 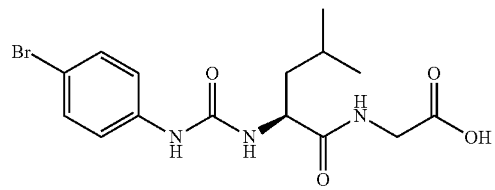 [SMILES: CC(C)C[C@H](NC(=O)Nc1ccc(Br)cc1)C(=O)NCC(=O)O] | {[(2S)-2-{[(4-bromophenyl)carbamoyl]amino}-4-methylpentanoyl]amino} acetic acid | 0.78 (0.78) |
| 9 | 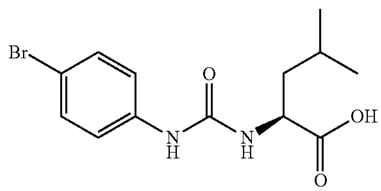 [SMILES: CC(C)C[C@H](NC(=O)Nc1ccc(Br)cc1)C(=O)O] | (2S)-2-{[(4-bromophenyl)carbamoyl]amino}-4-methylpentanoic acid | 5.95 (0.77) |
| 10 | 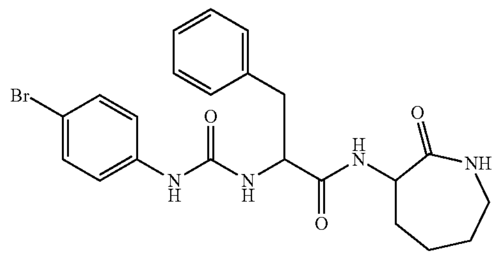 [SMILES: O=C(Nc1ccc(Br)cc1)NC(Cc1ccccc1)C(=O)NC1CCCCNC1=O] | 2-{[(4-bromophenyl)carbamoyl]amino}-N-(2-oxoazepan-3-yl)-3-phenylpropanamide | 11 nM (0.89) |
| 11 | 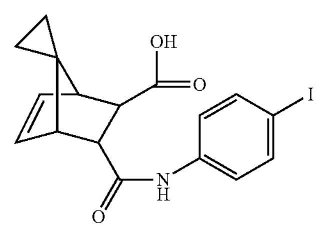 [SMILES: O=C(O)C1C(C(=O)Nc2ccc(I)cc2)C2C=CC1C21CC1] | 3-[(4-iodophenyl)carbamoyl]spiro[bicyclo[2.2.1]heptane-7,1'-cyclopropane]-5-ene-2-carboxylic acid | 1.6 nM (1.00) |
| 12 | 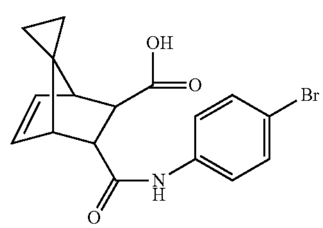 [SMILES: O=C(O)C1C(C(=O)Nc2ccc(Br)cc2)C2C=CC1C21CC1] | 3-[(4-bromophenyl)carbamoyl]spiro[bicyclo[2.2.1]heptane-7,1'-cyclopropane]-5-ene-2-carboxylic acid | 4 nM (0.97) |
| 13 | 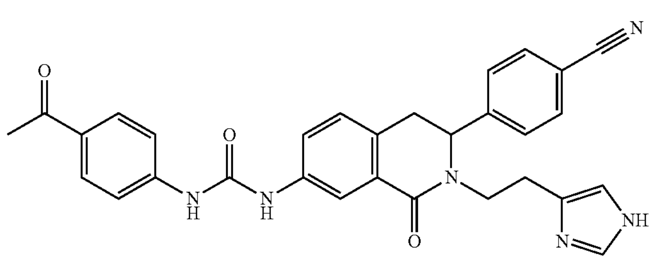 [SMILES: CC(=O)c1ccc(NC(=O)Nc2ccc3c(c2)C(=O)N(CCc2c[nH]cn2)C(c2ccc(C#N)cc2)C3)cc1] | 1-(4-acetylphenyl)-3-{3-(4-cyanophenyl)-2-[2-(1H-imidazol-4-yl)ethyl]-1-oxo-1,2,3,4-tetrahydroisoquinolin-7-yl}urea | 11 nM (0.80) |

TABLE 4-continued

| Compound number | Structure | IUPAC name | FPR2 EC$_{50}$ (efficacy) |
|---|---|---|---|
| 14 | 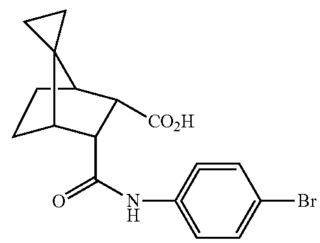 | rel-(2R,3S)-3-[(4-bromophenyl)carbamoyl]spiro[bicyclo[2.2.1]heptane-7,1'-cyclopropane]-2-carboxylic acid | 4 nM (0.90) |
| 15 | 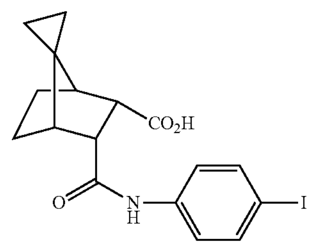 | 3-[(4-iodophenyl)carbamoyl]spiro[bicyclo[2.2.1]heptane-7,1'-cyclopropane]-2-carboxylic acid | 0.60 nM (0.87) |
| 16 | 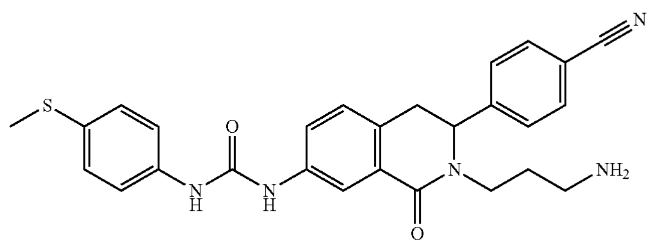 [SMILES: CSc1ccc(NC(=O)Nc2ccc3c(c2)C(=O)N(CCCN)C(c2ccc(C#N)cc2)C3)cc1] | 1-[2-(3-aminopropyl)-3-(4-cyanophenyl)-1-oxo-1,2,3,4-tetrahydroisoquinolin-7-yl]-3-[4-(methylsulfanyl)phenyl]urea | 2.5 nM (0.70) |
| 17 | 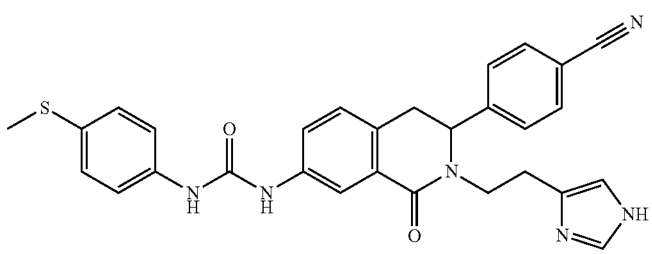 [SMILES: CSc1ccc(NC(=O)Nc2ccc3c(c2)C(=O)N(CCc2c[nH]cn2)C(c2ccc(C#N)cc2)C3)cc1] | 1-{3-(4-cyanophenyl)-2-[2-(1H-imidazol-4-yl)ethyl]-1-oxo-1,2,3,4-tetrahydroisoquinolin-7-yl}-3-[4-(methylsulfanyl)phenyl]urea | 5.5 nM (0.92) |
| 18 | 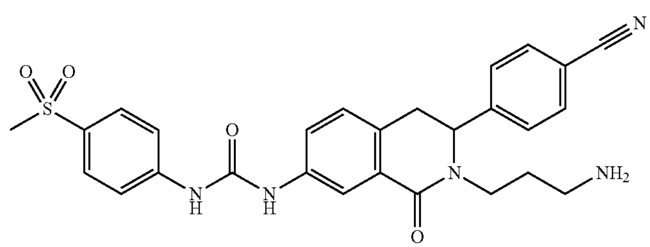 [SMILES: CS(=O)(=O)c1ccc(NC(=O)Nc2ccc3c(c2)C(=O)N(CCCN)C(c2ccc(C#N)cc2)C3)cc1] | 1-[2-(3-aminopropyl)-3-(4-cyanophenyl)-1-oxo-1,2,3,4-tetrahydroisoquinolin-7-yl]-3-[4-(methylsulfonyl)phenyl]urea | 10 nM (0.86) |
| 19 | 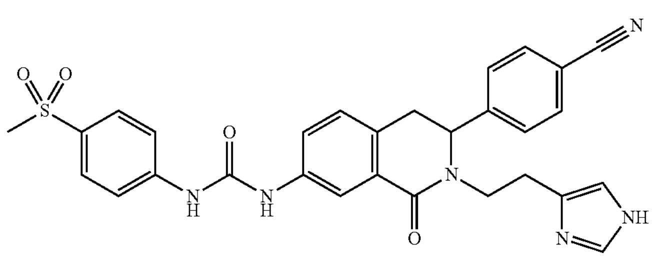 [SMILES: CS(=O)(=O)c1ccc(NC(=O)Nc2ccc3c(c2)C(=O)N(CCc2c[nH]cn2)C(c2ccc(C#N)cc2)C3)cc1] | 1-{3-(4-cyanophenyl)-2-[2-(1H-imidazol-4-yl)ethyl]-1-oxo-1,2,3,4-tetrahydroisoquinolin-7-yl}-3-[4-(methylsulfonyl)phenyl]urea | 20 nM (1.00) |

TABLE 4-continued

| Compound number | Structure | IUPAC name | FPR2 EC$_{50}$ (efficacy) |
|---|---|---|---|
| 20 | 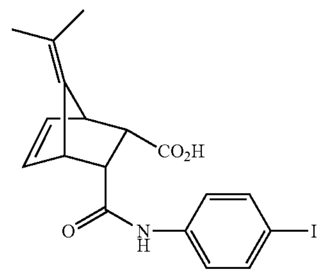 [SMILES: CC(C)=C1C2C=CC1C(C(=O)Nc1ccc(I)cc1)C2C(=O)O] | 3-[(4-iodophenyl)carbamoyl]-7-(propan-2-ylidene)bicyclo[2.2.1]hept-5-ene-2-carboxylic acid | 11 nM (0.94) |
| 21 | 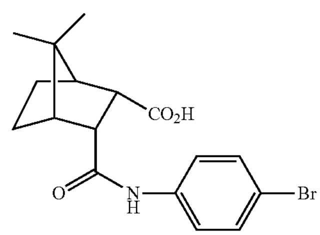 [SMILES: CC1(C)C2CCC1C(C(=O)Nc1ccc(Br)cc1)C2C(=O)O] | 3-[(4-bromophenyl)carbamoyl]-7,7-dimethylbicyclo[2.2.1]heptane-2-carboxylic acid | 10 nM (0.85) |
| 22 | 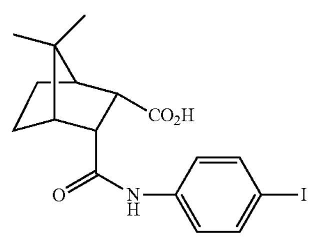 [SMILES: CC1(C)C2CCC1C(C(=O)Nc1ccc(I)cc1)C2C(=O)O] | 3-[(4-iodophenyl)carbamoyl]-7,7-dimethylbicyclo[2.2.1]heptane-2-carboxylic acid | 1.7 nM (0.97) |
| 23 | 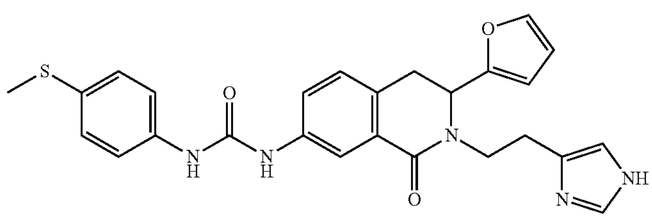 [SMILES: CSc1ccc(NC(=O)Nc2ccc3c(c2)C(=O)N(CCc2c[nH]cn2)C(c2ccco2)C3)cc1] | 1-{3-(furan-2-yl)-2-[2-(1H-imidazol-4-yl)ethyl]-1-oxo-1,2,3,4-tetrahydroisoquinolin-7-yl}-3-[4-(methylsulfanyl)phenyl]urea | 19 nM (0.83) |
| 24 | 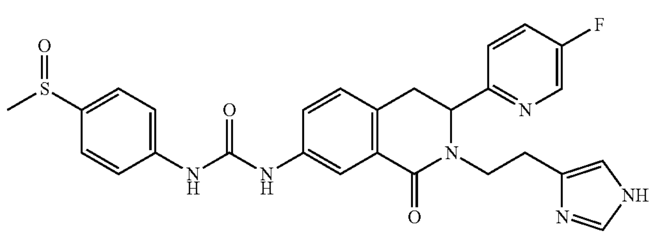 [SMILES: CS(=O)c1ccc(NC(=O)Nc2ccc3c(c2)C(=O)N(CCc2c[nH]cn2)C(c2ccc(F)cn2)C3)cc1] | 1-{3-(5-fluoropyridin-2-yl)-2-[2-(1H-imidazol-4-yl)ethyl]-1-oxo-1,2,3,4-tetrahydroisoquinolin-7-yl}-3-[4-(methylsulfinyl)phenyl]urea | 11.8 nM (0.93) |
| 25 | 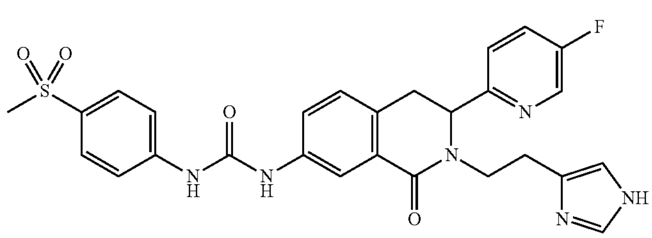 [SMILES: CS(=O)(=O)c1ccc(NC(=O)Nc2ccc3c(c2)C(=O)N(CCc2c[nH]cn2)C(c2ccc(F)cn2)C3)cc1] | 1-{3-(5-fluoropyridin-2-yl)-2-[2-(1H-imidazol-4-yl)ethyl]-1-oxo-1,2,3,4-tetrahydroisoquinolin-7-yl}-3-[4-(methylsulfonyl)phenyl]urea | 10.5 nM (1.0) |

TABLE 4-continued

| Compound number | Structure | IUPAC name | FPR2 EC$_{50}$ (efficacy) |
|---|---|---|---|
| 26 | 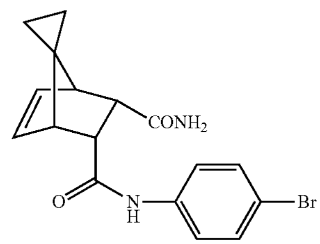 | N-(4-bromophenyl)spiro[bicyclo[2.2.1]heptane-7,1'-cyclopropane]-5-ene-2,3-dicarboxamide | 4.8 nM (0.91) |
| 27 | 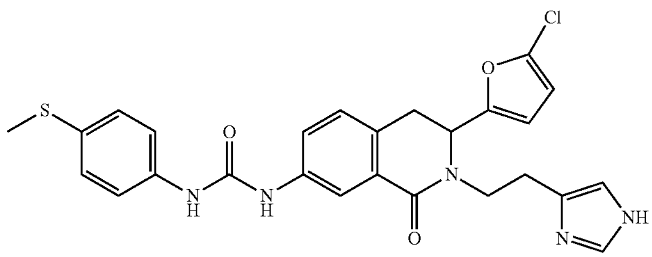 [SMILES: CSc1ccc(NC(=O)Nc2ccc3c(c2)C(=O)N(CCc2c[nH]cn2)C(c2ccc(Cl)o2)C3)cc1] | 1-{3-(5-chlorofuran-2-yl)-2-[2-(1H-imidazol-4-yl)ethyl]-1-oxo-1,2,3,4-tetrahydroisoquinolin-7-yl}-3-[4-(methylsulfanyl)phenyl]urea | 17 nM (0.81) |
| 28 | 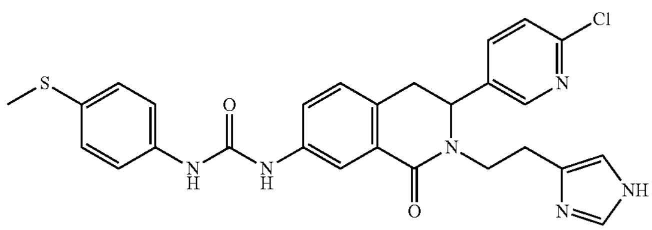 [SMILES: CSc1ccc(NC(=O)Nc2ccc3c(c2)C(=O)N(CCc2c[nH]cn2)C(c2ccc(Cl)nc2)C3)cc1] | 1-{3-(6-chloropyridin-3-yl)-2-[2-(1H-imidazol-4-yl)ethyl]-1-oxo-1,2,3,4-tetrahydroisoquinolin-7-yl}-3-[4-(methylsulfanyl)phenyl]urea | 6.3 nM (0.89) |
| 29 | 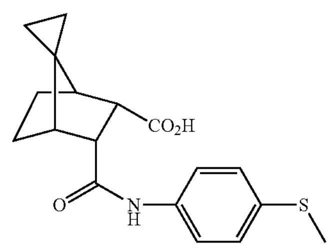 [SMILES: CSc1ccc(NC(=O)C2C(C(=O)O)C3CCC2C32CC2)cc1] | 3-{[4-(methylsulfanyl)phenyl]carbamoyl}spiro[bicyclo[2.2.1]heptane-7,1'-cyclopropane]-2-carboxylic acid | 7 nM (0.96) |
| 30 | 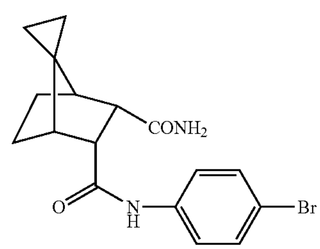 [SMILES: NC(=O)C1C(C(=O)Nc2ccc(Br)cc2)C2CCC1C21CC1] | N-(4-bromophenyl)spiro[bicyclo[2.2.1]heptane-7,1'-cyclopropane]-2,3-dicarboxamide | 2.5 nM (0.96) |
| 31 | 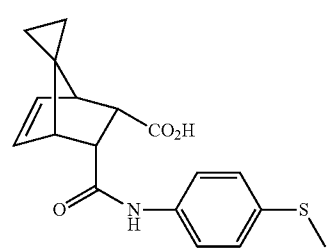 [SMILES: CSc1ccc(NC(=O)C2C(C(=O)O)C3C=CC2C32CC2)cc1] | 3-{[4-(methylsulfanyl)phenyl]carbamoyl}spiro[2.2.1]heptane-7,1'-cyclopropane]-5-ene-2-carboxylic acid | 14 nM (0.85) |

TABLE 4-continued

| Compound number | Structure | IUPAC name | FPR2 EC$_{50}$ (efficacy) |
|---|---|---|---|
| 32 | 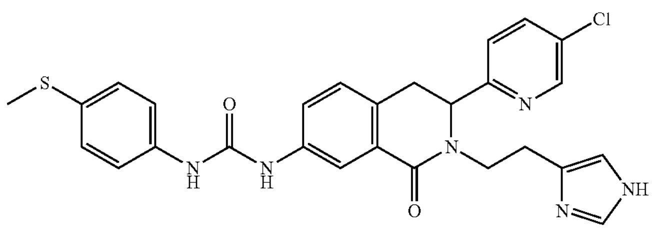 [SMILES: CSc1ccc(NC(=O)Nc2ccc3c(c2)C(=O)N(CCc2c[nH]cn2)C(c2ccc(Cl)cn2)C3)cc1] | 1-{3-(5-chloropyridin-2-yl)-2-[2-(1H-imidazol-4-yl)ethyl]-1-oxo-1,2,3,4-tetrahydroisoquinolin-7-yl}-3-[4-(methylsulfanyl)phenyl]urea | 13.5 nM (0.91) |
| 33 | 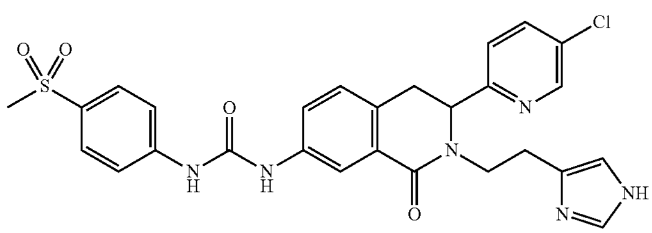 [SMILES: CS(=O)(=O)c1ccc(NC(=O)Nc2ccc3c(c2)C(=O)N(CCc2c[nH]cn2)C(c2ccc(Cl)cn2)C3)cc1] | 1-{3-(5-chloropyridin-2-yl)-2-[2-(1H-imidazol-4-yl)ethyl]-1-oxo-1,2,3,4-tetrahydroisoquinolin-7-yl}-3-[4-(methylsulfonyl)phenyl]urea | 9.5 nM (0.99) |
| 34 | 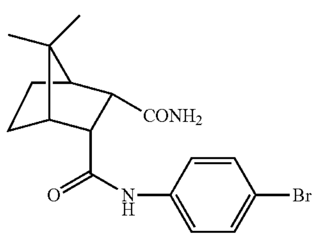 | N-(4-bromophenyl)-7,7-dimethylbicyclo[2.2.1]heptane-2,3-dicarboxamide | 15 nM (0.83) |
| 35 | 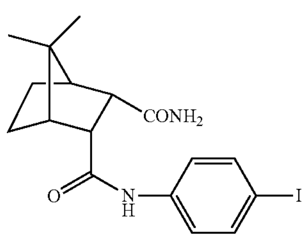 [SMILES: CC1(C)C2CCC1C(C(=O)Nc1ccc(I)cc1)C2C(N)=O] | N-(4-iodophenyl)-7,7-dimethylbicyclo[2.2.1]heptane-2,3-dicarboxamide | 2.6 nM (0.81) |
| 36 | 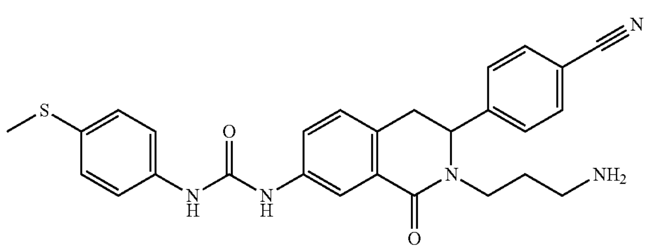 [SMILES: CSc1ccc(NC(=O)Nc2ccc3c(c2)C(=O)N(CCCN)C(c2ccc(C#N)cc2)C3)cc1] | (+) 1-[(3R)-2-(3-aminopropyl)-3-(4-cyanophenyl)-1-oxo-1,2,3,4-tetrahydroisoquinolin-7-yl]-3-[4-(methylsulfanyl)phenyl]urea | 3.3 nM (0.97) |
| 37 | 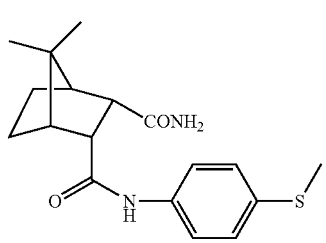 | 7,7-dimethyl-N-[4-(methylsulfanyl)phenyl]bicyclo[2.2.1]heptane-2,3-dicarboxamide | 17 nM (0.85) |

TABLE 4-continued

| Compound number | Structure | IUPAC name | FPR2 EC$_{50}$ (efficacy) |
|---|---|---|---|
| 38 | 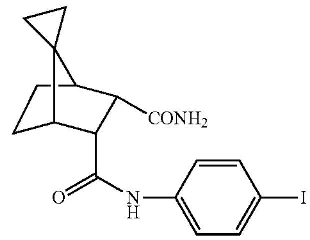 [SMILES: NC(=O)C1C(C(=O)Nc2ccc(I)cc2)C2CCC1C21CC1] | N-(4-iodophenyl)spiro[bicyclo[2.2.1]heptane-7,1'-cyclopropane]-2,3-dicarboxamide | 1.9 nM (0.95) |
| 39 | 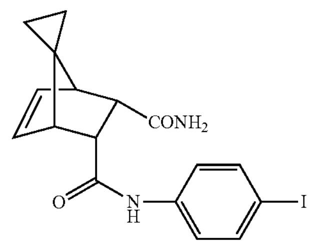 [SMILES: NC(=O)C1C(C(=O)Nc2ccc(I)cc2)C2C=CC1C21CC1] | N-(4-iodophenyl)spiro[bicyclo[2.2.1]heptane-7,1'-cyclopropane]-5-ene-2,3-dicarboxamide | 1.6 nM (0.90) |
| 40 | 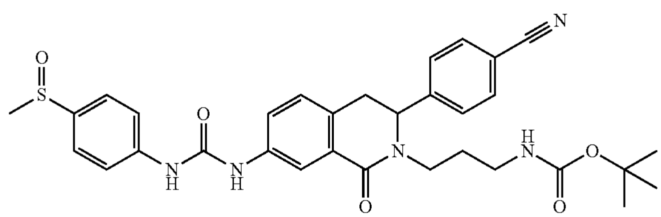 [SMILES: CS(=O)c1ccc(NC(=O)Nc2ccc3c(c2)C(=O)N(CCCNC(=O)OC(C)(C)C)C(c2ccc(C#N)cc2)C3)cc1] | (+) tert-butyl {3-[(3R)-3-(4-cyanophenyl)-7-({[4-(methylsulfinyl)phenyl]carbamoyl}amino)-1-oxo-3,4-dihydroisoquinolin-2(1H)-yl]propyl}carbamate | 103 nM (0.91) |
| 41 | 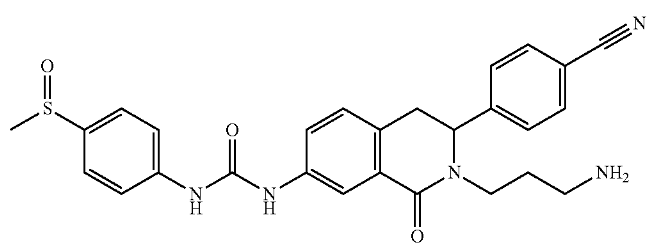 [SMILES: CS(=O)c1ccc(NC(=O)Nc2ccc3c(c2)C(=O)N(CCCN)C(c2ccc(C#N)cc2)C3)cc1] | (+) 1-[(3R)-2-(3-aminopropyl)-3-(4-cyanophenyl)-1-oxo-1,2,3,4-tetrahydroisoquinolin-7-yl]-3-[4-(methylsulfinyl)phenyl]urea | 10.6 nM (0.94) |
| 42 | 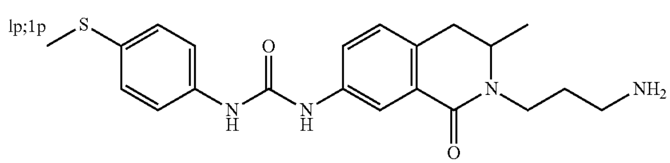 | 1-[2-(3-aminopropyl)-3-methyl-1-oxo-1,2,3,4-tetrahydroisoquinolin-7-yl]-3-[4-(methylsulfanyl)phenyl]urea | 15 nM (1.00) |
| 43 | 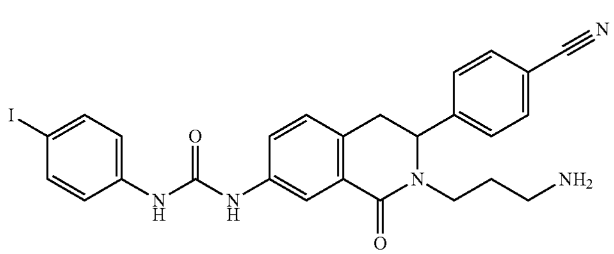 [SMILES: N#Cc1ccc(C2Cc3ccc(NC(=O)Nc4ccc(I)cc4)cc3C(=O)N2CCCN)cc1] | 1-[2-(3-aminopropyl)-3-(4-cyanophenyl)-1-oxo-1,2,3,4-tetrahydroisoquinolin-7-yl]-3-(4-iodophenyl)urea | 13.7 nM (0.94) |

TABLE 4-continued

| Compound number | Structure | IUPAC name | FPR2 EC$_{50}$ (efficacy) |
|---|---|---|---|
| 44 | 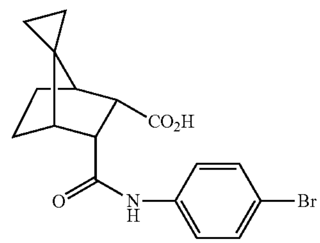 [SMILES: O=C(O)C1C(C(=O)Nc2ccc(Br)cc2)C2CCC1C21CC1] | (+) (2S,3R)-3-[(4-bromophenyl)carbamoyl]spiro[bicyclo[2.2.1]heptane-7,1'-cyclopropane]-2-carboxylic acid | <1 nM (0.98) |
| 45 | 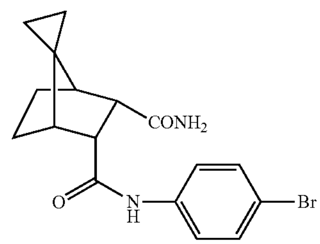 [SMILES: NC(=O)C1C(C(=O)Nc2ccc(Br)cc2)C2CCC1C21CC1] | (−) N-(4-bromophenyl)spiro[bicyclo[2.2.1]heptane-7,1'-cyclopropane]-2,3-dicarboxamide | <1 nM (0.91) |
| 46 | 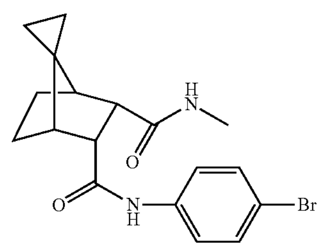 [SMILES: CNC(=O)C1C(C(=O)Nc2ccc(Br)cc2)C2CCC1C21CC1] | N-(4-bromophenyl)-N'-methylspiro[bicyclo[2.2.1]heptane-7,1'-cyclopropane]-2,3-dicarboxamide | 8.5 nM (1.0) |
| 47 | 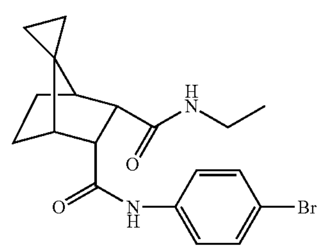 [SMILES: CCNC(=O)C1C(C(=O)Nc2ccc(Br)cc2)C2CCC1C21CC1] | N-(4-bromophenyl)-N'-ethylspiro[bicyclo[2.2.1]heptane-7,1'-cyclopropane]-2,3-dicarboxamide | 9.3 nM (1.0) |
| 48 | 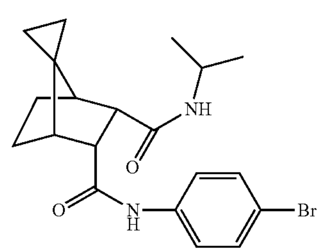 [SMILES: CC(C)NC(=O)C1C(C(=O)Nc2ccc(Br)cc2)C2CCC1C21CC1] | N-(4-bromophenyl)-N'-(propan-2-yl)spiro[bicyclo[2.2.1]heptane-7,1'-cyclopropane]-2,3-dicarboxamide | 6.7 nM (1.0) |
| 49 | 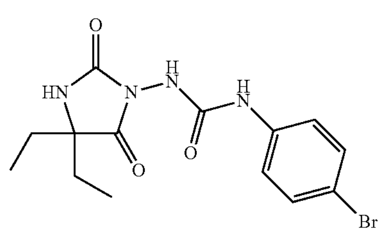 [SMILES: CCC1(CC)NC(=O)N(NC(=O)Nc2ccc(Br)cc2)C1=O] | 1-(4-bromophenyl)-3-(4,4-diethyl-2,5-dioxoimidazolidin-1-yl)urea | 11.5 nM (0.98) |

TABLE 4-continued

| Compound number | Structure | IUPAC name | FPR2 EC$_{50}$ (efficacy) |
|---|---|---|---|
| 50 | 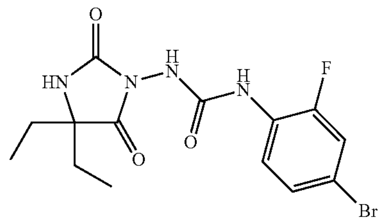 [SMILES: CCC1(CC)NC(=O)N(NC(=O)Nc2ccc(Br)cc2F)C1=O] | 1-(4-bromo-2-fluorophenyl)-3-(4,4-diethyl-2,5-dioxoimidazolidin-1-yl)urea | 15.7 nM (1.0) |
| 51 | 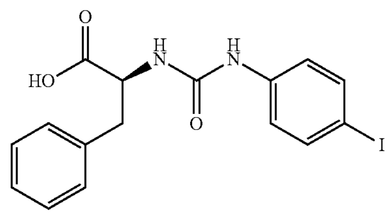 [SMILES: O=C(Nc1ccc(I)cc1)N[C@@H](Cc1ccccc1)C(=O)O] | (2S)-2-{[(4-iodophenyl)carbamoyl]amino}-3-phenylpropanoic acid | 14.5 nM (1.0) |
| 52 | 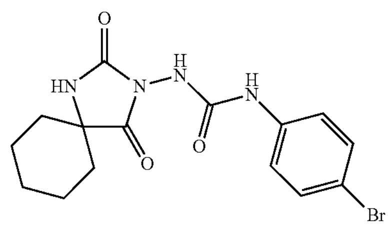 [SMILES: O=C(Nc1ccc(Br)cc1)NN1C(=O)NC2(CCCCC2)C1=O] | 1-(4-bromophenyl)-3-(2,4-dioxo-1,3-diazaspiro[4.5]dec-3-yl)urea | 15.1 nM (1.0) |
| 53 | 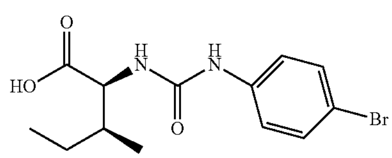 [SMILES: CC[C@H](C)[C@H](NC(=O)Nc1ccc(Br)cc1)C(=O)O] | (2S,3S)-2-{[(4-bromophenyl)carbamoyl]amino}-3-methylpentanoic acid | 12.9 nM (0.9) |
| 54 | 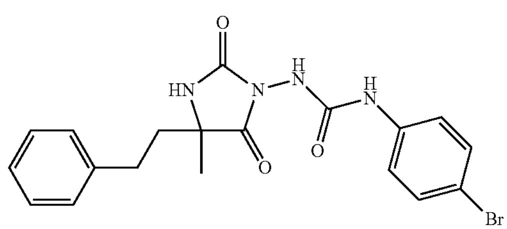 [SMILES: CC1(CCc2ccccc2)NC(=O)N(NC(=O)Nc2ccc(Br)cc2)C1=O] | 1-(4-bromophenyl)-3-[4-methyl-2,5-dioxo-4-(2-phenylethyl)imidazolidin-1-yl]urea | 5.1 nM (0.87) |
| 55 | 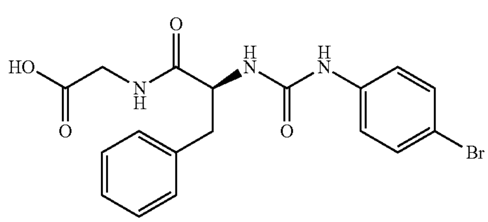 [SMILES: O=C(O)CNC(=O)[C@H](Cc1ccccc1)NC(=O)Nc1ccc(Br)cc1] | {[(2S)-2-{[(4-bromophenyl)carbamoyl]amino}-3-phenylpropanoyl]amino}acetic acid | 7.7 nM (0.99) |
| 56 | 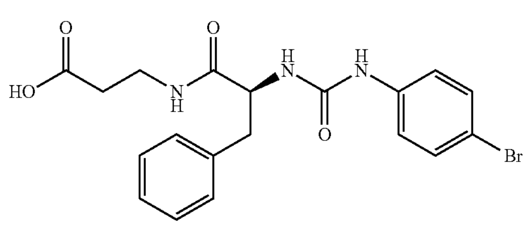 [SMILES: O=C(O)CCNC(=O)[C@H](Cc1ccccc1)NC(=O)Nc1ccc(Br)cc1] | 3-{[(2S)-2-{[(4-bromophenyl)carbamoyl]amino}-3-phenylpropanoyl]amino}propanoic acid | 18 nM (0.98) |

TABLE 4-continued

| Compound number | Structure | IUPAC name | FPR2 EC$_{50}$ (efficacy) |
|---|---|---|---|
| 57 | 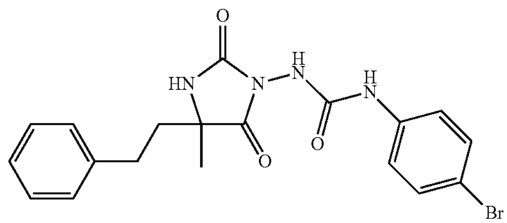 [SMILES: CC1(CCc2ccccc2)NC(=O)N(NC(=O)Nc2ccc(Br)cc2)C1=O] | (+) 1-(4-bromophenyl)-3-[4-methyl-2,5-dioxo-4-(2-phenylethyl)imidazolidin-1-yl]urea | 3.2 nM (0.93) |
| 58 | 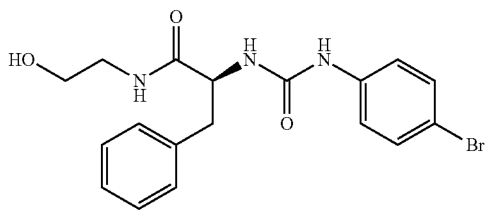 [SMILES: O=C(Nc1ccc(Br)cc1)N[C@@H](Cc1ccccc1)C(=O)NCCO] | (2S)-2-{[(4-bromophenyl)carbamoyl]amino}-N-(2-hydroxyethyl)-3-phenylpropanamide | 7.0 nM (0.86) |
| 59 | 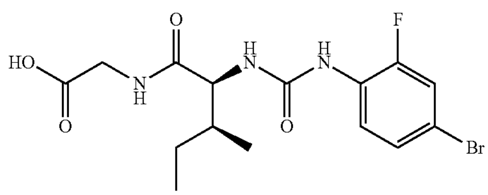 [SMILES: CC[C@H](C)[C@H](NC(=O)Nc1ccc(Br)cc1F)C(=O)NCC(=O)O] | {[(2S,3S)-2-{[(4-bromo-2-fluorophenyl)carbamoyl]amino}-3-methylpentanoyl]amino} acetic acid | 5.5 nM (0.95) |
| 60 | 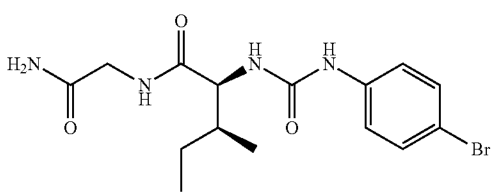 [SMILES: CC[C@H](C)[C@H](NC(=O)Nc1ccc(Br)cc1)C(=O)NCC(N)=O] | (2S,3S)-N-(2-amino-2-oxoethyl)-2-{[4-bromophenyl)carbamoyl]amino}-3-methylpentanamide | 4.6 nM (0.91) |
| 61 | 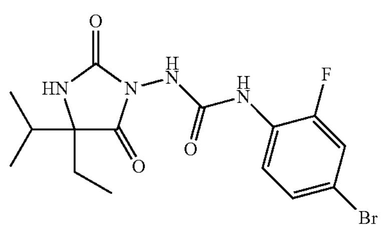 [SMILES: CCC1(C(C)C)NC(=O)N(NC(=O)Nc2ccc(Br)cc2F)C1=O] | 1-(4-bromo-2-fluorophenyl)-3-[4-ethyl-2,5-dioxo-4-(propan-2-yl)imidazolidin-1-yl]urea | 9.2 nM (0.97) |
| 62 | 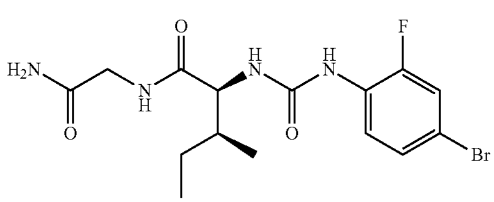 [SMILES: CC[C@H](C)[C@H](NC(=O)Nc1ccc(Br)cc1F)C(=O)NCC(N)=O] | (2S,3S)-N-(2-amino-2-oxoethyl)-2-{[(4-bromo-2-fluorophenyl)carbamoyl]amino}-3-methylpentanamide | 10.3 nM (1.0) |
| 63 | 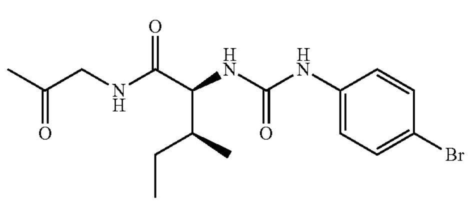 [SMILES: CC[C@H](C)[C@H](NC(=O)Nc1ccc(Br)cc1)C(=O)NCC(C)=O] | (2S,3S)-2-{[(4-bromophenyl)carbamoyl]amino}-3-methyl-N-(2-oxopropyl)pentanamide | 10.5 nM (0.97) |

TABLE 4-continued

| Compound number | Structure | IUPAC name | FPR2 EC$_{50}$ (efficacy) |
|---|---|---|---|
| 64 | 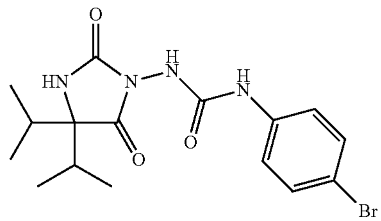 [SMILES: CC(C)C1(C(C)C)NC(=O)N(NC(=O)Nc2ccc(Br)cc2)C1=O] | 1-(4-bromophenyl)-3-[2,5-dioxo-4,4-di(propan-2-yl)imidazolidin-1-yl]urea | 3.8 nM (1.0) |
| 65 | 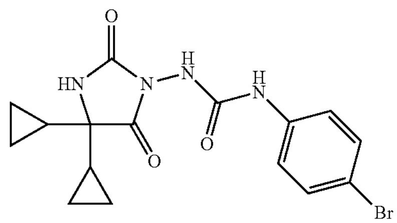 [SMILES: O=C(Nc1ccc(Br)cc1)NN1C(=O)NC(C2CC2)(C2CC2)C1=O] | 1-(4-bromophenyl)-3-(4,4-dicyclopropyl-2,5-dioxoimidazolidin-1-yl)urea | 14.3 nM (1.0) |
| 66 | 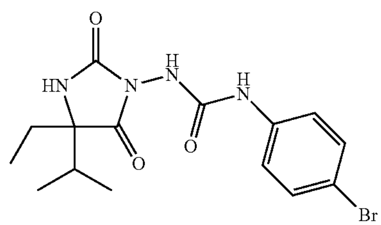 [SMILES: CCC1(C(C)C)NC(=O)N(NC(=O)Nc2ccc(Br)cc2)C1=O] | (+) 1-(4-bromophenyl)-3-[4-ethyl-2,5-dioxo-4-(propan-2-yl)imidazolidin-1-yl]urea | 4.3 nM (0.96) |
| 67 | 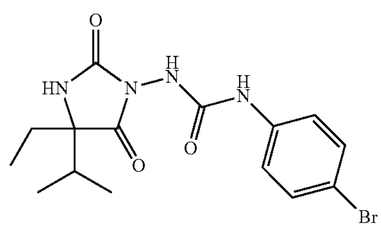 [SMILES: CCC1(C(C)C)NC(=O)N(NC(=O)Nc2ccc(Br)cc2)C1=O] | (−) 1-(4-bromophenyl)-3-[4-ethyl-2,5-dioxo-4-(propan-2-yl)imidazolidin-1-yl]urea | 3.3 nM (1.0) |
| 68 | 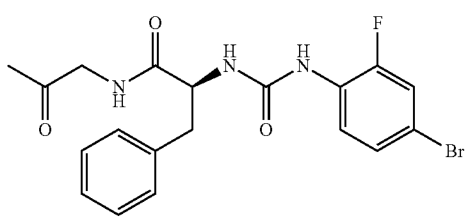 [SMILES: CC(=O)CNC(=O)[C@H](Cc1ccccc1)NC(=O)Nc1ccc(Br)cc1F] | (2S)-2-{[(4-bromo-2-fluorophenyl)carbamoyl]amino}-N-(2-oxopropyl)-3-phenylpropanamide | 12.4 nM (0.94) |
| 69 | 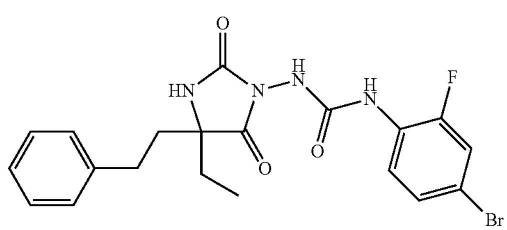 [SMILES: CCC1(CCc2ccccc2)NC(=O)N(NC(=O)Nc2ccc(Br)cc2F)C1=O] | 1-(4-bromo-2-fluorophenyl)-3-[4-ethyl-2,5-dioxo-4-(2-phenylethyl)imidazolidin-1-yl]urea | 13.4 nM (0.91) |
| 70 | 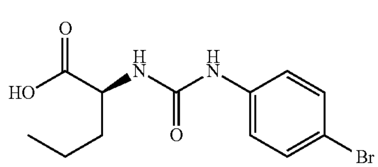 [SMILES: CCC[C@H](NC(=O)Nc1ccc(Br)cc1)C(=O)O] | (2S)-2-{[(4-bromophenyl)carbamoyl]amino}pentanoic acid | 7.1 nM (1.0) |

TABLE 4-continued

| Compound number | Structure | IUPAC name | FPR2 EC$_{50}$ (efficacy) |
|---|---|---|---|
| 71 | 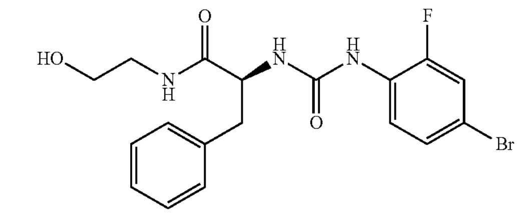 [SMILES: O=C(Nc1ccc(Br)cc1F)N[C@@H](Cc1ccccc1)C(=O)NCCO] | (2S)-2-{[(4-bromo-2-fluorophenyl)carbamoyl]amino}-N-(2-hydroxyethyl)-3-phenylpropanamide | 15.6 nM (0.98) |
| 72 | 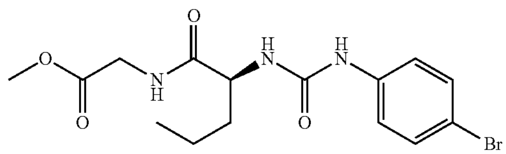 [SMILES: CCC[C@H](NC(=O)Nc1ccc(Br)cc1)C(=O)NCC(=O)OC] | methyl {[(2S)-2-{[(4-bromophenyl)carbamoyl]amino}pentanoyl]amino}acetate | 16.4 nM (0.86) |
| 73 | 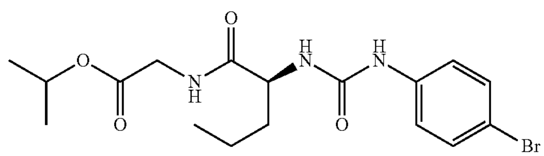 [SMILES: CCC[C@H](NC(=O)Nc1ccc(Br)cc1)C(=O)NCC(=O)OC(C)C] | propan-2-yl {[(2S)-2-{[(4-bromophenyl)carbamoyl]amino}pentanoyl]amino}acetate | 14.5 nM (1.0) |
| 74 | 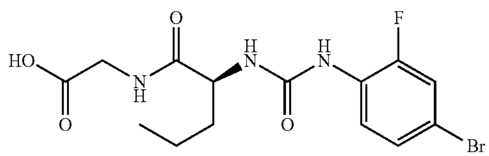 [SMILES: CCC[C@H](NC(=O)Nc1ccc(Br)cc1F)C(=O)NCC(=O)O] | {[(2S)-2-{[(4-bromo-2-fluorophenyl)carbamoyl]amino}pentanoyl]amino}acetate acid | 4.1 nM (0.91) |
| 75 | 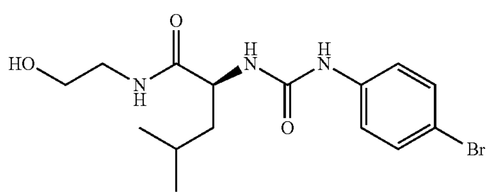 [SMILES: CC(C)C[C@H](NC(=O)Nc1ccc(Br)cc1)C(=O)NCCO] | (2S)-2-{[(4-bromophenyl)carbamoyl]amino}-N-(2-hydroxyethyl)-4-methylpentanamide | 13.5 nM (0.76) |
| 76 | 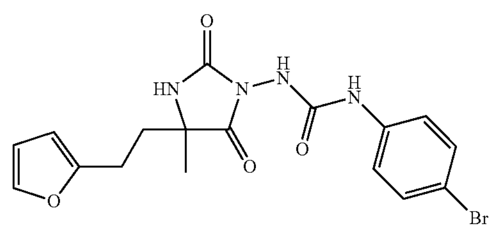 | 1-(4-bromophenyl)-3-{4-[2-(furan-2-yl)ethyl]-4-methyl-2,5-dioxoimidazolidin-1-yl}urea | 5.2 nM (0.99) |
| 77 | 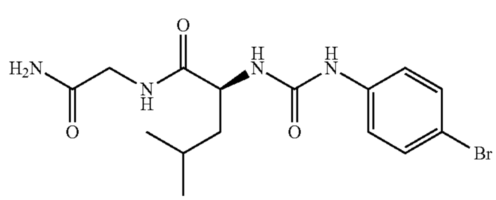 [SMILES: CC(C)C[C@H](NC(=O)Nc1ccc(Br)cc1)C(=O)NCC(N)=O] | (2S)-N-(2-amino-2-oxoethyl)-2-{[(4-bromophenyl)carbamoyl]amino}-4-methylpentanamide | 1.1 nM (1.0) |
| 78 | 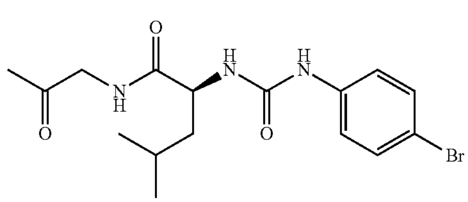 [SMILES: CC(=O)CNC(=O)[C@H](CC(C)C)NC(=O)Nc1ccc(Br)cc1] | (2S)-2-{[(4-bromophenyl)carbamoyl]amino}-4-methyl-N-(2-oxopropyl)pentanamide | 4.7 nM (0.82) |

TABLE 4-continued

| Compound number | Structure | IUPAC name | FPR2 EC$_{50}$ (efficacy) |
|---|---|---|---|
| 79 | 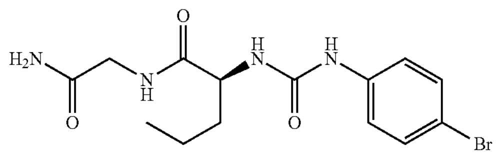 [SMILES: CCC[C@H](NC(=O)Nc1ccc(Br)cc1)C(=O)NCC(N)=O] | (2S)-N-(2-amino-2-oxoethyl)-2-{[(4-bromophenyl)carbamoyl]amino}pentanamide | 2.5 nM (0.97) |
| 80 | 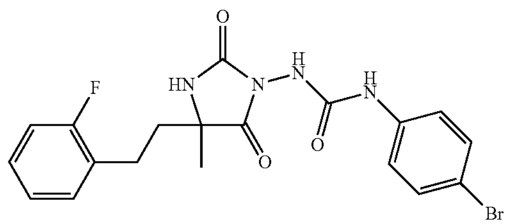 [SMILES: CC1(CCc2ccccc2F)NC(=O)N(NC(=O)Nc2ccc(Br)cc2)C1=O] | 1-(4-bromophenyl)-3-{4-[2-(2-fluorophenyl)ethyl]-4-methyl-2,5-dioxoimidazolidin-1-yl}urea | 14.3 nM (99) |
| 81 | 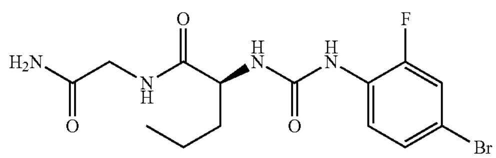 [SMILES: CCC[C@H](NC(=O)Nc1ccc(Br)cc1F)C(=O)NCC(N)=O] | (2S)-N-(2-amino-2-oxoethyl)-2-{[(4-bromo-2-fluorophenyl)carbamoyl]amino}pentanamide | 5.2 nM (0.96) |
| 82 | 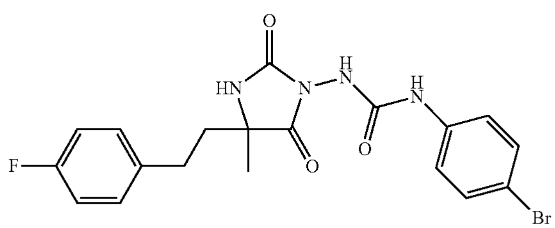 [SMILES: CC1(CCc2ccc(F)cc2)NC(=O)N(NC(=O)Nc2ccc(Br)cc2)C1=O] | 1-(4-bromophenyl)-3-{4-[2-(4-fluorophenyl)ethyl]-4-methyl-2,5-dioxoimidazolidin-1-yl}urea | 16.3 nM (1.0) |
| 83 | 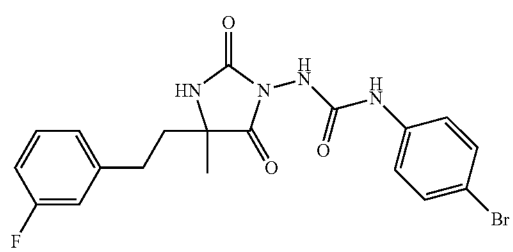 [SMILES: CC1(CCc2cccc(F)c2)NC(=O)N(NC(=O)Nc2ccc(Br)cc2)C1=O] | 1-(4-bromophenyl)-3-{4-[2-(3-fluorophenyl)ethyl]-4-methyl-2,5-dioxoimidazolidin-1-yl}urea | 11.1 nM (1.0) |
| 84 | 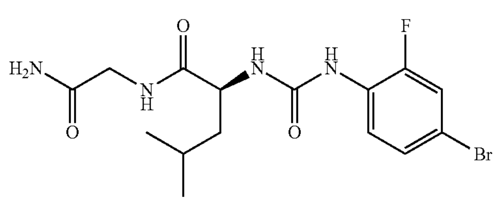 [SMILES: CC(C)C[C@H](NC(=O)Nc1ccc(Br)cc1F)C(=O)NCC(N)=O] | (2S)-N-(2-amino-2-oxoethyl)-2-{[(4-bromo-2-fluorophenyl)carbamoyl]amino}-4-methylpentanamide | 4.5 nM (0.95) |
| 85 | 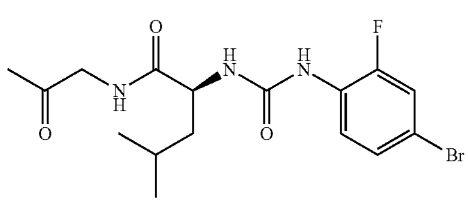 [SMILES: CC(=O)CNC(=O)[C@H](CC(C)C)NC(=O)Nc1ccc(Br)cc1F] | (2S)-2-{[(4-bromo-2-fluorophenyl)carbamoyl]amino}-4-methyl-N-(2-oxopropyl)pentanamide | 20 nM (0.99) |

TABLE 4-continued

| Compound number | Structure | IUPAC name | FPR2 EC$_{50}$ (efficacy) |
|---|---|---|---|
| 86 | 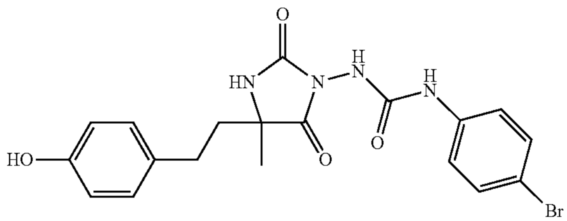 [SMILES: CC1(CCc2ccc(O)cc2)NC(=O)N(NC(=O)Nc2ccc(Br)cc2)C1=O] | 1-(4-bromophenyl)-3-{4-[2-(4-hydroxyphenyl)ethyl]-4-methyl-2,5-dioxoimidazolidin-1-yl}urea | 13.3 nM (1.0) |
| 87 | 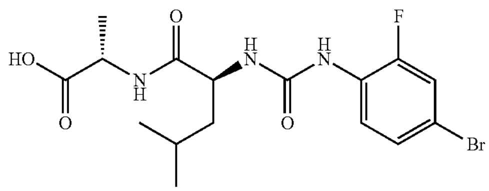 [SMILES: CC(C)C[C@H](NC(=O)Nc1ccc(Br)cc1F)C(=O)N[C@@H](C)C(=O)O] | (2S)-2-{[(2S)-2-{[(4-bromo-2-fluorophenyl)carbamoyl]amino}-4-methylpentanoyl]amino}propanoic acid | 12.1 nM (0.95) |
| 88 | 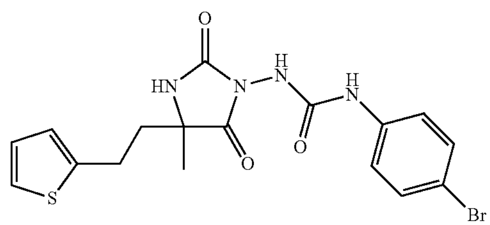 [SMILES: CC1(CCc2cccs2)NC(=O)N(NC(=O)Nc2ccc(Br)cc2)C1=O] | 1-(4-bromophenyl)-3-{4-methyl-2,5-dioxo-4-[2-(thiophen-2-yl)ethyl]imidazolidin-1-yl}urea | 7.9 nM (0.94) |
| 89 | 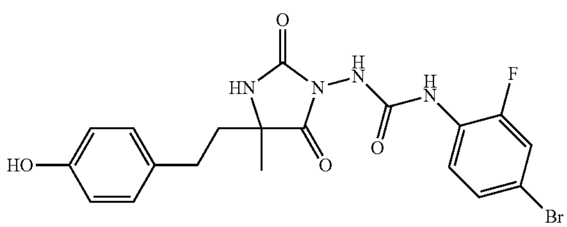 [SMILES: CC1(CCc2ccc(O)cc2)NC(=O)N(NC(=O)Nc2ccc(Br)cc2F)C1=O] | 1-(4-bromo-2-fluorophenyl)-3-{4-[2-(4-hydroxyphenyl)ethyl]-4-methyl-2,5-dioxoimidazolidin-1-yl}urea | 8.7 nM (0.85) |
| 90 | 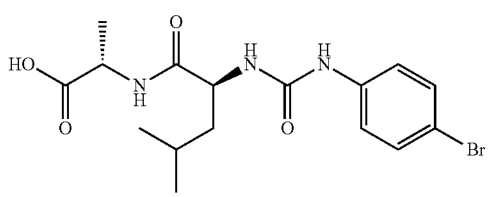 [SMILES: CC(C)C[C@H](NC(=O)Nc1ccc(Br)cc1)C(=O)N[C@@H](C)C(=O)O] | (2S)-2-{[(2S)-2-{[(4-bromophenyl)carbamoyl]amino}-4-methylpentanoyl]amino}propanoic acid | 11.6 nM (1.0) |
| 91 | 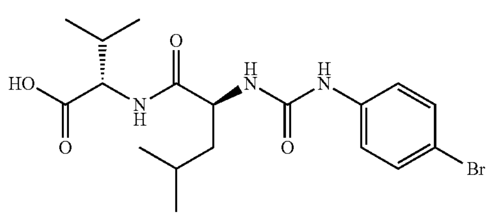 [SMILES: CC(C)C[C@H](NC(=O)Nc1ccc(Br)cc1)C(=O)N[C@H](C(=O)O)C(C)C] | (2S)-2-{[(2S)-2-{[(4-bromophenyl)carbamoyl]amino}-4-methylpentanoyl]amino}-3-methylbutanoic acid | 1.7 nM (0.97) |
| 92 | 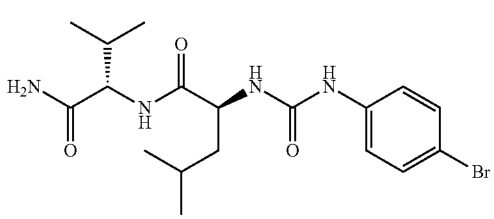 [SMILES: CC(C)C[C@H](NC(=O)Nc1ccc(Br)cc1)C(=O)N[C@H](C(N)=O)C(C)C] | (2S)-N-[(2S)-1-amino-3-methyl-1-oxobutan-2-yl]-2-{[(4-bromophenyl)carbamoyl]amino}-4-methylpentanamide | 5.8 nM (1.0) |

TABLE 4-continued

| Compound number | Structure | IUPAC name | FPR2 EC$_{50}$ (efficacy) |
|---|---|---|---|
| 93 | 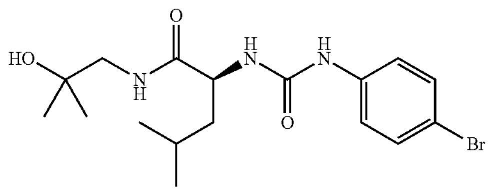 [SMILES: CC(C)C[C@H](NC(=O)Nc1ccc(Br)cc1)C(=O)NCC(C)(C)O] | (2S)-2-{[(4-bromophenyl)carbamoyl]amino}-N-(2-hydroxy-2-methylpropyl)-4-methylpentanamide | 2.5 nM (0.93) |
| 94 | 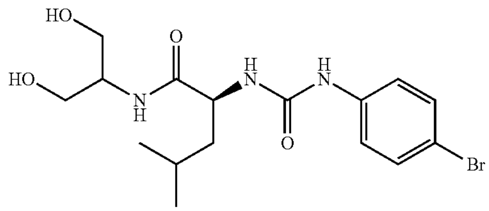 [SMILES: CC(C)C[C@H](NC(=O)Nc1ccc(Br)cc1)C(=O)NC(CO)CO] | (2S)-2-{[(4-bromophenyl)carbamoyl]amino}-N-(1,3-dihydroxypropan-2-yl)-4-methylpentanamide | 7.4 nM (0.96) |
| 95 | 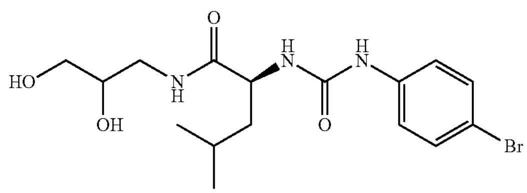 [SMILES: CC(C)C[C@H](NC(=O)Nc1ccc(Br)cc1)C(=O)NCC(O)CO] | (2S)-2-{[(4-bromophenyl)carbamoyl]amino}-N-(2,3-dihydroxypropyl)-4-methylpentanamide | 5.1 nM (0.98) |
| 96 | 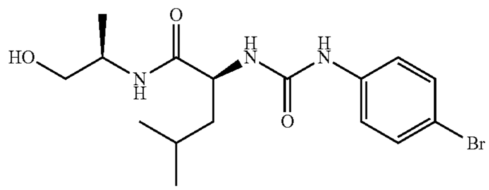 [SMILES: CC(C)C[C@H](NC(=O)Nc1ccc(Br)cc1)C(=O)N[C@H](C)CO] | (2S)-2-{[(4-bromophenyl)carbamoyl]amino}-N-[(2R)-1-hydroxypropan-2-yl]-4-methylpentanamide | 3.0 nM (1.0) |
| 97 | 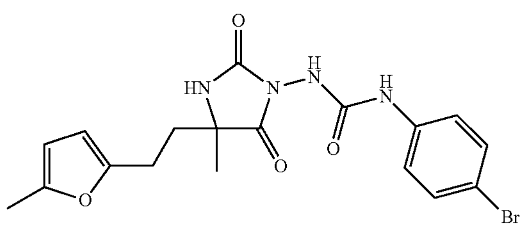 [SMILES: Cc1ccc(CCC2(C)NC(=O)N(NC(=O)Nc3ccc(Br)cc3)C2=O)o1] | 1-(4-bromophenyl)-3-{4-methyl-4-[2-(5-methylfuran-2-yl)ethyl]-2,5-dioxoimidazolidin-1-yl}urea | 3.5 nM (0.95) |
| 98 | 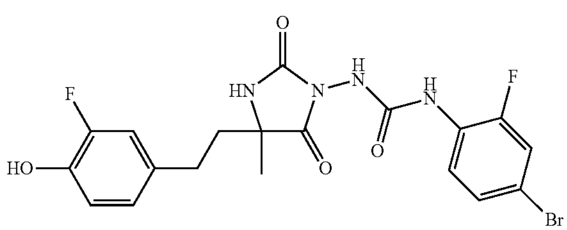 [SMILES: CC1(CCc2ccc(O)c(F)c2)NC(=O)N(NC(=O)Nc2ccc(Br)cc2F)C1=O] | 1-(4-bromo-2-fluorophenyl)-3-{4-[2-(3-fluoro-4-hydroxyphenyl)ethyl]-4-methyl-2,5-dioxoimidazolidin-1-yl}urea | 7.4 nM (0.91) |
| 99 | 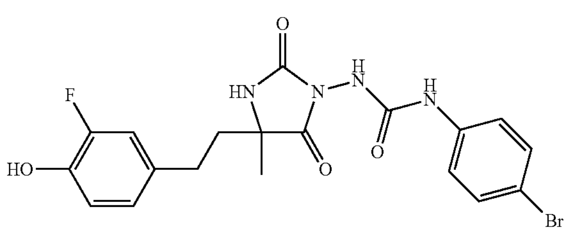 [SMILES: CC1(CCc2ccc(O)c(F)c2)NC(=O)N(NC(=O)Nc2ccc(Br)cc2)C1=O] | 1-(4-bromophenyl)-3-{4-[2-(3-fluoro-4-hydroxyphenyl)ethyl]-4-methyl-2,5-dioxoimidazolidin-1-yl}urea | 8.0 nM (1.0) |

TABLE 4-continued

| Compound number | Structure | IUPAC name | FPR2 EC$_{50}$ (efficacy) |
|---|---|---|---|
| 100 | 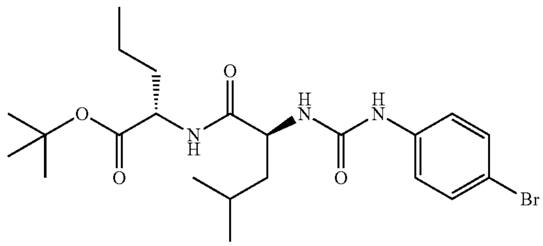 [SMILES: CCC[C@H](NC(=O)[C@H](CC(C)C)NC(=O)Nc1ccc(Br)cc1)C(=O)OC(C)(C)C] | tert-butyl (2S)-2-{[(2S)-2-{[(4-bromophenyl)carbamoyl]amino}-4-methylpentanoyl]amino} pentanoate | 13.0 nM (1.0) |
| 101 | 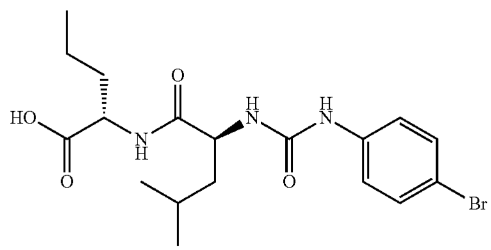 [SMILES: CCC[C@H](NC(=O)[C@H](CC(C)C)NC(=O)Nc1ccc(Br)cc1)C(=O)O] | (2S)-2-{[(2S)-2-{[(4-bromophenyl)carbamoyl] amino}-4-methylpentanoyl] amino}pentanoic acid | 1.0 nM (0.95) |
| 102 | 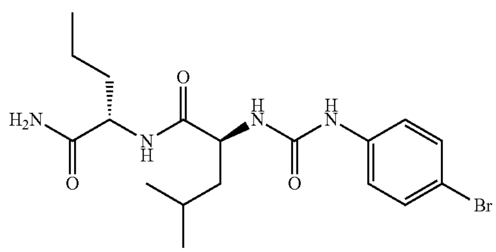 [SMILES: CCC[C@H](NC(=O)[C@H](CC(C)C)NC(=O)Nc1ccc(Br)cc1)C(N)=O] | (2S)-N-[(2S)-1-amino-1-oxopentan-2-yl]-2-{[(4-bromophenyl)carbamoyl] amino}-4-methylpentanamide | 7.3 nM (0.99) |
| 103 | 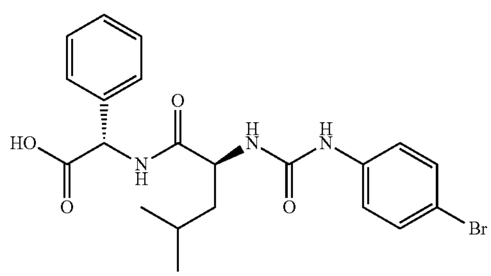 [SMILES: CC(C)C[C@H](NC(=O)Nc1ccc(Br)cc1)C(=O)N[C@H](C(=O)O)c1ccccc1] | (2S)-{[(2S)-2-{[(4-bromophenyl)carbamoyl]amino}-4-methylpentanoyl]amino} (phenyl)ethanoic acid | 9.1 nM (1.0) |
| 104 | 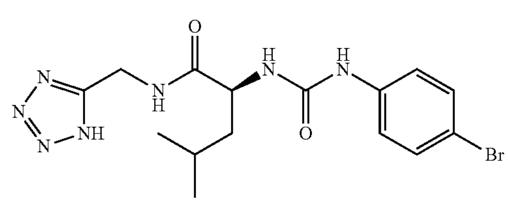 [SMILES: CC(C)C[C@H](NC(=O)Nc1ccc(Br)cc1)C(=O)NCc1nnn[nH]1] | (2S)-2-{[(4-bromophenyl) carbamoyl]amino}-4-methyl-N-(1H-tetrazol-5-ylmethyl) pentanamide | 2.3 nM (0.81) |
| 105 | 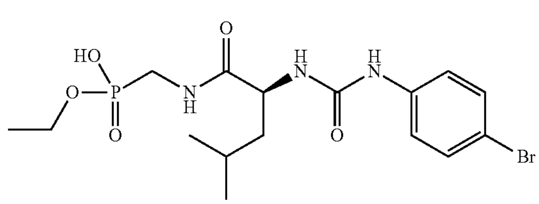 [SMILES: CCOP(=O)(O)CNC(=O)[C@H](CC(C)C)NC(=O)Nc1ccc(Br)cc1] | ethyl hydrogen ({[(2S)-2-{[(4-bromophenyl)carbamoyl]amino}-4-methylpentanoyl]amino} methyl)phosphonate | 0.95 nM (0.88) |

TABLE 4-continued

| Compound number | Structure | IUPAC name | FPR2 EC$_{50}$ (efficacy) |
|---|---|---|---|
| 106 | 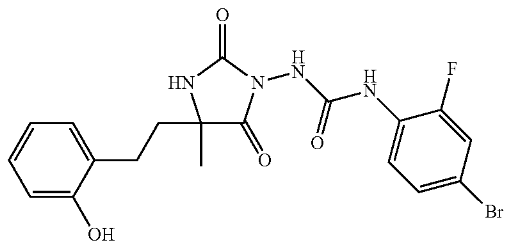 [SMILES: CC1(CCc2ccccc2O)NC(=O)N(NC(=O)Nc2ccc(Br)cc2F)C1=O] | 1-(4-bromo-2-fluorophenyl)-3-{4-[2-(2-hydroxyphenyl)ethyl]-4-methyl-2,5-dioxoimidazolidin-1-yl}urea | 4.0 nM (0.91) |
| 107 | 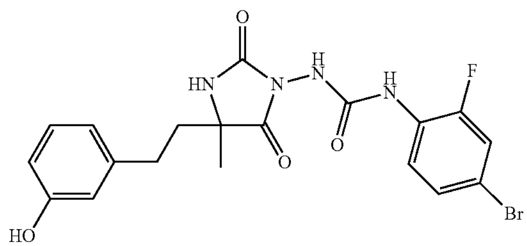 [SMILES: CC1(CCc2cccc(O)c2)NC(=O)N(NC(=O)Nc2ccc(Br)cc2F)C1=O] | 1-(4-bromo-2-fluorophenyl)-3-{4-[2-(3-hydroxyphenyl)ethyl]-4-methyl-2,5-dioxoimidazolidin-1-yl}urea | 2.2 nM (0.79) |
| 108 | 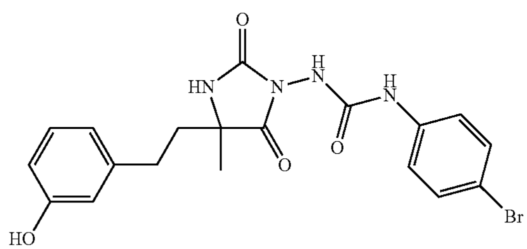 [SMILES: CC1(CCc2cccc(O)c2)NC(=O)N(NC(=O)Nc2ccc(Br)cc2)C1=O] | 1-(4-bromophenyl)-3-{4-[2-(3-hydroxyphenyl)ethyl]-4-methyl-2,5-dioxoimidazolidin-1-yl}urea | 2.1 nM (1.0) |
| 109 | 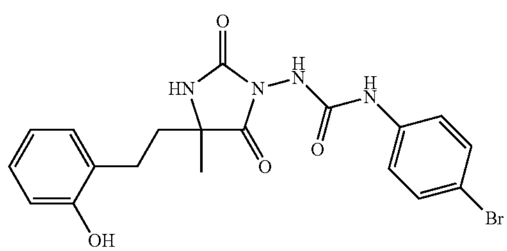 [SMILES: CC1(CCc2ccccc2O)NC(=O)N(NC(=O)Nc2ccc(Br)cc2)C1=O] | 1-(4-bromophenyl)-3-{4-[2-(2-hydroxyphenyl)ethyl]-4-methyl-2,5-dioxoimidazolidin-1-yl}urea | 0.97 nM (0.93) |
| 110 | 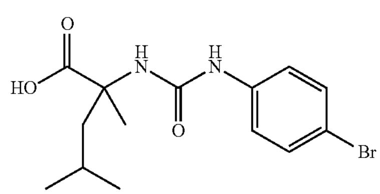 [SMILES: CC(C)CC(C)(NC(=O)Nc1ccc(Br)cc1)C(=O)O] | 2-{[(4-bromophenyl)carbamoyl]amino}-2,4-dimethylpentanoic acid | 19.4 nM (0.98) |
| 111 | 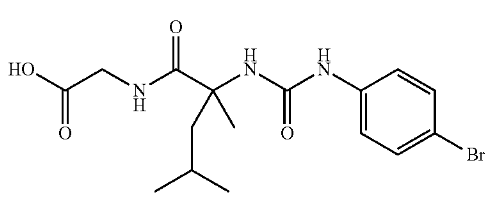 [SMILES: CC(C)CC(C)(NC(=O)Nc1ccc(Br)cc1)C(=O)NCC(=O)O] | [(2-{[(4-bromophenyl)carbamoyl]amino}-2,4-dimethylpentanoyl)amino]acetic acid | 19.1 nM (0.99) |

TABLE 4-continued

| Compound number | Structure | IUPAC name | FPR2 EC$_{50}$ (efficacy) |
|---|---|---|---|
| 112 | 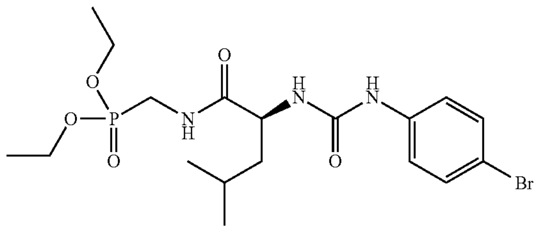 [SMILES: CCOP(=O)(CNC(=O)[C@H](CC(C)C)NC(=O)Nc1ccc(Br)cc1)OCC] | diethyl ({[(2S)-2-{[(4-bromophenyl)carbamoyl]amino}-4-methylpentanoyl]amino}methyl)phosphonate | 0.48 nM (0.95) |
| 113 | 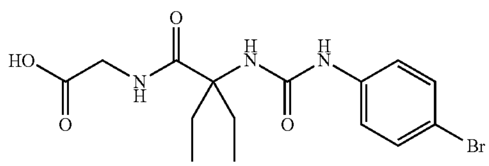 [SMILES: CCC(CC)(NC(=O)Nc1ccc(Br)cc1)C(=O)NCC(=O)O] | (2-{[(4-bromophenyl)carbamoyl]amino}-2-ethylbutanoyl)amino]acetic acid | 18.7 nM (1.0) |
| 114 | 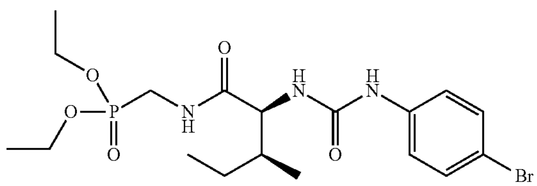 [SMILES: CCOP(=O)(CNC(=O)[C@@H](NC(=O)Nc1ccc(Br)cc1)[C@@H](C)CC)OCC] | diethyl ({[(2S,3S)-2-{[(4-bromophenyl)carbamoyl]amino}-3-methylpentanoyl]amino}methyl)phosphonate | 2.9 nM (1.0) |
| 115 | 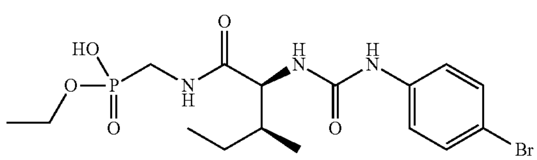 [SMILES: CCOP(=O)(O)CNC(=O)[C@@H](NC(=O)Nc1ccc(Br)cc1)[C@@H](C)CC] | ethyl hydrogen ({[(2S,3S)-2-{[(4-bromophenyl)carbamoyl]amino}-3-methylpentanoyl]amino}methyl)phosphonate | 2.7 nM (0.88) |
| 116 | 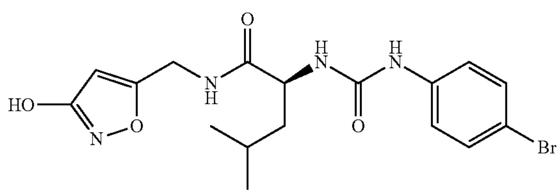 [SMILES: CC(C)C[C@H](NC(=O)Nc1ccc(Br)cc1)C(=O)NCc1cc(O)no1] | (2S)-2-{[(4-bromophenyl)carbamoyl]amino}-N-[(3-hydroxy-1,2-oxazol-5-yl)methyl]-4-methylpentanamide | 12.0 nM (1.0) |
| 117 | 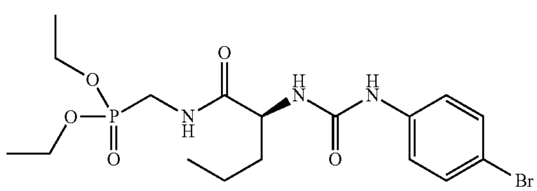 [SMILES: CCC[C@H](NC(=O)Nc1ccc(Br)cc1)C(=O)NCP(=O)(OCC)OCC] | diethyl ({[(2S)-2-{[(4-bromophenyl)carbamoyl]amino}pentanoyl]amino}methyl)phosphonate | 0.27 nM (1.0) |
| 118 | 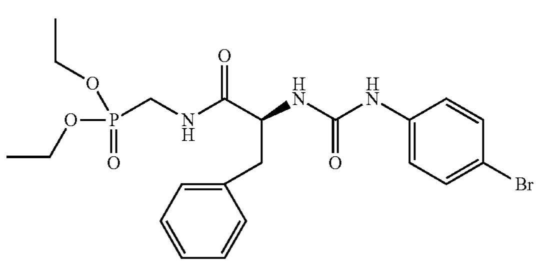 [SMILES: CCOP(=O)(CNC(=O)[C@H](Cc1ccccc1)NC(=O)Nc1ccc(Br)cc1)OCC] | diethyl ({[(2S)-2-{[(4-bromophenyl)carbamoyl]amino}-3-phenylpropanoyl]amino}methyl)phosphonate | 16.1 nM (0.93) |
| 119 | 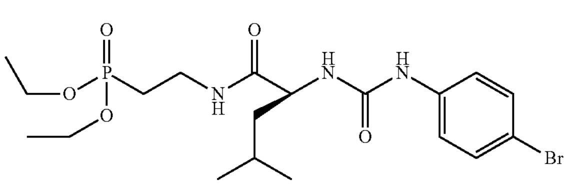 [SMILES: CCOP(=O)(CCNC(=O)[C@H](CC(C)C)NC(=O)Nc1ccc(Br)cc1)OCC] | diethyl (2-{[(2S)-2-{[(4-bromophenyl)carbamoyl]amino}-4-methylpentanoyl]amino}ethyl)phosphonate | 16.1 nM (0.97) |

TABLE 4-continued

| Compound number | Structure | IUPAC name | FPR2 EC$_{50}$ (efficacy) |
|---|---|---|---|
| 120 | 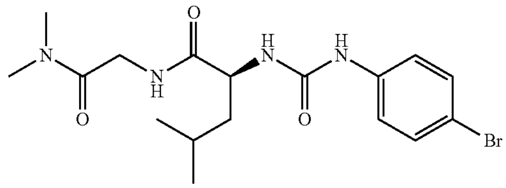 [SMILES: CC(C)C[C@H](NC(=O)Nc1ccc(Br)cc1)C(=O)NCC(=O)N(C)C] | (2S)-2-{[(4-bromophenyl)carbamoyl]amino}-N-[2-(dimethylamino)-2-oxoethyl]-4-methylpentanamide | 1.7 nM (0.99) |
| 121 | 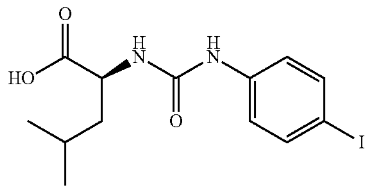 [SMILES: CC(C)C[C@H](NC(=O)Nc1ccc(I)cc1)C(=O)O] | (2S)-2-{[(4-iodophenyl)carbamoyl]amino}-4-methylpentanoic acid | 4.0 nM (0.93) |
| 122 | 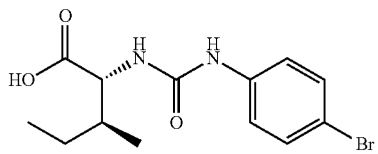 [SMILES: CC[C@H](C)[C@@H](NC(=O)Nc1ccc(Br)cc1)C(=O)O] | (2R,3R)-2-{[(4-bromophenyl)carbamoyl]amino}-3-methylpentanoic acid | 10 μM (0.59) |
| 123 | 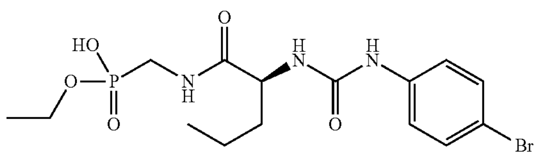 [SMILES: CCC[C@H](NC(=O)Nc1ccc(Br)cc1)C(=O)NCP(=O)(O)OCC] | ethyl hydrogen ({[(2S)-2-{[(4-bromophenyl)carbamoyl]amino}pentanoyl]amino}methyl)phosphonate | 1 nM (0.96) |
| 124 | 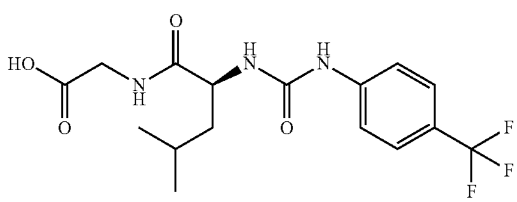 [SMILES: CC(C)C[C@H](NC(=O)Nc1ccc(C(F)(F)F)cc1)C(=O)NCC(=O)O] | {[(2S)-4-methyl-2-({[4-(trifluoromethyl)phenyl]carbamoyl}amino)pentanoyl]amino}acetic acid | 1.8 nM (1.0) |
| 125 | 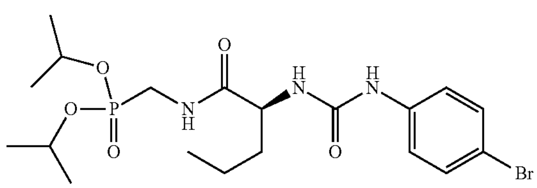 [SMILES: CCC[C@H](NC(=O)Nc1ccc(Br)cc1)C(=O)NCP(=O)(OC(C)C)OC(C)C] | dipropan-2-yl ({[(2S)-2-{[(4-bromophenyl)carbamoyl]amino}pentanoyl]amino}methyl)phosphonate | 1.2 nM (1.0) |
| 126 | 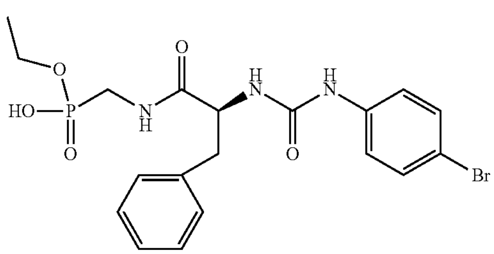 [SMILES: CCOP(=O)(O)CNC(=O)[C@H](Cc1ccccc1)NC(=O)Nc1ccc(Br)cc1] | ethyl hydrogen ({[(2S)-2-{[(4-bromophenyl)carbamoyl]amino}-3-phenylpropanoyl]amino}methyl)phosphonate | 16.0 nM (1.0) |
| 127 | 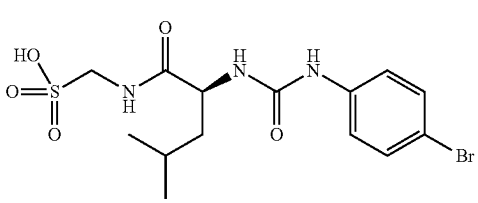 [SMILES: CC(C)C[C@H](NC(=O)Nc1ccc(Br)cc1)C(=O)NCS(=O)(=O)O] | {[(2S)-2-{[(4-bromophenyl)carbamoyl]amino}-4-methylpentanoyl]amino}methanesulfonic acid | 2.0 nM (0.91) |

TABLE 4-continued

| Compound number | Structure | IUPAC name | FPR2 EC$_{50}$ (efficacy) |
|---|---|---|---|
| 128 | 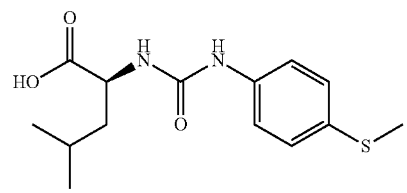 [SMILES: CSc1ccc(NC(=O)N[C@@H](CC(C)C)C(=O)O)cc1] | (2S)-4-methyl-2-({[4-(methylsulfanyl)phenyl]carbamoyl}amino)pentanoic acid | 16.8 nM (0.92) |
| 129 | 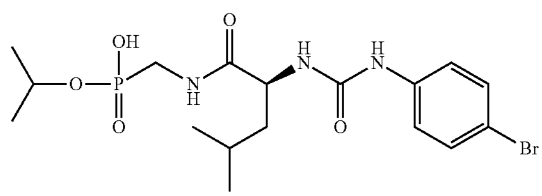 [SMILES: CC(C)C[C@H](NC(=O)Nc1ccc(Br)cc1)C(=O)NCP(=O)(O)OC(C)C] | propan-2-yl hydrogen {[(2-{[(4-bromophenyl)carbamoyl]amino}pentanoyl)amino]methyl}phosphonate | 1.87 nM (0.89) |
| 130 | 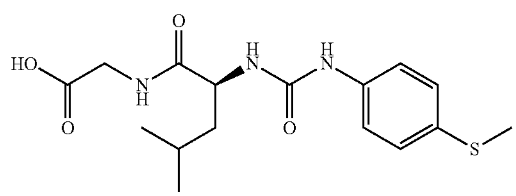 [SMILES: CSc1ccc(NC(=O)N[C@@H](CC(C)C)C(=O)NCC(=O)O)cc1] | {[(2S)-4-methyl-2-({[4-(methylsulfanyl)phenyl]carbamoyl}amino)pentanoyl]amino}acetic acid | 3.0 nM (1.0) |
| 131 | 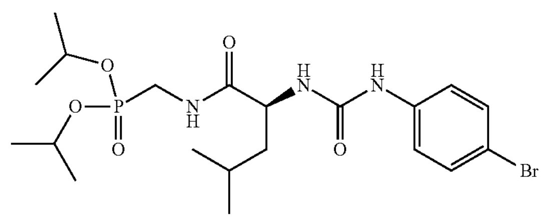 [SMILES: CC(C)C[C@H](NC(=O)Nc1ccc(Br)cc1)C(=O)NCP(=O)(OC(C)C)OC(C)C] | dipropan-2-yl ({[(2S)-2-{[(4-bromophenyl)carbamoyl]amino}-4-methylpentanoyl]amino}methyl)phosphonate | 4.0 nM (1.0) |
| 132 | 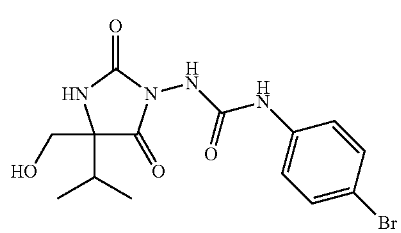 [SMILES: CC(C)C1(CO)NC(=O)N(NC(=O)Nc2ccc(Br)cc2)C1=O] | 1-(4-bromophenyl)-3-[4-(hydroxymethyl)-2,5-dioxo-4-(propan-2-yl)imidazolidin-1-yl]urea | 16.2 nM (0.86) |
| 133 | 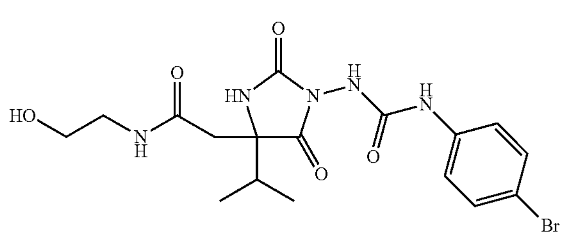 [SMILES: CC(C)C1(CC(=O)NCCO)NC(=O)N(NC(=O)Nc2ccc(Br)cc2)C1=O] | 2-[1-{[(4-bromophenyl)carbamoyl]amino}-2,5-dioxo-4-(propan-2-yl)imidazolidin-4-yl]-N-(2-hydroxyethyl)acetamide | 2.7 nM (1.0) |
| 134 | 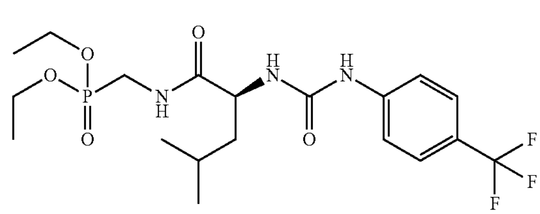 [SMILES: CCOP(=O)(CNC(=O)[C@H](CC(C)C)NC(=O)Nc1ccc(C(F)(F)F)cc1)OCC] | diethyl ({[(2S)-4-methyl-2-({[4-(trifluoromethyl)phenyl]carbamoyl}amino)pentanoyl]amino}methyl)phosphonate | 5.5 nM (0.97) |

TABLE 4-continued

| Compound number | Structure | IUPAC name | FPR2 EC$_{50}$ (efficacy) |
|---|---|---|---|
| 135 | 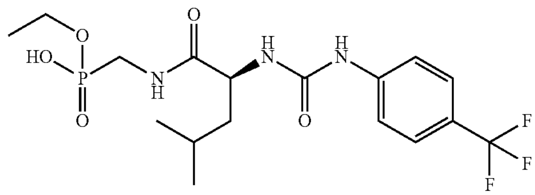 [SMILES: CCOP(=O)(O)CNC(=O)[C@H](CC(C)C)NC(=O)Nc1ccc(C(F)(F)F)cc1] | ethyl hydrogen ({[(2S)-4-methyl-2-({[4-(trifluoromethyl)phenyl]carbamoyl}amino)pentanoyl]amino}methyl)phosphonate | 1.9 nM (0.91) |
| 136 | 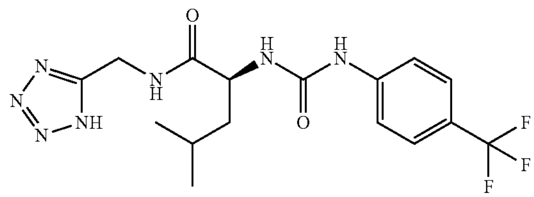 [SMILES: CC(C)C[C@H](NC(=O)Nc1ccc(C(F)(F)F)cc1)C(=O)NCc1nnn[nH]1] | (2S)-4-methyl-N-(1H-tetrazol-5-ylmethyl)-2-({[4-(trifluoromethyl)phenyl]carbamoyl}amino)pentanamide | 3.7 nM (0.96) |
| 237 | 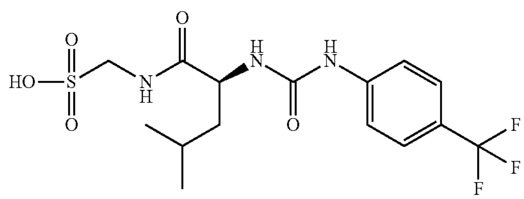 [SMILES: CC(C)C[C@H](NC(=O)Nc1ccc(C(F)(F)F)cc1)C(=O)NCS(=O)(=O)O] | {[(2S)-4-methyl-2-({[4-(trifluoromethyl)phenyl]carbamoyl}amino)pentanoyl]amino}methanesulfonic acid | 1.9 nM (0.99) |
| 138 | 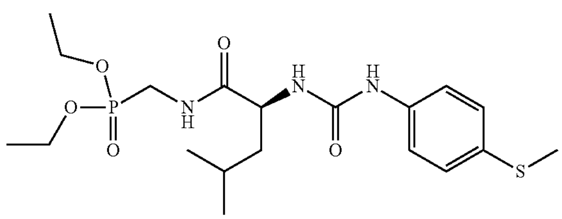 [SMILES: CCOP(=O)(CNC(=O)[C@H](CC(C)C)NC(=O)Nc1ccc(SC)cc1)OCC] | diethyl ({[(2S)-4-methyl-2-({[4-(methylsulfanyl)phenyl]carbamoyl}amino)pentanoyl]amino}methyl)phosphonate | 3.5 nM (0.91) |
| 139 | 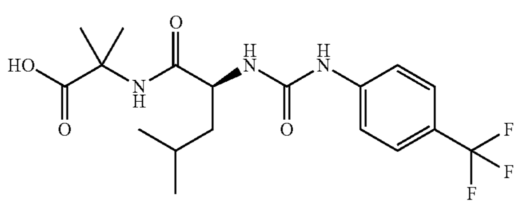 [SMILES: CC(C)C[C@H](NC(=O)Nc1ccc(C(F)(F)F)cc1)C(=O)NC(C)(C)C(=O)O] | 2-methyl-2-{[(2S)-4-methyl-2-({[4-(trifluoromethyl)phenyl]carbamoyl}amino)pentanoyl]amino}propanoic acid | 2.5 nM (0.92) |
| 140 | 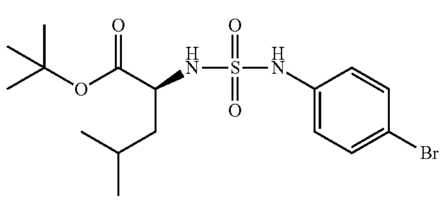 [SMILES: CC(C)C[C@H](NS(=O)(=O)Nc1ccc(Br)cc1)C(=O)OC(C)(C)C] | tert-butyl (2S)-2-{[(4-bromophenyl)sulfamoyl]amino}-4-methylpentanoate | NA |
| 141 | 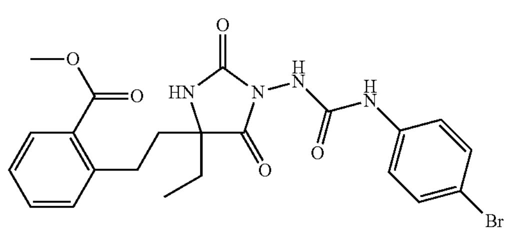 [SMILES: CCC1(CCc2ccccc2C(=O)OC)NC(=O)N(NC(=O)Nc2ccc(Br)cc2)C1=O] | methyl 2-[2-(1-{[(4-bromophenyl)carbamoyl]amino}-4-ethyl-2,5-dioxoimidazolidin-4-yl)ethyl]benzoate | 10.3 nM (0.92) |

TABLE 4-continued

| Compound number | Structure | IUPAC name | FPR2 EC$_{50}$ (efficacy) |
|---|---|---|---|
| 142 | 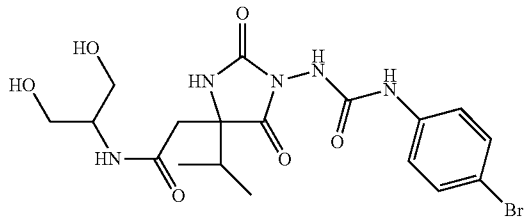 [SMILES: CC(C)C1(CC(=O)NC(CO)CO)NC(=O)N(NC(=O)Nc2ccc(Br)cc2)C1=O] | 2-[1-{[(4-bromophenyl)carbamoyl]amino}-2,5-dioxo-4-(propan-2-yl)imidazolidin-4-yl]-N-(1,3-dihydroxypropan-2-yl)acetamide | 13.8 nM (0.92) |
| 143 | 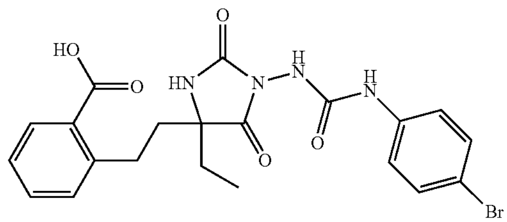 [SMILES: CCC1(CCc2ccccc2C(=O)O)NC(=O)N(NC(=O)Nc2ccc(Br)cc2)C1=O] | 2-[2-(1-{[(4-bromophenyl)carbamoyl]amino}-4-ethyl-2,5-dioxoimidazolidin-4-yl)ethyl]benzoic acid | 17.2 nM (1.0) |
| 144 | 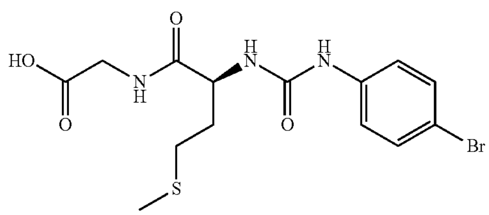 [SMILES: CSCC[C@H](NC(=O)Nc1ccc(Br)cc1)C(=O)NCC(=O)O] | {[(2S)-2-{[(4-bromophenyl)carbamoyl]amino}-4-(methylsulfanyl)butanoyl]amino}acetic acid | 6.3 nM (0.91) |
| 145 | 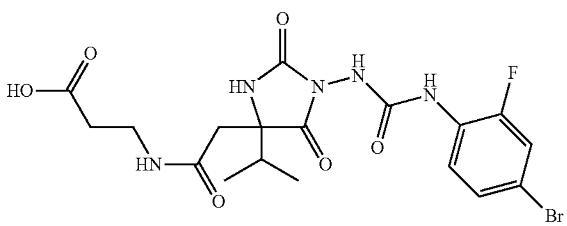 [SMILES: CC(C)C1(CC(=O)NCCC(=O)O)NC(=O)N(NC(=O)Nc2ccc(Br)cc2F)C1=O] | 3-({[1-{[(4-bromo-2-fluorophenyl)carbamoyl]amino}-2,5-dioxo-4-(propan-2-yl)imidazolidin-4-yl]acetyl}amino)propanoic acid | 1.0 nM (1.0) |
| 146 | 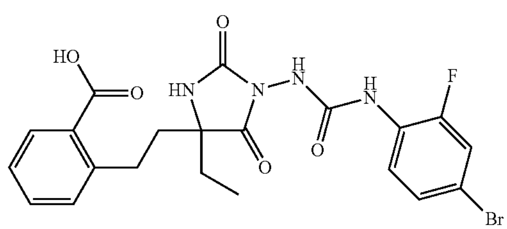 [SMILES: CCC1(CCc2ccccc2C(=O)O)NC(=O)N(NC(=O)Nc2ccc(Br)cc2F)C1=O] | 2-[2-(1-{[(4-bromo-2-fluorophenyl)carbamoyl]amino}-4-ethyl-2,5-dioxoimidazolidin-4-yl)ethyl]benzoic acid | 11.1 nM (1.0) |
| 147 | 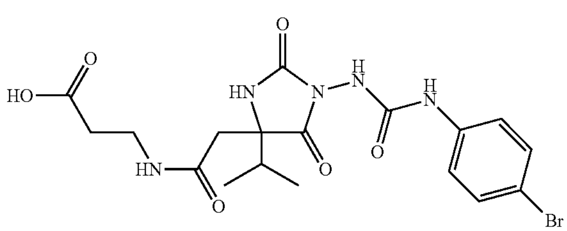 [SMILES: CC(C)C1(CC(=O)NCCC(=O)O)NC(=O)N(NC(=O)Nc2ccc(Br)cc2)C1=O] | 3-({[1-{[(4-bromophenyl)carbamoyl]amino}-2,5-dioxo-4-(propan-2-yl)imidazolidin-4-yl]acetyl}amino)propanoic acid | 3.9 nM (0.99) |
| 148 | 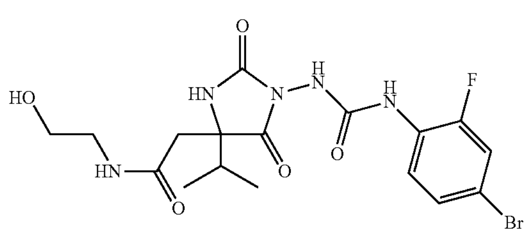 [SMILES: CC(C)C1(CC(=O)NCCO)NC(=O)N(NC(=O)Nc2ccc(Br)cc2F)C1=O] | 2-[1-{[(4-bromo-2-fluorophenyl)carbamoyl]amino}-2,5-dioxo-4-(propan-2-yl)imidazolidin-4-yl]-N-(2-hydroxyethyl)acetamide | 6.9 nM (0.98) |

TABLE 4-continued

| Compound number | Structure | IUPAC name | FPR2 EC$_{50}$ (efficacy) |
|---|---|---|---|
| 149 | 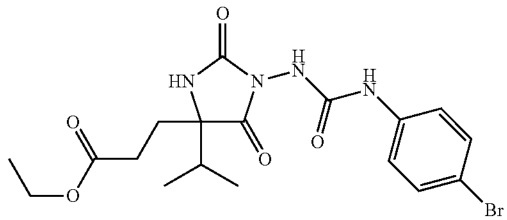 [SMILES: CCOC(=O)CCC1(C(C)C)NC(=O)N(NC(=O)Nc2ccc(Br)cc2)C1=O] | ethyl 3-[1-{[(4-bromophenyl)carbamoyl]amino}-2,5-dioxo-4-(propan-2-yl)imidazolidin-4-yl]propanoate | 6.6 nM (0.94) |
| 150 | 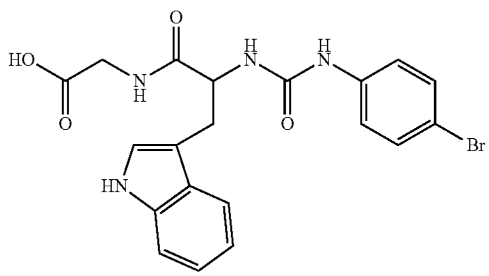 [SMILES: O=C(O)CNC(=O)C(Cc1c[nH]c2ccccc12)NC(=O)Nc1ccc(Br)cc1] | {[2-{[(4-bromophenyl)carbamoyl]amino}-3-(1H-indol-3-yl)propanoyl]amino}acetic acid | 1.4 nM (0.98) |
| 151 | 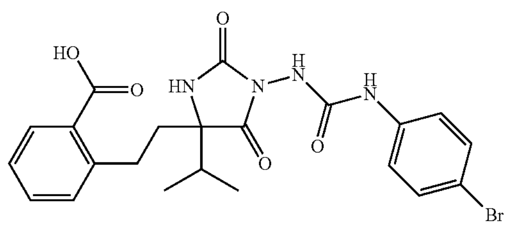 [SMILES: CC(C)C1(CCc2ccccc2C(=O)O)NC(=O)N(NC(=O)Nc2ccc(Br)cc2)C1=O] | 2-{2-[1-{[(4-bromophenyl)carbamoyl]amino}-2,5-dioxo-4-(propan-2-yl)imidazolidin-4-yl]ethyl}benzoic acid | 5.8 nM (1.0) |
| 152 | 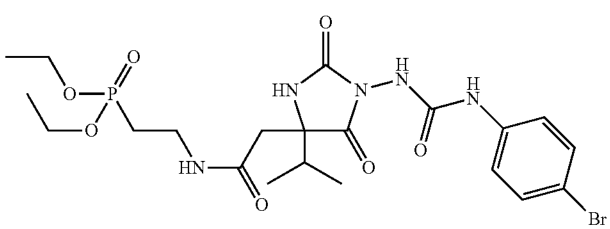 [SMILES: CCOP(=O)(CCNC(=O)CC1(C(C)C)NC(=O)N(NC(=O)Nc2ccc(Br)cc2)C1=O)OCC] | diethyl [2-({[1-{[(4-bromophenyl)carbamoyl]amino}-2,5-dioxo-4-(propan-2-yl)imidazolidin-4-yl]acetyl}amino)ethyl]phosphonate | 11 nM (1.0) |
| 153 | 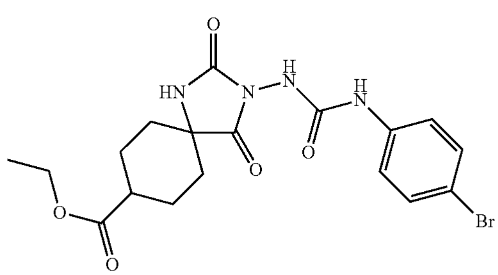 [SMILES: CCOC(=O)C1CCC2(CC1)NC(=O)N(NC(=O)Nc1ccc(Br)cc1)C2=O] | ethyl 3-{[(4-bromophenyl)carbamoyl]amino}-2,4-dioxo-1,3-diazaspiro[4.5]decane-8-carboxylate | 12 nM (0.99) |
| 154 | 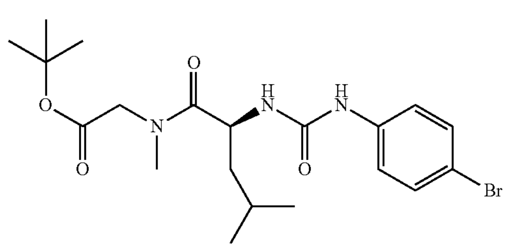 [SMILES: CC(C)C[C@H](NC(=O)Nc1ccc(Br)cc1)C(=O)N(C)CC(=O)OC(C)(C)C] | tert-butyl {[(2S)-2-{[(4-bromophenyl)carbamoyl]amino}-4-methylpentanoyl](methyl)amino}acetate | 12 nM (0.85) |

TABLE 4-continued

| Compound number | Structure | IUPAC name | FPR2 EC$_{50}$ (efficacy) |
|---|---|---|---|
| 155 | 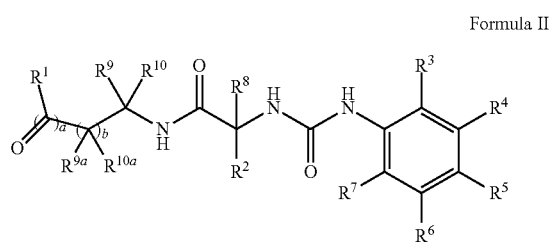 | {[(2S)-2-{[(4-bromophenyl)carbamoyl]amino}-4-methylpentanoyl](methyl)amino}acetic acid | 1.0 nM (1.0) |

Immunohistochemistry: Chromogenic DAB immunohistochemistry with antibodies specific to FPR2 was used to determine localization in normal human, primate, and rat eyes. Anti-FPR2 antibody (Abcam) was used at a dilution of 1:200 to detect FPR2 protein in all species.

Endotoxin-Induced Uveitis in Rats: Uveitis is a harmful ocular inflammatory condition in humans. Anterior uveitis is a recurrent inflammatory disease and may have potentially blinding consequence. The pathogenesis of the disease is poorly understood, and the anti-inflammatory therapy used is non-specific and is associated with significant complications. Animal models are key to understanding the disease and testing novel therapies. A single low dose of lipopolysaccharide (LPS) in the footpad induces anterior uveitis in rats. This model known as endotoxin-induced uveitis serves as a useful paradigm of human anterior uveitis. Male Lewis rats (260±25 grams) were purchased from Charles River Laboratory. Rats were footpad-injected (hind left side) with 100 µl of 1 mg/ml LPS (List Biological Labs) solution (in sterile 0.9% saline). Test compounds were formulated in the vehicle consisting of sodium phosphate, dibasic heptahydrate, salts, CMC and sterile water. Compounds were topically (0.1-1%) or subcutaneously (10 mg/kg) dosed 2 hr after LPS. Animals were sacrificed at 24 hours following LPS injection. Aqueous humor was collected and analyzed to determine inflammatory cell counts and total protein concentrations.

Alkali Burn in Rabbits: Corneal epithelium plays an important role in the maintenance of corneal function and integrity. Prolonged corneal epithelial defects causes corneal opacity, neovascularization, bacterial infection and visual loss. Corneal epithelial healing is a complex process involving inflammatory response to injury, cell proliferation and migration. Animal models of corneal injury are every useful to test new anti-inflammatory and pro-wound healing therapies. New Zealand White rabbits weighing between 2.1 and 2.5 kg were anesthetized systemically with Ketamine/Xylazine (35/5 mg/kg) subcutaneously and topically with proparacaine (0.5%). The corneal epithelial wound in one eye was induced with a NaOH saturated filter paper containing 1.0 N NaOH for 30 seconds. The eyes were rinsed with sterile PBS. The corneal wound was confirmed by fluorescein staining with 10% sodium fluorescein (Science Lab Com) and slit lamp photography. Test compounds were formulated in the vehicle described above. For initial studies compounds were topically dosed three times a day. Quantification of corneal wound areas was done using Image J software where fluorescing stain green part was traced and converted to total pixel.

The compounds below would be expected to have significant effects in many different types of ocular inflammation, but have been exemplified by demonstrating anti-inflammatory activity in endotoxin-induced uveitis in rats (FIGS. 1 and 2). Anti-inflammatory activity in this model has been exemplified with the following FPR2 agonists.

Figure 3:
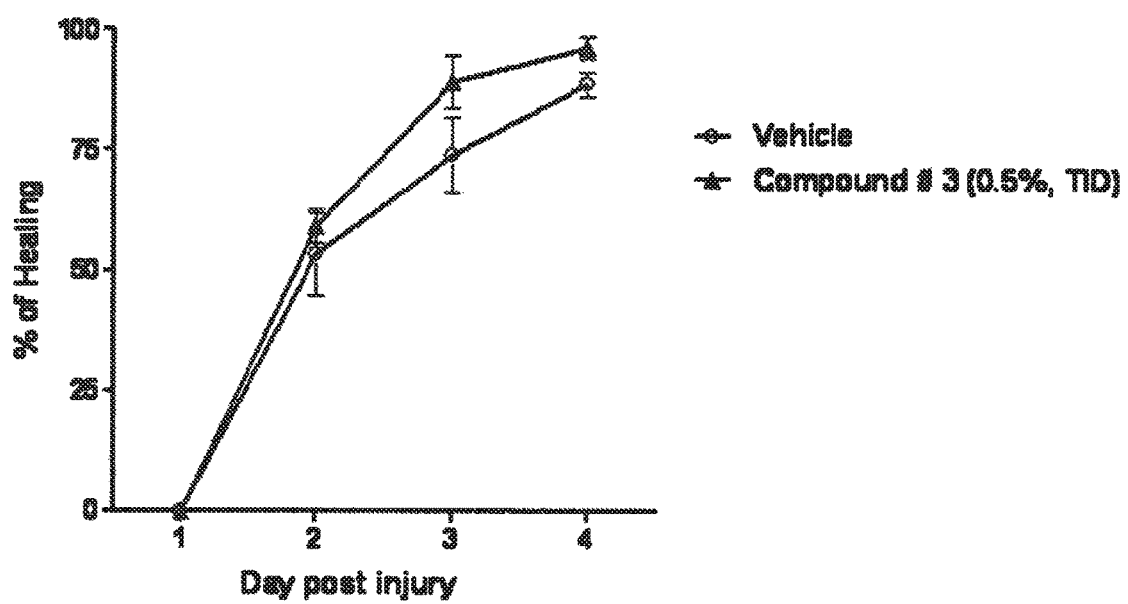
FIG. 3 shows accelerated healing and re-epithelialization in a rabbit model of corneal wound as exemplified by Compound 3, {[(2S,3S)-2-{[(4-bromophenyl)carbamoyl]amino}-3-methylpentanoyl]amino}acetic acid.

In this model the compounds show a strong anti-inflammatory activity in blocking the infiltration of neutrophils and protein into the anterior chamber. In addition FPR2 agonists show accelerated healing and re-epithelialization in mouse models of corneal wound as exemplified by compound {[(2S,3S)-2-{[(4-bromophenyl)carbamoyl]amino}-3-methylpentanoyl]amino}acetic acid in (FIG. 3). These data demonstrate that FPR2 agonists are potent and efficacious anti-inflammatory agents suitable for ocular use in different models of ocular inflammation.

What is claimed is:

1. A method of treating an ocular inflammatory disease in a subject in need of such treatment, the method comprising administering a pharmaceutical composition comprising a therapeutically effective amount of at least one formyl peptide receptor 2 (FPR2) agonist of Formula II:

Formula II wherein:
a is 1 and b is 0; a is 0 and b is 1, or a is 1 and b is 1;
R$^1$ is optionally substituted C$_{1-8}$ alkyl, optionally substituted C$_{3-8}$ cycloalkyl, optionally substituted heterocycle, optionally substituted C$_{3-8}$ cycloalkyl, optionally substituted C$_{6-10}$ aryl, optionally substituted C$_{3-8}$ cycloalkenyl, -NR$^{11}$ R$^{12}$ or -OR$^{13}$;
R$^2$ is optionally substituted C$_{1-8}$ alkyl or optionally substituted C$_{6-10}$ aryl; R$^3$ is hydrogen, optionally substituted C$_{1-8}$ alkyl, halogen, —COOR$^{15}$, —OR$^{13}$, —NR$^{11}$ R$^{12}$, NO$_2$ optionally substituted heterocycle, optionally substituted C$_{3-8}$ cycloalkyl, optionally substituted C$_{6-10}$ aryl or optionally substituted C$_{3-8}$ cycloalkenyl;
R$^4$ is hydrogen, optionally substituted C$_{1-8}$ alkyl, halogen, —COOR$^{15}$, —OR$^{13}$, —NR$^{11}$ R$^{12}$, NO$_2$, optionally substituted heterocycle, optionally substituted C$_{3-8}$ cycloalkyl, optionally substituted C$_{6-10}$ aryl or optionally substituted C$_{3-8}$ cycloalkenyl;
R$^5$ is halogen, —CF$_3$ or —S(O)$_n$ R$^{14}$;
n is 0, 1 or 2;
R$^6$ is hydrogen, optionally substituted C$_{1-8}$ alkyl, halogen, —COOR$^{15}$, —OR$^{13}$, —NR$^{11}$ R$^{12}$, NO$_2$ , optionally substituted heterocycle, optionally substituted $C_{3-8}$ cycloalkyl, optionally substituted $C_{6-10}$ aryl or optionally substituted $C_{3-8}$ cycloalkenyl;

$R^7$ is hydrogen, optionally substituted $C_{1-8}$ alkyl, halogen, —COOR$^{15}$, —OR$^{13}$, —NR$^{11}$ R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;

$R^8$ is hydrogen, optionally substituted $C_{1-8}$ alkyl or optionally substituted $C_{6-10}$ aryl;

$R^9$ is hydrogen, optionally substituted $C_{1-8}$ alkyl or optionally substituted $C_{6-10}$ aryl;

$R^{10}$ is hydrogen, optionally substituted $C_{1-8}$ alkyl or optionally substituted $C_{6-10}$ aryl;

$R^{9a}$ is hydrogen, optionally substituted $C_{1-8}$ alkyl or optionally substituted $C_{6-10}$ aryl;

$R^{10a}$ is hydrogen, optionally substituted $C_{1-8}$ alkyl or optionally substituted $C_{6-10}$ aryl;

$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{14}$ is hydrogen, CF$_3$ or optionally substituted $C_{1-8}$ alkyl;
and $R^{15}$ is hydrogen or optionally substituted $C_{1-8}$ alkyl;

wherein the ocular inflammatory disease is selected from the group consisting of uveitis, dry eye, keratitis, allergic eye disease, infectious keratitis, herpetic keratitis, corneal angiogenesis, lymphangiogenesis, retinitis, choroiditis, acute multifocal placoid pigment epitheliopathy, Behcet's disease, post-surgical corneal wound healing, wet age-related macular degeneration (ARMD) and dry ARMD.

2. The method of claim 1, wherein the at least one FPR2 agonist is selected from the group consisting of:

{[(2S)-2-{[(4-bromophenyl)carbamoyl]amino}-3-phenylpropanoyl]amino}acetic acid

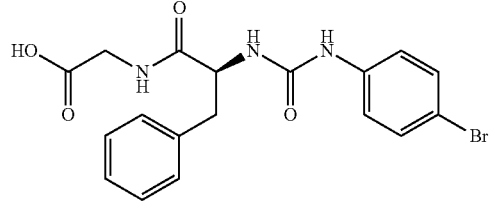

3-{[(2S)-2-{[(4-bromophenyl)carbamoyl]amino}-3-phenylpropanoyl]amino}propanoic acid

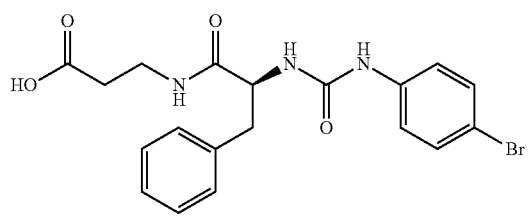 [SMILES: O=C(O)CCNC(=O)[C@H](Cc1ccccc1)NC(=O)Nc1ccc(Br)cc1]

{[(2S,3S)-2-{[(4-bromo-2-fluorophenyl)carbamoyl]amino}-3-methylpentanoyl]amino}acetic acid

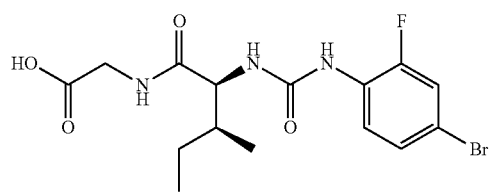 [SMILES: CC[C@H](C)[C@H](NC(=O)Nc1ccc(Br)cc1F)C(=O)NCC(=O)O]

{[(2S,3S)-2-{[(4-bromophenyl)carbamoyl]amino}-3-methylpentanoyl]amino}acetic acid

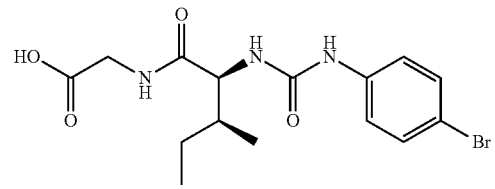 [SMILES: CC[C@H](C)[C@H](NC(=O)Nc1ccc(Br)cc1)C(=O)NCC(=O)O]

{[(2S)-2-{[(4-bromophenyl)carbamoyl]amino}pentanoyl]amino}acetic acid

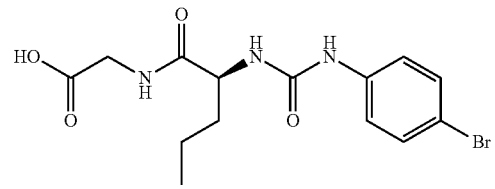 [SMILES: CCC[C@H](NC(=O)Nc1ccc(Br)cc1)C(=O)NCC(=O)O]

{[(2S)-2-{[(4-bromophenyl)carbamoyl]amino}-4-methylpentanoyl]amino}acetic acid

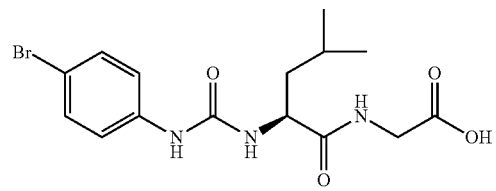 [SMILES: CC(C)C[C@H](NC(=O)Nc1ccc(Br)cc1)C(=O)NCC(=O)O]

tert-Butyl{[(2S)-2-{[(4-bromophenyl)carbamoyl]amino}-3-phenylpropanoyl]amino}acetate

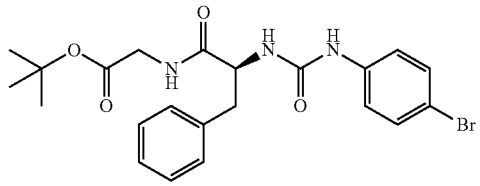 [SMILES: CC(C)(C)OC(=O)CNC(=O)[C@H](Cc1ccccc1)NC(=O)Nc1ccc(Br)cc1]

tert-butyl 3-{[(2S)-2-{[(4-bromophenyl)carbamoyl]amino}-3-phenylpropanoyl]amino}propanoate

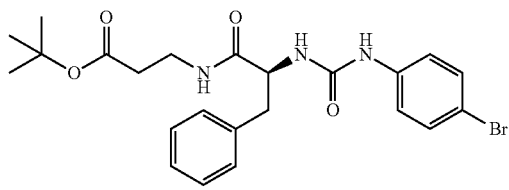 [SMILES: CC(C)(C)OC(=O)CCNC(=O)[C@H](Cc1ccccc1)NC(=O)Nc1ccc(Br)cc1]

(2S)-2-{[(4-bromophenyl) carbamoyl]amino}-N-(2-hydroxyethyl)-3-phenylpropanamide

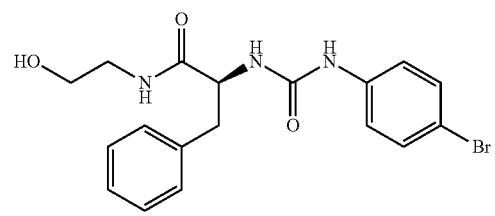 [SMILES: O=C(Nc1ccc(Br)cc1)N[C@@H](Cc1ccccc1)C(=O)NCCO]

tert-butyl {[(2S,3S)-2-{[(4-bromo-2-fluorophenyl)carbamoyl]amino}-3-methylpentanoyl]amino}acetate

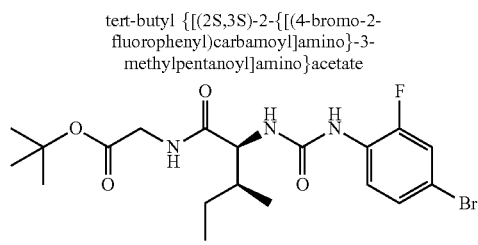

tert-butyl{[(2S,3S)-2-{[(4-bromophenyl)carbamoyl]amino}-3-methylpentanoyl]amino}acetate

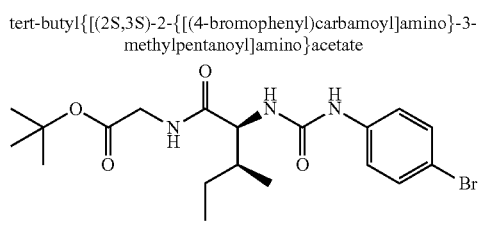

(2S,3S)-2-{[(4-bromophenyl)carbamoyl]amino}-3-methyl-N-(2-oxopropyl)pentanamide

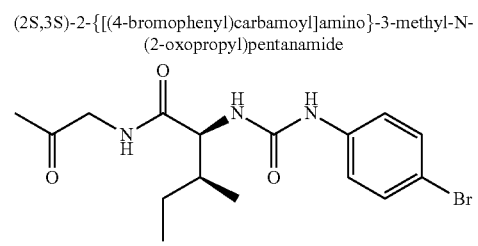

(2S,3S)-2-{[(4-bromo-2-fluorophenyl)carbamoyl]amino}-3-methyl-N-(2-oxopropyl)pentanamide

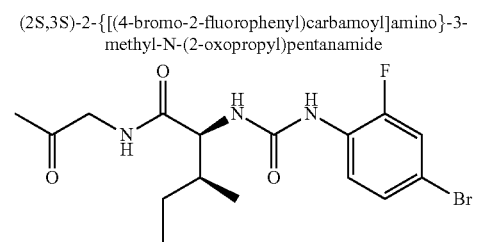

(2S,3S)-2-{[(4-bromophenyl)carbamoyl]amino}-N-(2-hydroxyethyl)-3-methylpentanamide

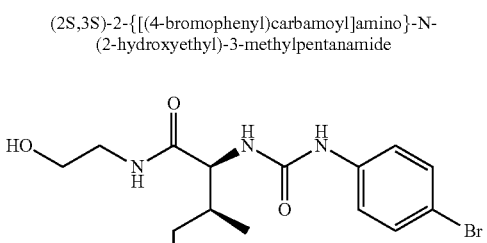

(2S,3S)-2-{[(4-bromo-2-fluorophenyl) carbamoyl]amino}-N-(2-hydroxyethyl)-3-methylpentanamide

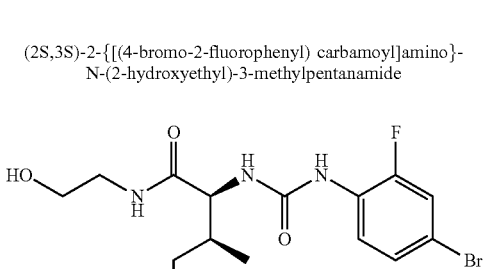

(2S)-2-{[(4-bromophenyl)carbamoyl]amino}-N-(2-oxopropyl)-3-phenylpropanamide

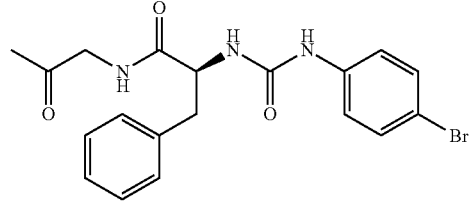 [SMILES: CC(=O)CNC(=O)[C@H](Cc1ccccc1)NC(=O)Nc1ccc(Br)cc1]

(2S)-2-{[(4-bromo-2-fluorophenyl)carbamoyl]amino}-N-(2-oxopropyl)-3-phenylpropanamide

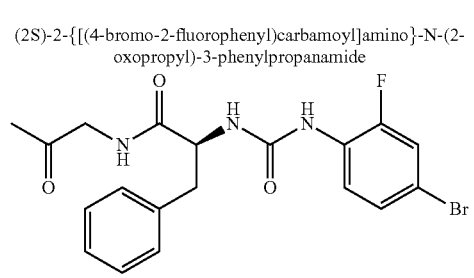

tert-butyl {[(2S)-2-{[(4-bromophenyl)carbamoyl]amino}-pentanoyl]amino}acetate

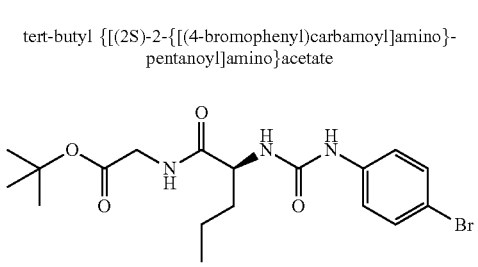

(2S)-2-{[(4-bromo-2-fluorophenyl)carbamoyl]amino}-N-(2-hydroxyethyl)-3-phenylpropanamide

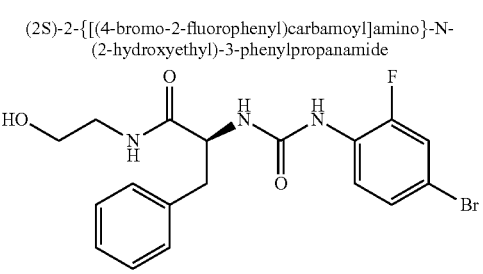

(2S)-2-{[(4-bromophenyl)carbamoyl]amino}-N-(2-hydroxyethyl)pentanamide

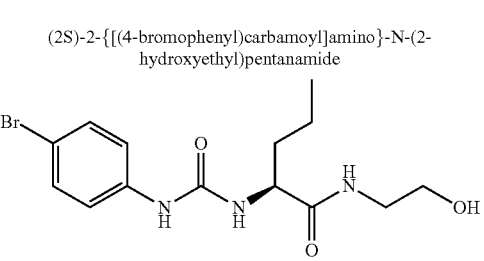

(2S)-2-{[(4-bromo-2-fluorophenyl)carbamoyl]amino}-N-(2-hydroxyethyl) pentanamide

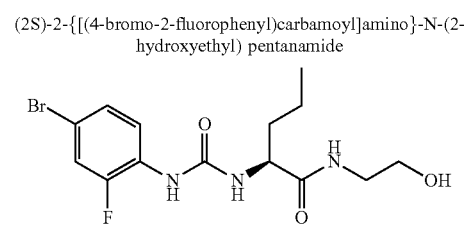

methyl {[(2S)-2-{[(4-bromophenyl)carbamoyl]amino}-pentanoyl]amino}acetate

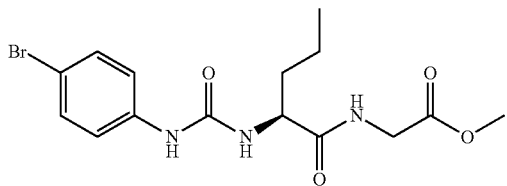 [SMILES: CCC[C@H](NC(=O)Nc1ccc(Br)cc1)C(=O)NCC(=O)OC]

ethyl {[(2S)-2-{[(4-bromophenyl)carbamoyl]amino}-pentanoyl]amino}acetate

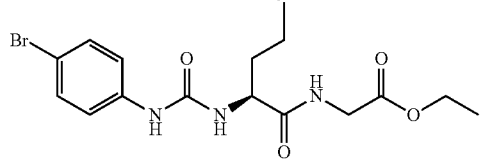 [SMILES: CCC[C@H](NC(=O)Nc1ccc(Br)cc1)C(=O)NCC(=O)OCC]

isopropyl {[(2S)-2-{[(4-bromophenyl)carbamoyl]amino}-pentanoyl]amino} acetate

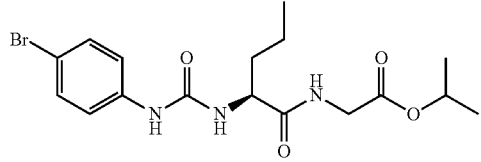 [SMILES: CCC[C@H](NC(=O)Nc1ccc(Br)cc1)C(=O)NCC(=O)OC(C)C]

tert-butyl{[(2S)-2-{[(4-bromophenyl)carbamoyl]amino}-4-methylpentanoyl]amino} acetate

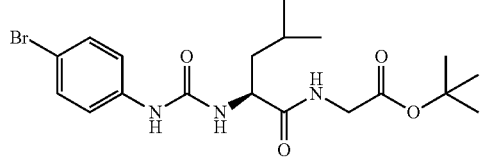 [SMILES: CC(C)C[C@H](NC(=O)Nc1ccc(Br)cc1)C(=O)NCC(=O)OC(C)(C)C]

(2S)-2-{[(4-bromophenyl)carbamoyl]amino}-N-(2-hydroxyethyl)-4-methylpentanamide

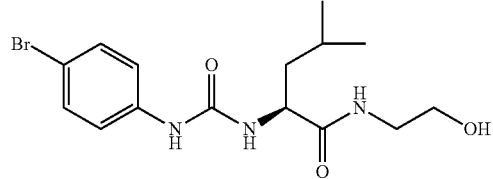 [SMILES: CC(C)C[C@H](NC(=O)Nc1ccc(Br)cc1)C(=O)NCCO]

(2S)-2-{[(4-bromophenyl)carbamoyl]amino}-4-methyl-N-(2-oxopropyl)pentanamide

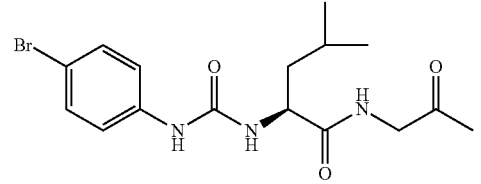 [SMILES: CC(=O)CNC(=O)[C@H](CC(C)C)NC(=O)Nc1ccc(Br)cc1]

(2S,3S)-N-(2-amino-2-oxoethyl)-2-{[(4-bromophenyl)carbamoyl]amino}-3-methylpentanamide

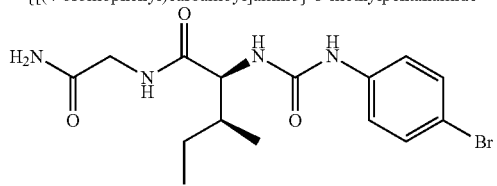

(2S,3S)-N-(2-amino-2-oxoethyl)-2-{[(4-bromo-2-fluorophenyl)carbamoyl]amino}-3-methylpentanamide

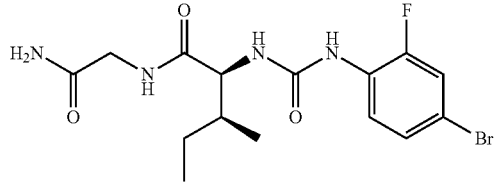 [SMILES: CC[C@H](C)[C@H](NC(=O)Nc1ccc(Br)cc1F)C(=O)NCC(N)=O]

(2S)-N-(2-amino-2-oxoethyl)-2-{[(4-bromophenyl)carbamoyl]amino}-pentanamide

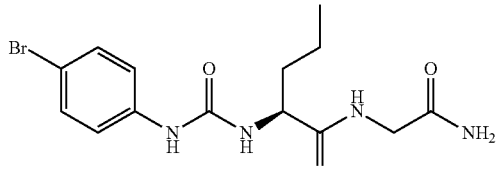

(2S)-N-(2-amino-2-oxoethyl)-2-{[(4-bromo-2-fluorophenyl)carbamoyl} amino)pentanamide

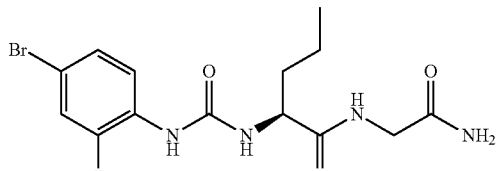

(2S)-N-(2-amino-2-oxoethyl)-2-{[(4-bromophenyl)carbamoyl]amino}-4-methylpentanamide

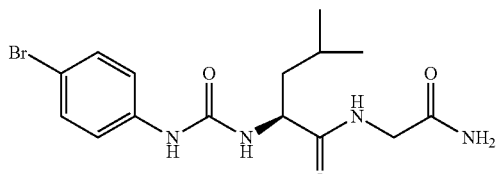

tert-butyl{[(2S)-2-{[(4-bromo-2-fluorophenyl)carbamoyl]amino}-4-methylpentanoyl]amino}acetate

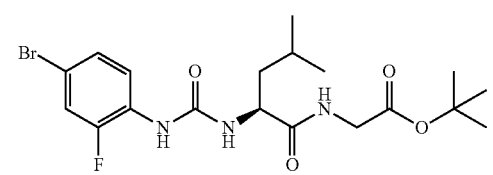 [SMILES: CC(C)C[C@H](NC(=O)Nc1ccc(Br)cc1F)C(=O)NCC(=O)OC(C)(C)C]

{[(2S)-2-{[(4-bromo-2-fluorophenyl)carbamoyl]amino}-4-methylpentanoyl]amino}acetic acid

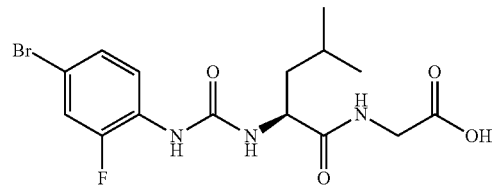 [SMILES: CC(C)C[C@H](NC(=O)Nc1ccc(Br)cc1F)C(=O)NCC(=O)O]

(2S)-2-{[(4-bromo-2-fluorophenyl)carbamoyl]amino}-4-methyl-N-(2-oxopropyl)pentanamide

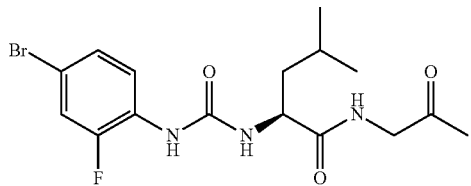 [SMILES: CC(=O)CNC(=O)[C@H](CC(C)C)NC(=O)Nc1ccc(Br)cc1F]

(2S)-2-{[(4-bromo-2-fluorophenyl)carbamoyl]amino}-N-(2-hydroxyethyl)-4-methylpentanamide

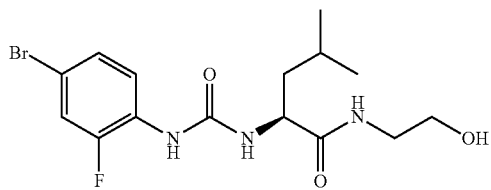 [SMILES: CC(C)C[C@H](NC(=O)Nc1ccc(Br)cc1F)C(=O)NCCO]

(2S)-N-(2-amino-2-oxoethyl)-2-{[(4-bromo-2-fluorophenyl)carbamoyl]amino}-4-methylpentanamide

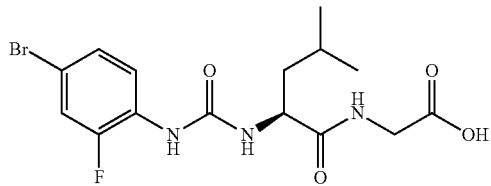 [SMILES: CC(C)C[C@H](NC(=O)Nc1ccc(Br)cc1F)C(=O)NCC(=O)O]

tert-butyl (2S)-2-{[(2S)-2-{[(4-bromo-2-fluorophenyl)carbamoyl]amino}-4-methylpentanoyl]amino}propanoate

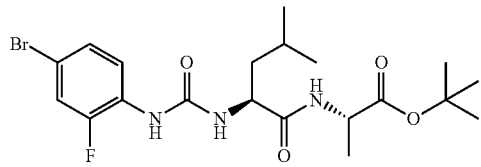 [SMILES: CC(C)C[C@H](NC(=O)Nc1ccc(Br)cc1F)C(=O)N[C@@H](C)C(=O)OC(C)(C)C]

(2S)-2-{[(2S)-2-{[(4-bromo-2-fluorophenyl)carbamoyl]amino}-4-methylpentanoyl]amino}propanoic acid

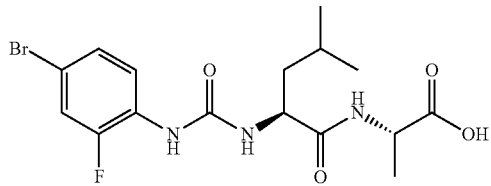 [SMILES: CC(C)C[C@H](NC(=O)Nc1ccc(Br)cc1F)C(=O)N[C@@H](C)C(=O)O]

(2S)-N-{(1S)-2-amino-1-methyl-2-oxoethyl]-2-{[(4-bromo-2-fluorophenyl)carbamoyl]amino}-4-methylpentanamide

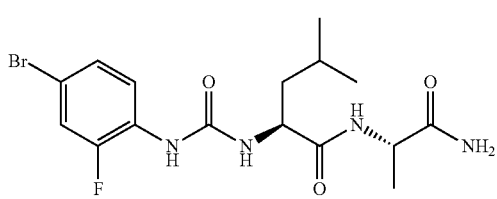 [SMILES: CC(C)C[C@H](NC(=O)Nc1ccc(Br)cc1F)C(=O)N[C@@H](C)C(N)=O]

tert-butyl (2S)-2-{[(2S)-2-({[(4-bromophenyl)carbamoyl}amino)-4-methylpentanoyl]amino}propanoate

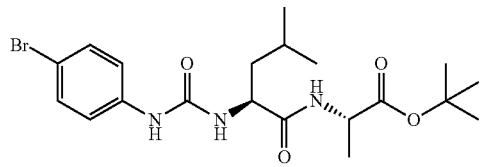 [SMILES: CC(C)C[C@H](NC(=O)Nc1ccc(Br)cc1)C(=O)N[C@@H](C)C(=O)OC(C)(C)C]

tert-butyl (2S)-2-{[(2S)-2-{[(4-bromophenyl)carbamoyl]amino}-4-methylpentanoyl]amino}-3-methylbutanoate

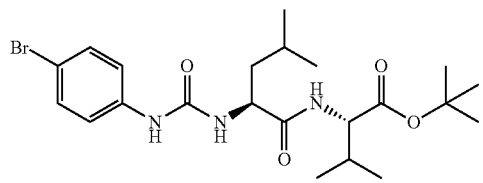 [SMILES: CC(C)C[C@H](NC(=O)Nc1ccc(Br)cc1)C(=O)N[C@H](C(=O)OC(C)(C)C)C(C)C]

(2S)-2-{[(2S)-2-{[(4-bromophenyl)carbamoyl]amino}-4-methylpentanoyl]amino}propanoic acid

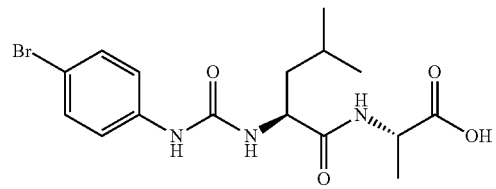 [SMILES: CC(C)C[C@H](NC(=O)Nc1ccc(Br)cc1)C(=O)N[C@@H](C)C(=O)O]

(2S)-2-{[(2S)-2-{[(4-bromophenyl)carbamoyl]amino}-4-methylpentanoyl]amino}-3-methylbutanoic acid

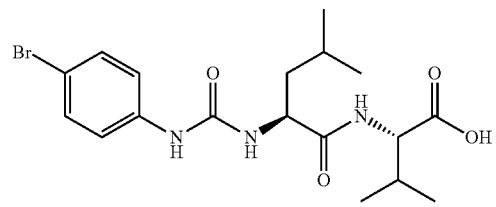 [SMILES: CC(C)C[C@H](NC(=O)Nc1ccc(Br)cc1)C(=O)N[C@H](C(=O)O)C(C)C]

(2S)-N-{(1S)-2-amino-1-methyl-2-oxoethyl]-2-{[(4-bromophenyl)carbamoyl]amino}-4-methylpentanamide

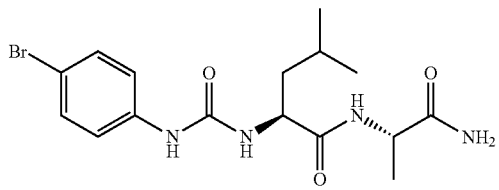 [SMILES: CC(C)C[C@H](NC(=O)Nc1ccc(Br)cc1)C(=O)N[C@@H](C)C(N)=O]

(2S)-N-{(1S)-1-(amino-3methyl-1-oxobutan-2-yl]-2-{[(4-bromophenyl)carbamoyl]amino}-4-methylpentanamide

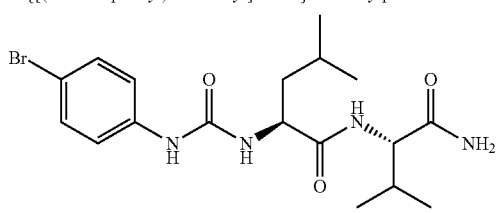

(2S)-2-{[(4-bromophenyl)carbamoyl]amino}-N-(2-hydroxy-2-methylpropyl)-4-methylpentanamide

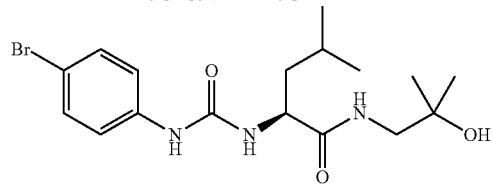 [SMILES: CC(C)C[C@H](NC(=O)Nc1ccc(Br)cc1)C(=O)NCC(C)(C)O]

(2S)-2-{[(4-bromophenyl)carbamoyl]amino}-N-[2-hydroxy-1-(hydroxymethyl)ethyl]-4-methylpentanamide

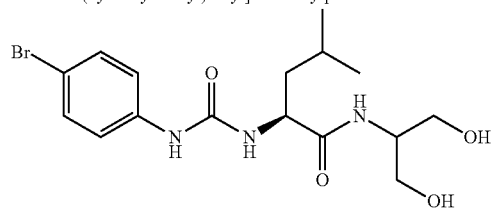

(2S)-2-{[(4-bromophenyl)carbamoyl]amino}-N-(2,3-dihydroxypropyl)-4-methylpentanamide

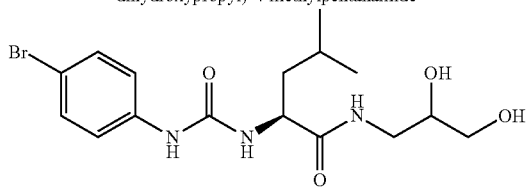

(2S)-2-{[(4-bromophenyl)carbamoyl]amino}-N-[(1R)-2-hydroxy-1-methylethyl]-4-methylpentanamide

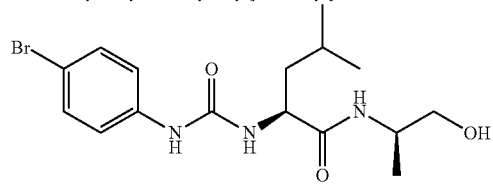

tert-butyl (2S)-2-{[(2S)-2-{[4-bromophenyl)carbamoyl]amino}-4-methyl pentanoyl]amino}propanoate

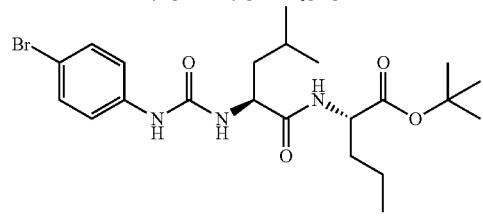

tert-butyl (2S)-{[(2S)-2-{[(4-bromophenyl)carbamoyl]amino}-4-methylpentanoyl]amino}(phenyl)ethanoate

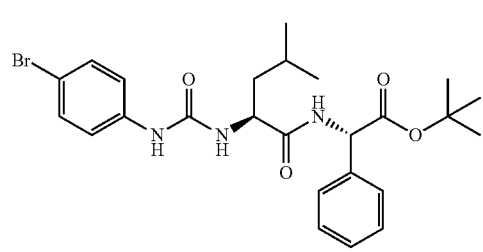 [SMILES: CC(C)C[C@H](NC(=O)Nc1ccc(Br)cc1)C(=O)N[C@H](C(=O)OC(C)(C)C)c1ccccc1]

(2S)-2-{[(2S)-2-{[(4-bromophenyl)carbamoyl]amino}-4-methylpentanoyl]amino}pentanoic acid

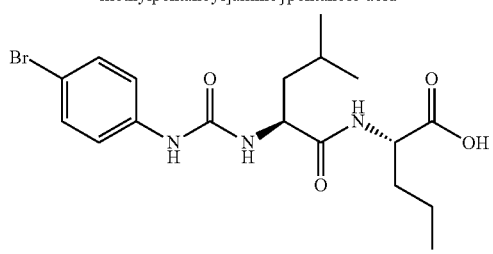

(2S)-{[(2S)-2-{[(4-bromophenyl)carbamoyl]amino}-4-methylpentanoyl]amino}(phenyl)ethanoic acid

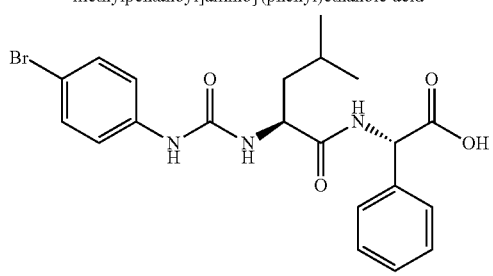

(2S)-N-[(2S)-1-amino-1-oxopentan-2-yl]-2-{[(4-bromophenyl)carbamoyl]amino}-4-methylpentanamide

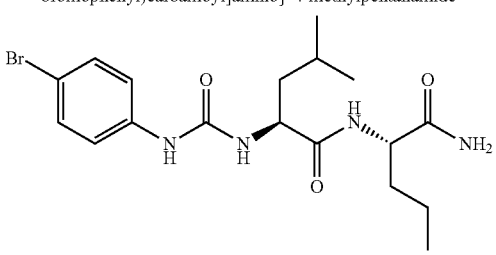

(2S)-N-[(1S)-2-amino-2-oxo-1-phenylethyl]-2-{[(4-bromophenyl)carbamoyl]amino}-4-methylpentanamide

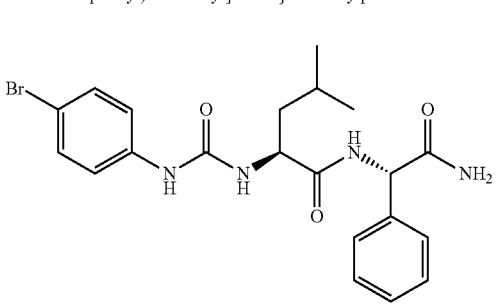

tert-butyl{[2-{[(4-bromophenyl)carbamoyl]amino}-2,4-dimethylpentanoyl]amino}acetate

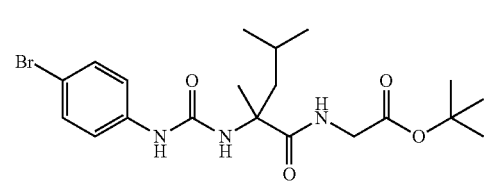 [SMILES: CC(C)CC(C)(NC(=O)Nc1ccc(Br)cc1)C(=O)NCC(=O)OC(C)(C)C]

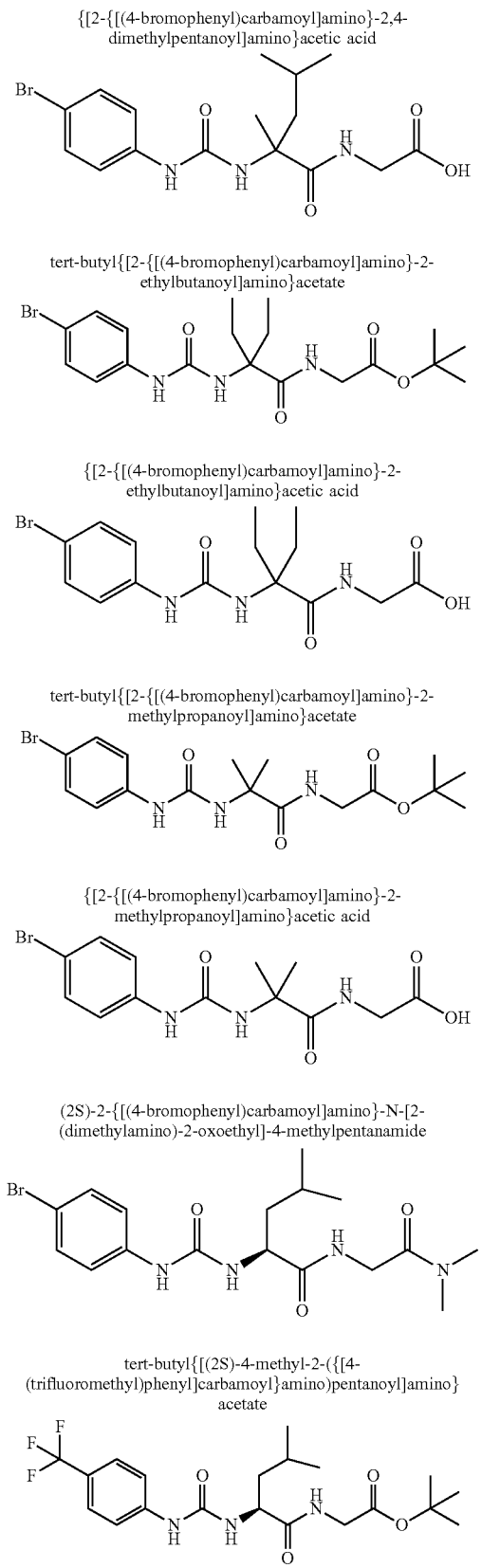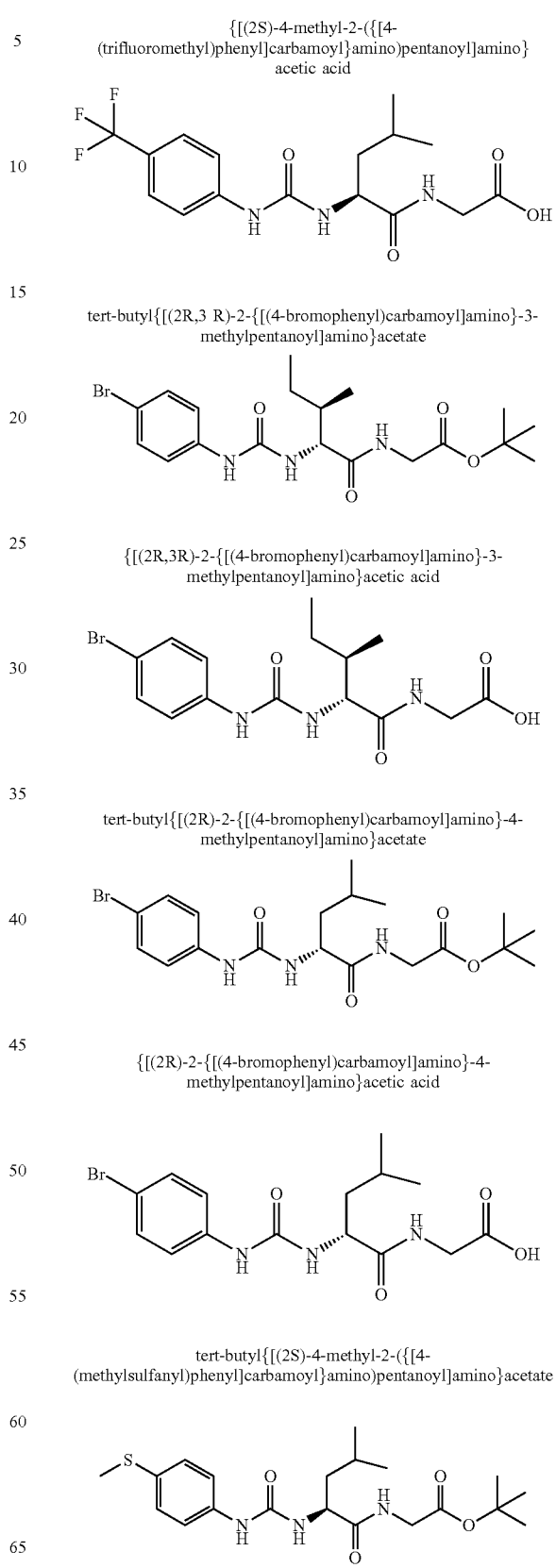

-continued 2-methyl-2-{[(2S)-4-methyl-2-({[4-(trifluoromethyl)phenyl]carbamoyl}amino)pentanoyl]amino}propanoic acid

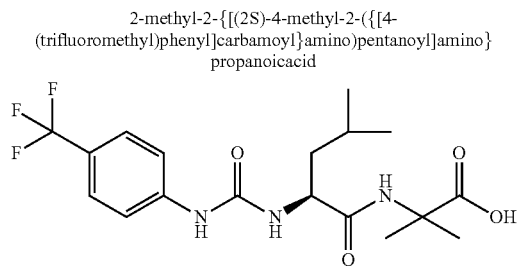

{[(2S)-4-methyl-2-({[4-(methylsulfanyl)phenyl]carbamoyl}amino)pentanoyl]amino}acetic acid

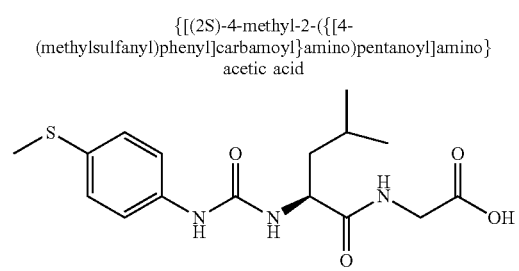

tert-butyl ({(2S)-4-methyl-2-[({4-[(trifluoromethyl)sulfanyl]phenyl}carbamoyl)amino]pentanoyl}amino)acetate

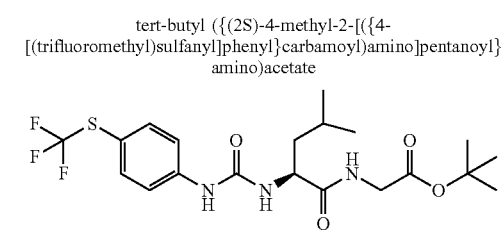

({(2S)-4-methyl-2-[({4-[(trifluoromethyl)sulfanyl]phenyl}carbamoyl)amino]pentanoyl}amino)acetic acid

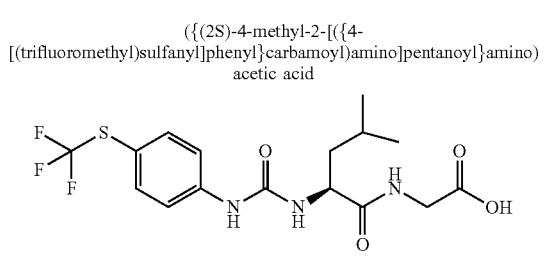

tert-butyl 2-{[(2S)-2-{[(4-bromophenyl)carbamoyl]amino}-4-methylpentanoyl]amino}-2-methylpropanoate

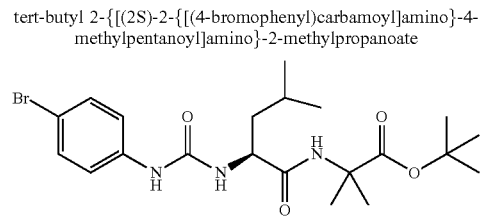

2-{[(2S)-2-{[(4-bromophenyl)carbamoyl]amino}-4-methylpentanoyl]amino}-2-methylpropanoic acid

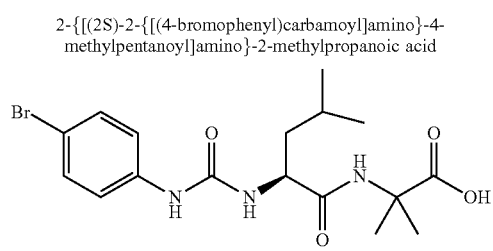

-continued tert-butyl{[(2S)-4-methyl-2-({[4-(methylsulfinyl)phenyl]carbamoyl}amino)pentanoyl]amino}acetate

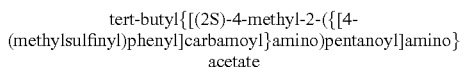
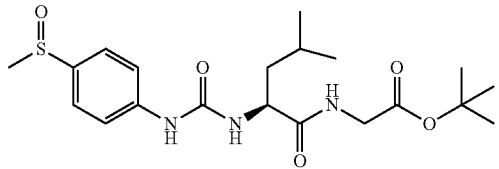 [SMILES: CC(C)C[C@H](NC(=O)Nc1ccc(S(C)=O)cc1)C(=O)NCC(=O)OC(C)(C)C]

tert-butyl{[(2S)-4-methyl-2-({[4-(methylsulfonyl)phenyl]carbamoyl}amino)pentanoyl]amino}acetate

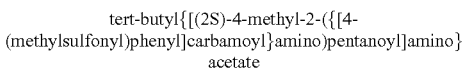
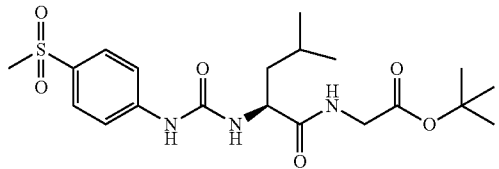 [SMILES: CC(C)C[C@H](NC(=O)Nc1ccc(S(C)(=O)=O)cc1)C(=O)NCC(=O)OC(C)(C)C]

{[(2S)-4-methyl-2-({[4-(methylsulfinyl)phenyl]carbamoyl}amino)pentanoyl]amino}acetic acid

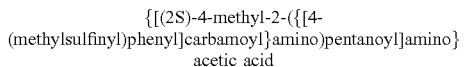
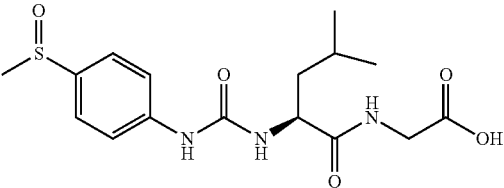 [SMILES: CC(C)C[C@H](NC(=O)Nc1ccc(S(C)=O)cc1)C(=O)NCC(=O)O]

{[(2S)-4-methyl-2-({[4-(methylsulfonyl)phenyl]carbamoyl}amino)pentanoyl]amino}acetic acid

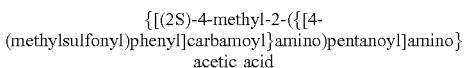
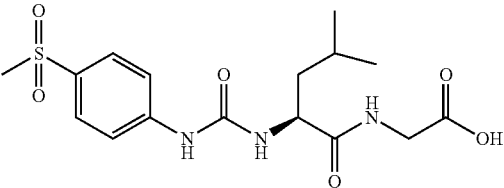 [SMILES: CC(C)C[C@H](NC(=O)Nc1ccc(S(C)(=O)=O)cc1)C(=O)NCC(=O)O]

tert-butyl 2-methyl-2-{[(2S)-4-methyl-2-({[4-(trifluoromethyl)phenyl]carbamoyl}amino)pentanoyl]amino}propanoate

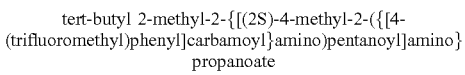
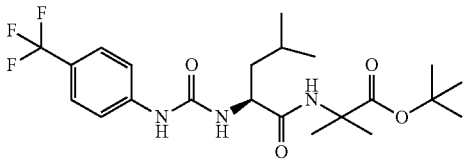 [SMILES: CC(C)C[C@H](NC(=O)Nc1ccc(C(F)(F)F)cc1)C(=O)NC(C)(C)C(=O)OC(C)(C)C]

tert-butyl{[(2S)-2-{[(4-bromophenyl)carbamoyl]amino}-4-(methylsulfanyl)butanoyl]amino}acetate

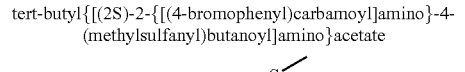
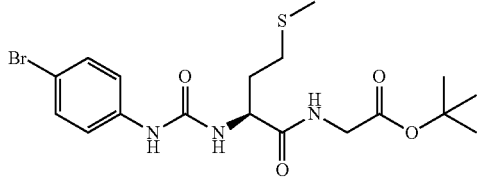 [SMILES: CSCC[C@H](NC(=O)Nc1ccc(Br)cc1)C(=O)NCC(=O)OC(C)(C)C]

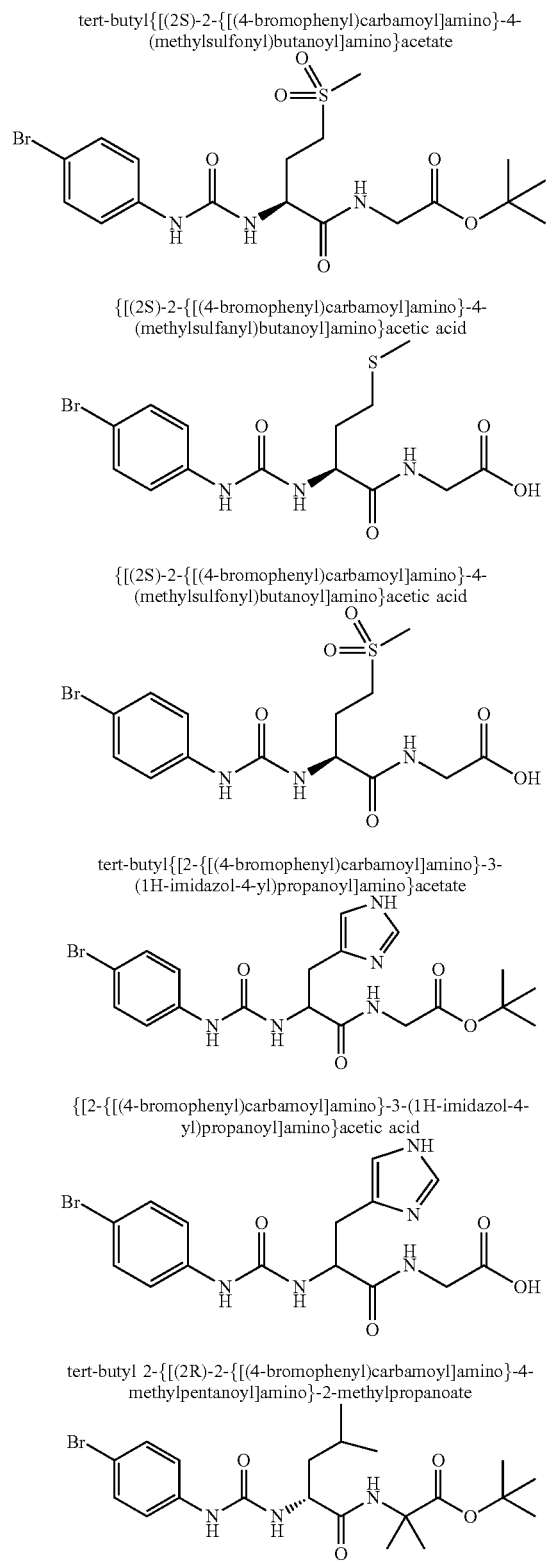
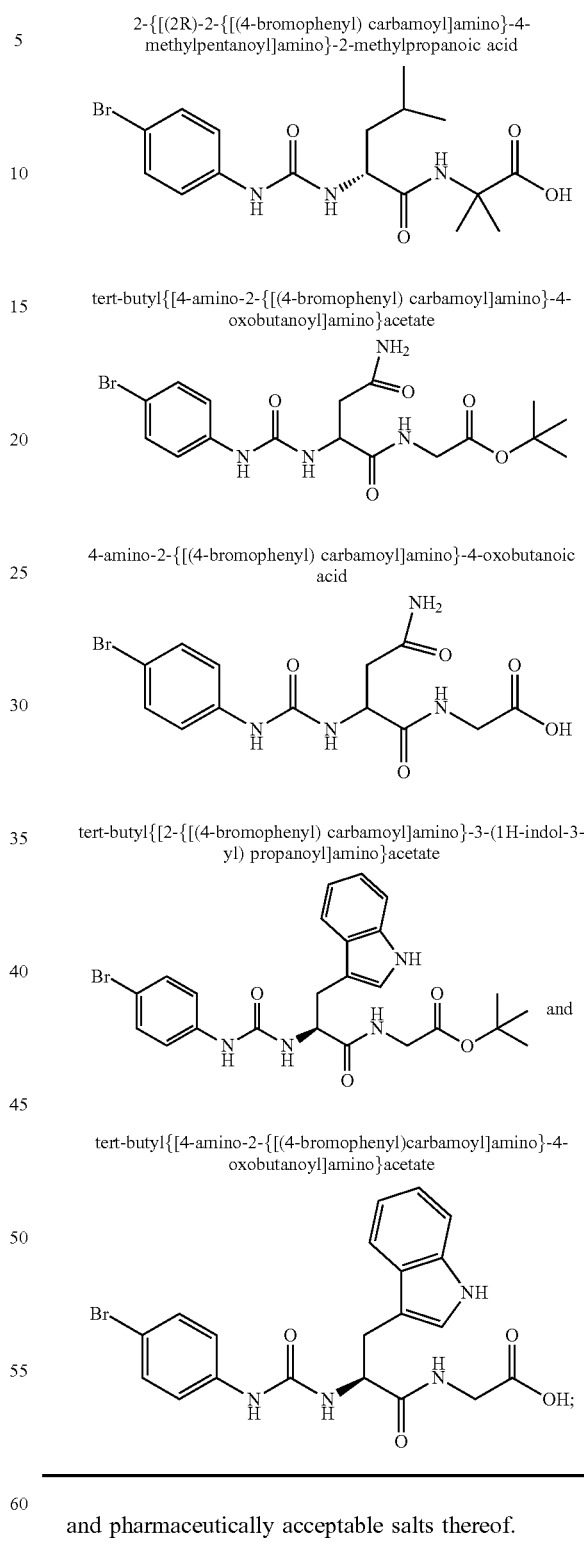
and pharmaceutically acceptable salts thereof.
* * * * *

UNITED STATES PATENT AND TRADEMARK OFFICE
CERTIFICATE OF CORRECTION

PATENT NO. : 9,850,264 B2
APPLICATION NO. : 14/196047
DATED : December 26, 2017
INVENTOR(S) : Richard L. Beard et al.

Page 1 of 3

It is certified that error appears in the above-identified patent and that said Letters Patent is hereby corrected as shown below:

On the Title Page

In item (*), in Column 1, above item (21), insert -- This patent is subject to a terminal disclaimer. --.

In item (56), in Column 2, under "Other Publications", Line 2, after "Medicinal" insert -- Chemistry --.

On the Page 2, in Column 1, under "Other Publications", Line 7, delete "Pharamcology" and insert -- Pharmacology --, therefor.

On the Page 2, in Column 1, under "Other Publications", Lines 13-14, delete "an dinternalization" and insert -- and internalization --, therefor.

On the Page 2, in Column 1, under "Other Publications", Line 16, delete "Mysoin" and insert -- Myosin --, therefor.

On the Page 2, in Column 2, under "Other Publications", Line 2, before "73:" insert -- 2005; --.

On the Page 2, in Column 2, under "Other Publications", Line 6, delete "FPR2IALX" and insert -- FPR2/ALX --, therefor.

On the Page 2, in Column 2, under "Other Publications", Line 9, delete "Asprin-" and insert -- Aspirin- --, therefor.

In the Specification

In Column 1, Lines 38-39, delete "glucocotricoid-" and insert -- glucocorticoid- --, therefor.

In Column 3, Line 34, delete "(PONS)," and insert -- (POHS), --, therefor.

Signed and Sealed this
Twelfth Day of June, 2018

Andrei Iancu
*Director of the United States Patent and Trademark Office*

In Column 9, Line 28, delete "Unsubstituted" and insert -- unsubstituted --, therefor.

In Column 11, Line 19, after "cycloalkenyl" insert -- , --.

In Column 11, Lines 53-63, delete " 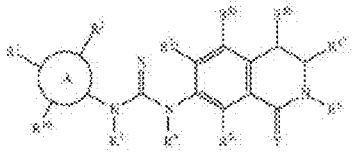 " and insert -- 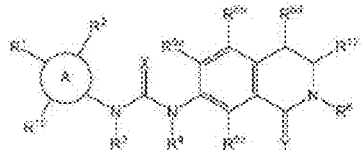 --, therefor.

In Column 11, Line 65, delete "heterocyle," and insert -- heterocycle, --, therefor.

In Column 12, Line 9, delete "heterocyle," and insert -- heterocycle, --, therefor.

In Column 12, Line 39, delete "—(CH$_2$), heterocycle," and insert -- —(CH$_2$)$_m$heterocycle, --, therefor.

In Column 13, Lines 47-48, delete "—OC(O)R$^{21}$—SR$^{11}$," and insert -- —OC(O)R$^{21}$, —SR$^{11}$, --, therefor.

In Column 16, Line 31, delete ""—C(O)ON"." and insert -- "—C(O)OH". --, therefor.

In Columns 17-18, Line 3, delete "Gal 6-CHO" and insert -- Ga16-CHO --, therefor.

In Columns 19-20, Line 3, delete "Gal 6-CHO" and insert -- Ga16-CHO --, therefor.

In Columns 19-20, Line 15, delete "3-pheny1-" and insert -- 3-phenyl- --, therefor.

In Columns 19-20, Lines 21-22, delete "(p henyl)" and insert -- (phenyl) --, therefor.

In Column 21, Line 25, delete "factor X" and insert -- factor Xa --, therefor.

In Columns 21-22, Line 3, delete "Gal 6-CHO" and insert -- Ga16-CHO --, therefor.

In Columns 21-22, Line 8, delete "-indo1-" and insert -- -indol- --, therefor.

In Column 30, Line 23, delete "(PONS)," and insert -- (POHS), --, therefor.

In Columns 47-48, Line 23, after "42" delete "$^{1p;1p}$".

In Columns 75-76, Line 14, delete "237" and insert -- 137 --, therefor.

In the Claims

In Column 82, Line 47, in Claim 1, delete "1," and insert -- 1; --, therefor.

In Column 82, Line 52, in Claim 1, delete "-NR$^{11}$ R$^{12}$ or -OR$^{13}$ ;" and insert -- -NR$^{11}$R$^{12}$ or -OR$^{13}$; --, therefor.

In Column 82, Lines 55-56, in Claim 1, delete "—NR$^{11}$ R$^{12}$, NO$_2$" and insert -- —NR$^{11}$R$^{12}$, NO$_2$, --, therefor.

In Column 82, Line 60, in Claim 1, delete "—NR$^{11}$ R$^{12}$," and insert -- —NR$^{11}$R$^{12}$, --, therefor.

In Column 82, Line 64, in Claim 1, delete "—S(O)$_n$ R$^{14}$;" and insert -- —S(O)$_n$R$^{14}$; --, therefor.

In Column 82, Line 67, in Claim 1, delete "—NR$^{11}$ R$^{12}$, NO$_2$," and insert -- —NR$^{11}$R$^{12}$, NO$_2$, --, therefor.

In Column 83, Line 4, in Claim 1, delete "R$^7$is" and insert -- R$^7$ is --, therefor.

In Column 83, Line 5, in Claim 1, delete "—NR$^{11}$ R$^{12}$," and insert -- —NR$^{11}$R$^{12}$, --, therefor.

In Column 83, Line 13, in Claim 1, delete "R$^{10}$is" and insert -- R$^{10}$ is --, therefor.

In Column 90, Line 57, in Claim 2, delete "-3methyl-" and insert -- -3-methyl- --, therefor.

In Column 94, Line 16, in Claim 2, delete "(2R,3 R)-" and insert -- (2R,3R)- --, therefor.

In Column 95, Line 6, in Claim 2, delete "propanoicacid" and insert -- propanoic acid --, therefor.